United States Patent
Jiang et al.

(10) Patent No.: US 10,961,178 B2
(45) Date of Patent: Mar. 30, 2021

(54) CYCLOADDITION REACTIONS USING QUANTUM DOTS

(71) Applicant: Northwestern University, Evanston, IL (US)

(72) Inventors: Yishu Jiang, Evanston, IL (US); Cameron R. Rogers, Evanston, IL (US); Mohamad S. Kodaimati, Evanston, IL (US); Emily A. Weiss, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/851,974

(22) Filed: Apr. 17, 2020

(65) Prior Publication Data
US 2020/0331836 A1    Oct. 22, 2020

Related U.S. Application Data

(60) Provisional application No. 62/835,778, filed on Apr. 18, 2019.

(51) Int. Cl.
*C07C 51/42* (2006.01)
*C07C 51/353* (2006.01)

(52) U.S. Cl.
CPC ............ *C07C 51/353* (2013.01); *C07C 51/42* (2013.01)

(58) Field of Classification Search
CPC .............................. C07C 51/353; C07C 51/42
See application file for complete search history.

(56) References Cited

PUBLICATIONS

Lei et al. (General and Efficient Intermolecular [2+2] Photodimerization of Chalcones and Cinnamic Acid Derivatives in Solution through Visible-Light Catalysis, Angewandte Chemie. Int. Ed., 56, pp. 15407-15410, Published 2017. As cited in the IDS filed Sep. 2, 2020) (Year: 2017).*
Alonso et al. "A Chiral Thioxanthone as an Organocatalyst for Enantioselective [2+2] Photocycloaddition Reactions Induced by Visible Light," *Angew. Chem.* 126, 4457-4460 (2014).
Blum et al. "Enantioselective photochemistry through Lewis acid—catalyzed triplet energy transfer," *Science* 354, 1391-1395 (2016).
Chen et al. "Enantioselective NiH/Pmrox-Catalyzed 1,2-Reduction of a,b-Unsaturated Ketones," *Angew. Chem. Int. Ed.* 56, 2022-2025 (2017).
Deck et al. "Activation of anti-oxidant Nrf2 signaling by enone analogues of Curcumin," *Eur. J. Med. Chem.* 143, 854-865 (2018).
Flamee et al. "Fast, High Yield, and High Solid Loading Synthesis of Metal Selenide Nanocrystals," *Chem. Mater.* 25, 2476-2483 (2013).
Gutekunst et al. "Applications of C—H Functionalization Logic to Cyclobutane Synthesis," *J. Org. Chem.* 79, 2430-2452 (2014).
Harris et al. "Electronic Processes within Quantum Dot-Molecule Complexes," *Chem. Rev.* 116, 12865-12919 (2016).
Hörmann et al. "Evidence for Triplet Sensitization in the Visible-Light-Induced [2+2] Photocycloaddition of Eniminium Ions," *Angew. Chem. Int. Ed.* 57, 827-831 (2018).
Hu et al. "Catalytic Asymmetric Dearomatization by Visible-Light-Activated [2+2] Photocycloaddition," *Angew. Chem. Int. Ed.* 57, 6242-6246 (2018).
Jiang et al. "Regio- and diastereoselective intermolecular [2+2] cycloadditions photocatalysed by quantum dots," *Nat. Chem.* 2019, 11(11) 1034-1040.
Kershaw et al., "Narrow bandgap colloidal metal chalcogenide quantum dots: synthetic methods, heterostructures, assemblies, electronic and infrared optical properties," *Chem. Soc. 25 Rev.*, 42, 3033-3087 (2013).
Lei et al. "General and Efficient Intermolecular [2+2] Photodimerization of Chalcones and Cinnamic Acid Derivatives in Solution through Visible-Light Catalysis," *Angew. Chem. Int. Ed.* 56, 15407-15410 (2017).
Maturi et al. "Enantioselective Catalysis of the Intermolecular [2+2] Photocycloaddition between 2-Pyridones and Acetylenedicarboxylates," *Angew. Chem. Int. Ed.* 53, 7661-7664 (2014).
Pagire et al. "Photosensitised regioselective [2+2]-cycloaddition of cinnamates and related alkenes," *Chem. Commun.* 53, 12072-12075 (2017).
Pu et al. "Colloidal Synthesis of Semiconductor Quantum Dots toward Large-Scale Production: A Review," *Ind. Eng. Chem. Res.* 57, 1790-1802 (2018).
Ullrich et al. "Scope and Applicability of an Expedient Synthesis Leading to Polysubstituted 3-(Carboxyphenyl)pyrroles," *Synth. Commun.* 37, 1109-1119 (2007).

* cited by examiner

*Primary Examiner* — Jafar F Parsa
*Assistant Examiner* — Blaine G Doletski
(74) *Attorney, Agent, or Firm* — Casimir Jones, S.C.; Anne M. Reynolds

(57) ABSTRACT

Disclosed herein are methods in which colloidal quantum dots (QDs) can serve as visible-light chromophores, photocatalysts, and reusable scaffolds for homo- and hetero-intermolecular [2+2] photocycloadditions. The methods may lead to >90% tunable regioselectivity and up to 98% diastereoselectivity for previously minor syn-cyclobutane products, including the syn-head-to-tail cyclobutane.

20 Claims, 5 Drawing Sheets

FIG. 3A
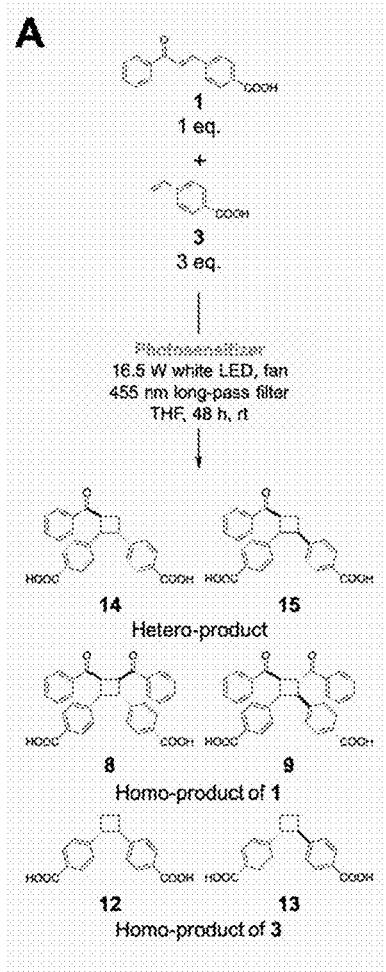
FIG. 3B
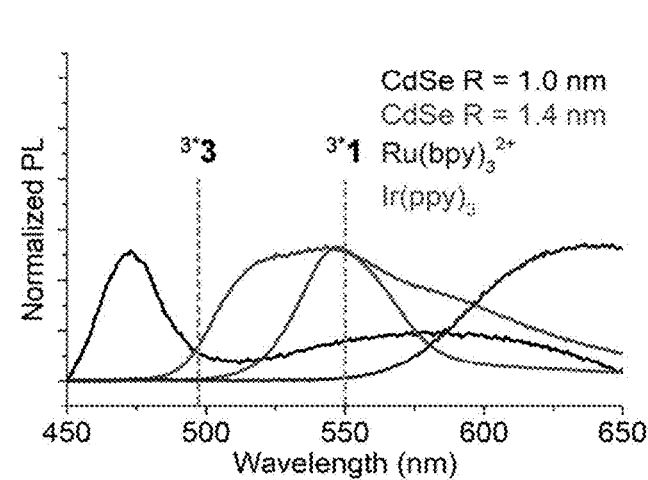
FIG. 3C

CYCLOADDITION REACTIONS USING QUANTUM DOTS

CROSS-REFERENCE TO RELATED APPLICATIONS

This application claims priority to U.S. Provisional Patent Application No. 62/835,778, filed on Apr. 18, 2019, the entire contents of which are fully incorporated herein by reference.

STATEMENT REGARDING FEDERALLY SPONSORED RESEARCH

This invention was made with government support under Grant 9550-17-1-0271 awarded by the Air Force Office of Scientific Research. The government has certain rights in the invention.

FIELD

Provided herein are compositions and methods for conducting photo-driven [2+2] cycloaddition reactions using quantum dots.

BACKGROUND

Photo-driven [2+2] cycloaddition reactions are simple routes to tetrasubstituted cyclobutanes, which are core components of many important bioactive molecules that may have applications as lead compounds for drug development. Significant advances in the chemoselectivity and enantioselectivity of [2+2] photocycloadditions have been made, but exceptional diastereoselectivity and regioselectivity (head-to-head vs. head-to-tail adducts), which may be required for synthesis of certain bioactive molecules, have not yet been achieved. Furthermore, fast cis/trans isomerization of aryl-conjugated alkenes like stilbenes significantly limits their use as substrates in photocycloadditions.

Although enantioselective intermolecular [2+2] photocycloadditions have been carried out in the presence of hydrogen bonding templates (Alonso et al. *Angew. Chem.* 126, 4457-4460 (2014); Maturi et al. *Angew. Chem. Int. Ed.* 53, 7661-7664 (2014)), chiral secondary amines (Hormann et al. *Angew. Chem. Int. Ed.* 57, 827-831 (2018)), chiral ligands of molecular catalysts (Hu et al. *Angew. Chem. Int. Ed.* 57, 6242-6246), and Lewis-acid co-catalysts (Blum et al. *Science* 354, 1391-1395 (2016)), outstanding challenges include the competing fast cis/trans isomerization pathway of the substrates, and achieving selectivities for a particular regioisomer or diastereoisomer of the coupled product and for homo- vs. heterocoupling within a mixture of reactive olefins. The latter is a priority because cyclobutane natural products and related compounds predominantly comprise two distinct olefins (Gutekunst et al. *J. Org. Chem.* 79, 2430-2452 (2014)).

SUMMARY

Disclosed herein is a method of synthesizing a substituted cyclobutane compound, the method comprising:

(a) providing a compound of formula (I) and a compound of formula (II):

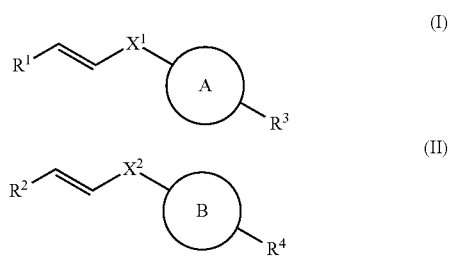

wherein:
$X^1$ and $X^2$ are each independently selected from a bond and —C(O)—;
$R^1$ and $R^2$ are each independently selected from hydrogen, alkyl, cycloalkyl, aryl, heterocyclyl, heteroaryl, —C(O)-alkyl, and —C(O)-aryl; and
$R^3$ and $R^4$ are each independently selected from —COOH and —NH$_2$;
A and B are each independently selected from aryl;
wherein the alkyl, cycloalkyl, aryl, heterocyclyl, and heteroaryl are optionally substituted;

(b) providing a plurality of quantum dots;

(c) combining the compound of formula (I), the compound of formula (II), and the quantum dots in a solvent to provide a mixture; and (d) subjecting the mixture to irradiation, to thereby synthesize the substituted cyclobutane compound.

In some embodiments, the substituted cyclobutane compound is a compound of formula (III):

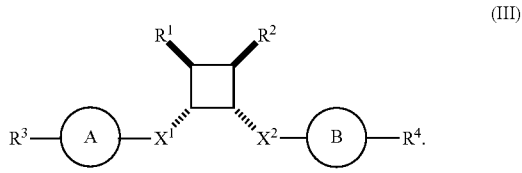

In some embodiments, the compound of formula (III) is synthesized with a diastereomeric ratio of greater than 10:1 compared to a compound of formula (IV):

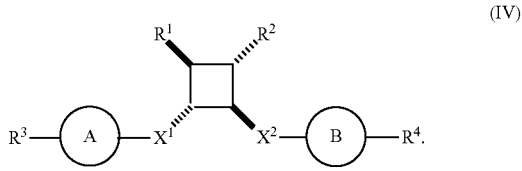

In some embodiments, the compound of formula (III) is synthesized with a ratio of greater than 10:1 compared to a compound of formula (V):

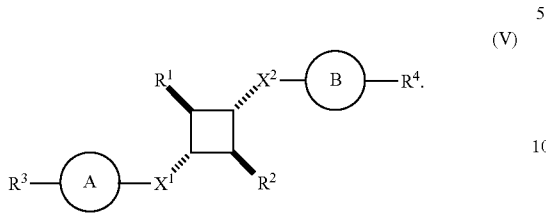

(V)

In some embodiments, the compound of formula (I) is a compound of formula (Ia), and the compound of formula (II) is a compound of formula (IIa):

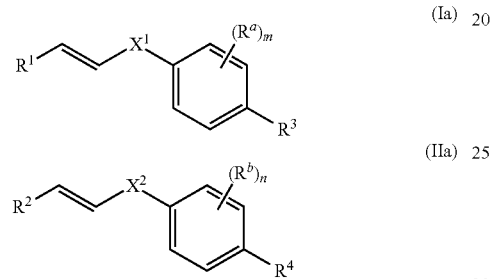

(Ia)

(IIa)

wherein:
$R^a$ and $R^b$ are each independently selected from alkyl, alkenyl, alkynyl, halogen, haloalkyl, cycloalkyl, cycloalkenyl, aryl, —OR, —C(O)R, —C(O)OR, —NRR', —C(O)NRR', and —NR'C(O)R;
each R is independently selected from alkyl, alkenyl, alkynyl, cycloalkyl, cycloalkenyl, aryl, heteroaryl, and heterocyclyl;
each R' is independently selected from hydrogen, alkyl, alkenyl, alkynyl, cycloalkyl, cycloalkenyl, aryl, heteroaryl, and heterocyclyl;
m is 0, 1, or 2; and
n is 0, 1, or 2.

In some embodiments, the substituted cyclobutane compound is a compound of formula (IIIa):

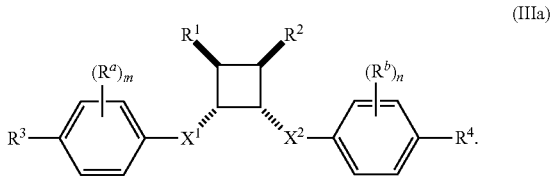

(IIIa)

In some embodiments, the compound of formula (I) is a compound of formula (Ib), and the compound of formula (II) is a compound of formula (IIb):

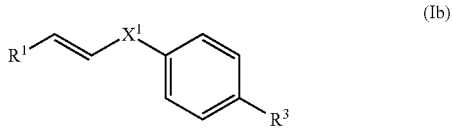

(Ib)

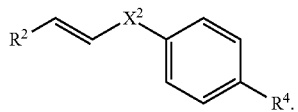

(IIb)

In some embodiments, the substituted cyclobutane compound is a compound of formula (IIIb):

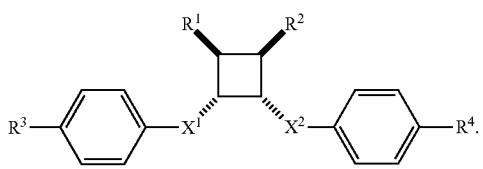

(IIIb)

In some embodiments, the compound of formula (I) and the compound of formula (II) are the same. In some embodiments, the compound of formula (I) and the compound of formula (II) are different.

In some embodiments, the quantum dots are CdSe quantum dots.

In some embodiments, the method further comprises separating the quantum dots from the mixture from the substituted cyclobutane compound after step (d).

In some embodiments, the quantum dots have an average radius of 1.0 to 1.4 nm.

In some embodiments, the quantum dots further comprise a capping molecule on the surface of the quantum dots. In some embodiments, the capping molecule is oleic acid.

In some embodiments, the solvent is tetrahydrofuran.

In some embodiments, the method comprises irradiating the mixture for 24-72 hours (e.g., 48 hours). In some embodiments, the method comprises irradiating the mixture for 4 days. In some embodiments, the method comprises irradiating the mixture using a 16.5 W white-light LED with a 455 nm longpass filter. In some embodiments, the method comprises irradiating the mixture using a blue LED (emission centered at 467 nm).

In some embodiments, the quantum dots are present in the mixture in an amount of 0.4 mol % to 1.2 mol %.

BRIEF DESCRIPTION OF THE DRAWINGS

FIGS. 3A-3C show: (A) conditions for and possible products of [2+2] photocycloadditions of Compound 1 and Compound 3; (B) emission spectra of four photosensitizers, compared with the triplet energies of substrates Compound 1 and Compound 3, determined from phosphorescence spectra and calculations; and (C) product distributions from reaction mixtures with the four photosensitizers. The yields listed are for the regioisomers indicated (drawn in A); the remaining mass is exclusively starting materials and the cis-isomer of Compound 1 for the QD systems, and the same plus minor unidentified side products for the molecule-catalyzed reactions. *The yields in red are calculated in reference to substrate 3, which was added in excess.

DEFINITIONS

Figure 1A:
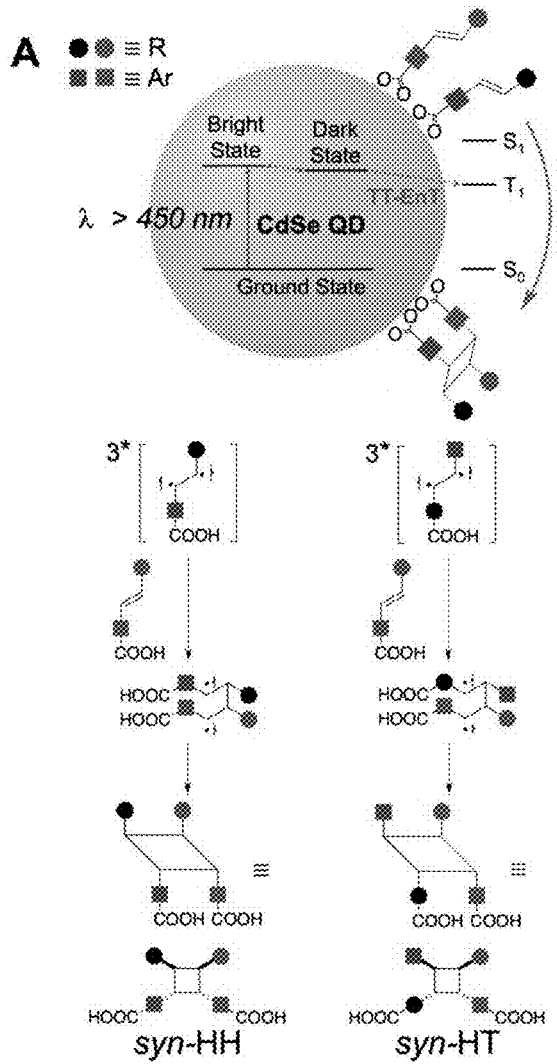
FIGS. 1A-1D show sensitization via the QD photocatalyst and mechanisms of selectivity: (A) Sensitization of the triplet excited state of the substrate (T1) through triplet-triplet energy transfer (TT-EnT) from CdSe QDs, and schematic representation of syn-HH (head-to-head) or syn-HT (head-to-tail) selectivity of QDs. (B) Chemical structures of the molecular sensitizers compared to the QDs, and the mechanism of anti-HH preference of reactions driven by these molecules. (C) Ground state absorption spectra of a mixture of CdSe QDs (radius=1.4 nm) and Compound 1 in THF, before and after three 48 h illumination cycles. The differences between spectra at λ<450 nm are due to consumption of Compound 1. (D) Decay dynamics of the exciton in CdSe QDs mixed with 250 equivalents of Compound 1 in TH upon photoexcitation at 470 nm, monitored at three wavelengths: 480 nm (pure electron dynamics), 900 nm (primarily electron dynamics), and 1300 nm (primarily hole dynamics).

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a quantum dot" is a reference to one or more quantum dots.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

The term "alkyl," as used herein, means a straight or branched saturated hydrocarbon chain containing from 1 to 16 carbon atoms ($C_1$-$C_{16}$ alkyl), 1 to 12 carbon atoms ($C_1$-$C_{12}$ alkyl), 1 to 10 carbon atoms ($C_1$-$C_{10}$ alkyl), 1 to 8 carbon atoms ($C_1$-$C_8$ alkyl), 1 to 6 carbon atoms ($C_1$-$C_6$ alkyl), 1 to 4 carbon atoms ($C_1$-$C_4$ alkyl), or 1 to 3 carbon atoms ($C_1$-$C_3$ alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecyl, and n-dodecyl.

The term "alkenyl," as used herein, refers to a straight or branched hydrocarbon chain containing from 2 to 16 carbon atoms and containing at least one carbon-carbon double bond. The alkenyl group can having 2 to 12 carbon atoms ($C_2$-$C_{12}$ alkenyl), 2 to 10 carbon atoms ($C_2$-$C_{10}$ alkenyl), 2 to 8 carbon atoms ($C_2$-$C_8$ alkenyl), 2 to 6 carbon atoms ($C_2$-$C_6$ alkenyl), 2 to 4 carbon atoms ($C_2$-$C_4$ alkenyl), or 2 to 3 carbon atoms ($C_2$-$C_3$ alkenyl). Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl," as used herein, refers to a straight or branched hydrocarbon chain containing from 2 to 16 carbon atoms and containing at least one carbon-carbon triple bond. The alkynyl group can having 2 to 12 carbon atoms ($C_2$-$C_{12}$ alkynyl), 2 to 10 carbon atoms ($C_2$-$C_{10}$ alkynyl), 2 to 8 carbon atoms ($C_2$-$C_8$ alkynyl), 2 to 6 carbon atoms ($C_2$-$C_6$ alkynyl), 2 to 4 carbon atoms ($C_2$-$C_4$ alkynyl), or 2 to 3 carbon atoms ($C_2$-$C_3$ alkynyl). Representative examples of alkynyl include, but are not limited to, ethynyl, propynyl, and butynyl.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "aryl," as used herein, refers to a phenyl group, or a bicyclic or tricyclic aromatic fused ring system. Bicyclic fused ring systems are exemplified by a phenyl group appended to the parent molecular moiety and fused to a phenyl group. Tricyclic fused ring systems are exemplified by a phenyl group appended to the parent molecular moiety and fused to two other phenyl groups. Representative examples of bicyclic aryls include naphthyl. Representative examples of tricyclic aryls include anthracenyl and phenanthrenyl.

The term "cycloalkyl" as used herein, refers to a carbocyclic ring system containing three to ten carbon atoms, zero heteroatoms and zero double bonds. The cycloalkyl may be monocyclic, bicyclic, bridged, fused, or spirocyclic. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1]pentanyl.

The term "halogen" or "halo," as used herein, means F, $C_1$, Br, or I.

The term "haloalkyl," as used herein, means an alkyl group, as defined herein, in which one or more hydrogen atoms are replaced by a halogen. For example, one, two, three, four, five, six, seven or eight hydrogen atoms can be replaced by a halogen, or all hydrogen atoms can be replaced by a halogen. Representative examples of haloalkyl include, but are not limited to, fluoromethyl, difluoromethyl, trifluoromethyl, chloromethyl, dichloromethyl, trichloromethyl, 2-fluoroethyl, 2,2-difluoroethyl, 2,2,2-trifluoroethyl, perfluoroethyl, 2-fluoro-2-methylpropyl, and 3,3,3-trifluoropropyl.

The term "heteroaryl," as used herein, refers to an aromatic monocyclic ring or an aromatic bicyclic ring system. The aromatic monocyclic rings are five or six membered rings containing at least one heteroatom independently selected from the group consisting of N, O and S (e.g., 1, 2, 3, or 4 heteroatoms independently selected from N, O, and S). The five membered aromatic monocyclic rings have two double bonds and the six membered six membered aromatic monocyclic rings have three double bonds. The bicyclic heteroaryl groups are exemplified by a monocyclic heteroaryl ring that is fused to an aryl group, as defined herein, or a monocyclic heteroaryl group, as defined herein. Representative examples of heteroaryl include, but are not limited to, indolyl, pyridinyl (including pyridin-2-yl, pyridin-3-yl, pyridin-4-yl), pyrimidinyl, pyrazinyl, pyridazinyl, pyrazolyl, pyrrolyl, benzopyrazolyl, 1,2,3-triazolyl, 1,2,4-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, furanyl, oxazolyl, isoxazolyl, 1,2,4-triazinyl, 1,3,5-triazinyl, benzimidazolyl, benzothiazolyl, benzoxazolyl, benzoxadiazolyl, benzothienyl, benzofuranyl, isobenzofuranyl, purinyl, isoindolyl, quinoxalinyl, indazolyl, quinazolinyl, isoquinolinyl, quinolinyl, imidazo[1,2-a]pyridinyl, naphthyridinyl, and pyridoimidazolyl.

The term "heterocycle" or "heterocyclic," as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), azabicyclo[3.1.0]hexanyl (including 3-azabicyclo[3.1.0]hexan-3-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1 3,7]decane), and oxa-adamantane (2-oxatricyclo[3.3.1.1 3,7]decane). The monocyclic, bicyclic, and tricyclic heterocycles are connected to the parent molecular moiety through any carbon atom or any nitrogen atom contained within the rings.

The term "substituent" refers to a group substituted on an atom of the indicated group. When a group or moiety can be substituted, the term "substituted" indicates that one or more (e.g., 1, 2, 3, 4, 5, or 6; in some embodiments 1, 2, or 3; and in other embodiments 1 or 2) hydrogens on the group indicated in the expression using "substituted" can be replaced with a selection of recited indicated groups or with a suitable group known to those of skill in the art (e.g., one or more of the groups recited below). Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

As used herein, the term "quantum dot" refers to a nanoparticle of one or more semiconductor materials in which electron (and/or exciton) propagation is confined in three spatial dimensions. Non-limiting examples of quantum dot materials include CdSe, CdS, ZnSe, ZnS, PbS, PbSe, CuInS, CuS, lead halide perovskites, and combinations thereof.

The following abbreviations are used throughout the specification: d.r. is diastereomeric ratio; r.r. is regioselective ratio; HH is head-to-head; HT is head-to-tail; EnT is energy transfer; TT is triplet-triplet; and QD is quantum dot.

DETAILED DESCRIPTION

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Figure 1B:
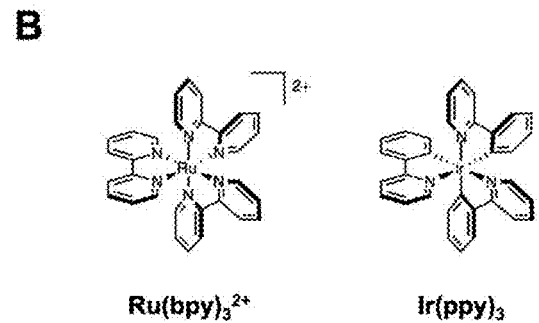
Figure 1B:
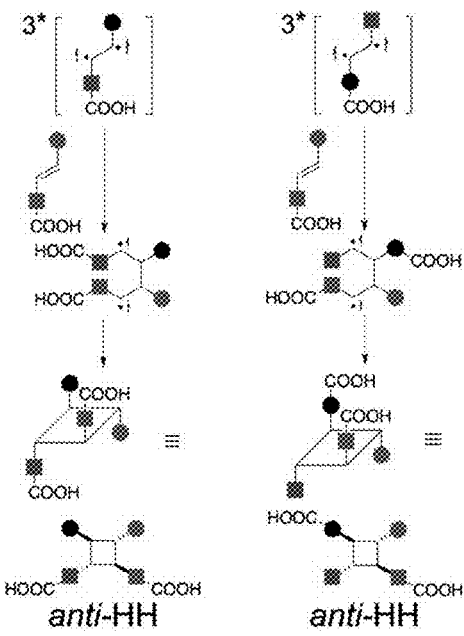

Disclosed herein are methods in which quantum dots (QDs), such as CdSe quantum dots, are used as visible light absorbers, triplet exciton donors, and self-assembly scaffolds to drive homo- and hetero-intermolecular [2+2] photocycloadditions of 4-vinylbenzoic acid derivatives. CdSe QDs can donate energy to triplet states of organic molecules from triplet-like excitonic "dark" states, which lie <20 meV below their optically active "bright states." A QD's triplet energy is tunable via size-dependent quantum confinement. The size of the QD can be adjusted to selectively sensitize only one reagent olefin within a mixture, and thereby achieve efficient hetero-intermolecular couplings. The QD catalytic systems may exhibit up to 98% switchable (between HH and HT) regioselectivity with up to 98% diastereoselectivity for the previously minor syn-HH or syn-HT configurations of the adducts (FIGS. 1A-B). The diastereomeric ratios (d.r.) achieved are generally a factor of 5-10 higher than those reported with all other triplet sensitizers for similar systems (see, e.g., Lei et al. *Angew. Chem. Int. Ed.* 56, 15407-15410 (2017), and Pagire et al. *Chem. Commun.* 53, 12072-12075 (2017)).

Figure 1C:
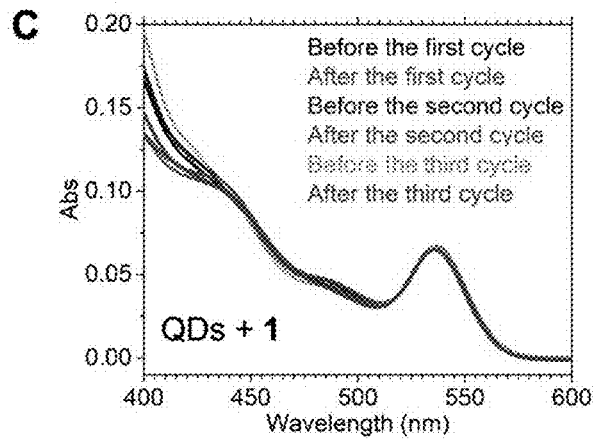

The Examples include details of synthesis and chemical analysis. The QDs do not etch, aggregate, or otherwise degrade for at least three 48 h reaction cycles (FIG. 1C). The QD catalysts can be readily separated from reaction mixtures through addition of methanol and centrifugation, and the QDs can be reused with no detectable decline in catalytic activity.

Figure 1D:
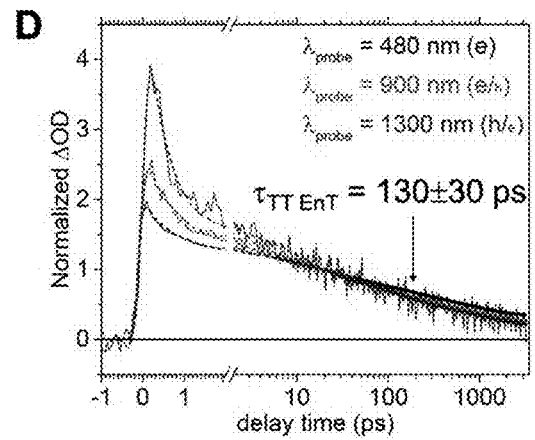

Through transient absorption spectroscopy, coincident decays of the photoexcited electron and hole of the QD are observed when the substrate is present (FIG. 1D). This result indicates that they are extracted from the QD as an electron-hole pair, and that the reaction is energy-transfer (EnT) initiated rather than redox-initiated (and specifically TT EnT-initiated, since the singlet excited states of all substrates are too high-energy to access). The coupling yields of all reactions are ≥10× lower when both substrates are not functionalized with carboxylate groups to reversibly bind to the QD (Scheme 1), indicating that the reaction occurs at the surface of the particle. Carboxylates are "medium-strength" ligands for the surfaces of CdSe ($k_{self-exchange}$~500 s$^{-1}$), so coupled products desorb from the QD surface to make room for new substrates.

Figure 2:
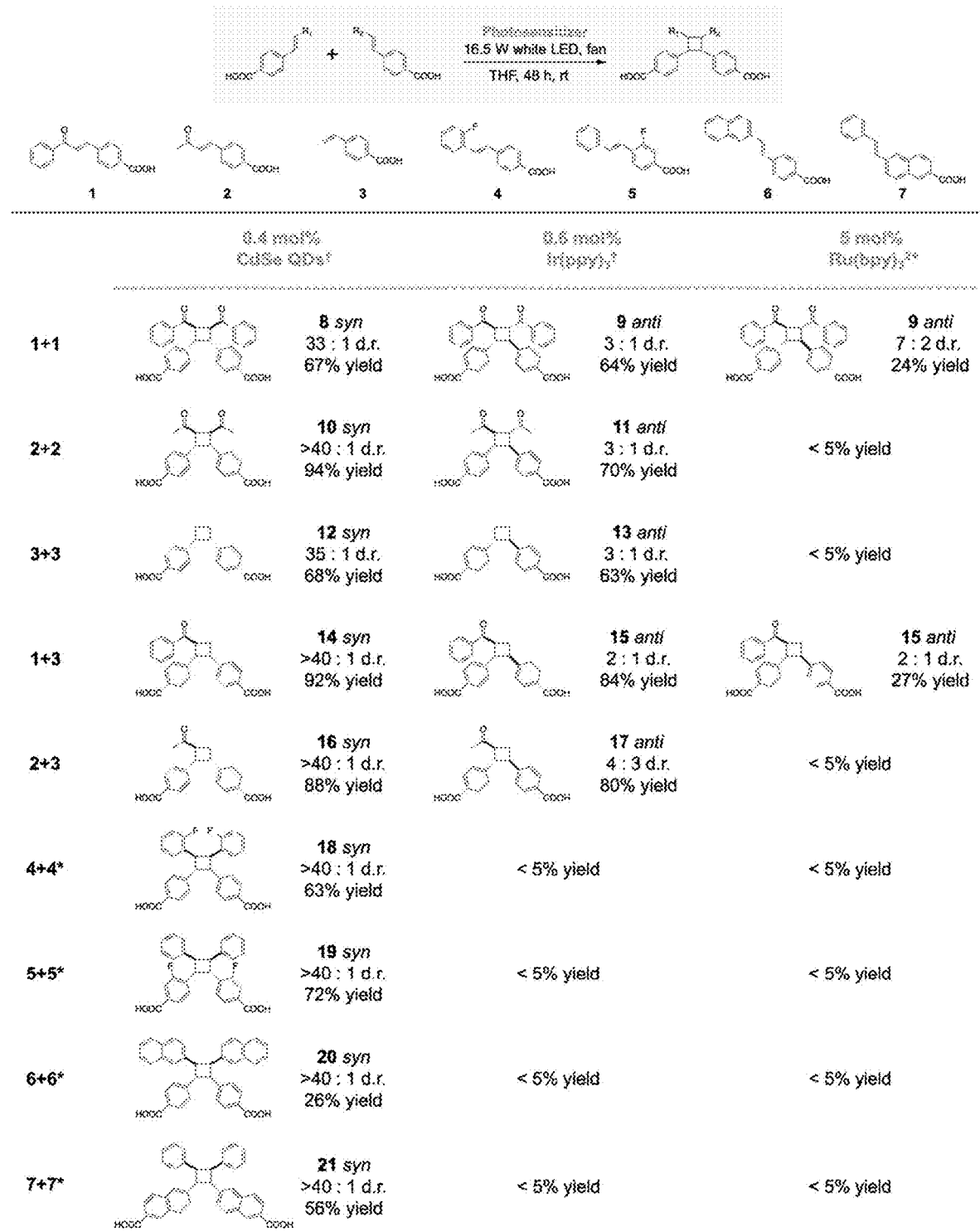
FIG. 2 shows conditions and product distributions of the homo- and hetero-[2+2] photocycloadditions of Compounds 1-7 with CdSe QDs and molecular photosensitizers. The yields listed are the isolated yields of the diastereomers drawn for QD systems (remaining mass =starting material and its cis-isomer; zero HT product) and the NMR yields of the regioisomers drawn for Ir(ppy)$_3$ and Ru(bpy)$_3^{2+}$ systems (remaining mass=starting material and its cis-isomer, minor unidentified side products).

FIG. 2 shows a set of [2+2] photocycloadditions of 4-vinylbenzoic acid and derivatives that demonstrate the activity and diastereoselectivity of the CdSe QD photocatalyst when directly compared to tris(2,2'-bipyridine)ruthenium(II) (Ru(bpy)$_3^{2+}$) or tris(2-phenylpyridinato)iridium (III) (Ir(ppy)$_3$) ("molecular complexes"), which have been used to perform similar reactions. The yields listed are the isolated yields of the diastereomers drawn for QD systems (remaining mass≡starting material and its cis-isomer; zero HT product) and the NMR yields of the regioisomers drawn for Ir(ppy)$_3$ and Ru(bpy)$_3^{2+}$ systems (remaining mass≡starting material and its cis-isomer, plus minor unidentified side products) (for further details, see the Examples). Reactions of Compound 1 were illuminated with >455 nm light so as not to excite the substrate directly. In FIG. 2, as noted by the †, listed loadings are for homocycloadditions; catalyst loadings for heterocycloadditions are 1.2 mol % QDs and 1.9 mol % molecular sensitizers.

The QD systems can generate syn products with d.r.>30:1, while the molecular complexes prefer anti products with much lower selectivity (d.r.<3:1). The syn stereochemistry of the QD products is verified by X-ray crystallography of Compound 8 (FIG. 5) and NOESY NMR spectroscopy of all products. For the heterocoupling of Compound 3 and either Compound 1 or Compound 2, the QDs produce syn products with d.r.>40:1, while the molecular complexes prefer anti products with d.r.<2:1. For the stilbene derivatives (Compounds 4-7), cycloadditions catalyzed by the molecular complexes do not occur with measurable yield, probably because of the known fast cis/trans isomerization of the excited-state substrates; a high concentration of cis isomers in the crude reaction mixtures was observed after illumination. QDs, in contrast, photocatalyze reactions with excellent coupling yields, either, we propose, by accelerating the coupling step through co-localization of substrates or by slowing the isomerization by tethering the substrates on the QD surface.

The selective production of the kinetically disfavored syn configuration by the QDs, even in the case of two different coupling partners, is remarkable considering that the only templating chemistry is the reversible association of a carboxylate on the substrate with Cd$^{2+}$ on the QD surface. The ability of intermolecular π-π interactions among rigid olefins to promote syn stereochemistry in solid-state reactions suggests that these same non-covalent interactions are responsible for the syn selectivity in the QD system (FIG. 1A).

FIG. 3 illustrates the role of tunable QD size in achieving heterocoupling (over homocoupling) through selective TT EnT. The difficulty in controlling competition between homo- and heterocoupling has limited the scope of previous heterocouplings to substrates with large triplet energy differences. In this case, the triplet energies of Compound 1 and Compound 3 (2.25 eV and 2.51 eV respectively) are close enough such that Ir(ppy)$_3$ indiscriminately sensitizes both substrates (FIG. 3B), resulting in 23% of Compound 3 producing the undesired homocoupled product Compound 9. In contrast, 1.4 nm CdSe QDs perform selective TT EnT to Compound 1 without sensitizing Compound 3, yielding highly efficient heterocoupling (92% yield of Compound 14) with <5% of Compound 3 participating in homocoupling. The comparatively unselective performance of the higher-energy 1.0 nm CdSe QDs illustrates that selective energetic overlap with a specific substrate may be the key to efficient heterocoupling. In FIG. 3, the yields listed are for the regioisomers indicated (drawn in A); the remaining mass is exclusively starting materials and the cis-isomer of Compound 1 for the QD systems, and the same plus minor unidentified side products for the molecule-catalyzed reactions.

Figures 4A, 4B:
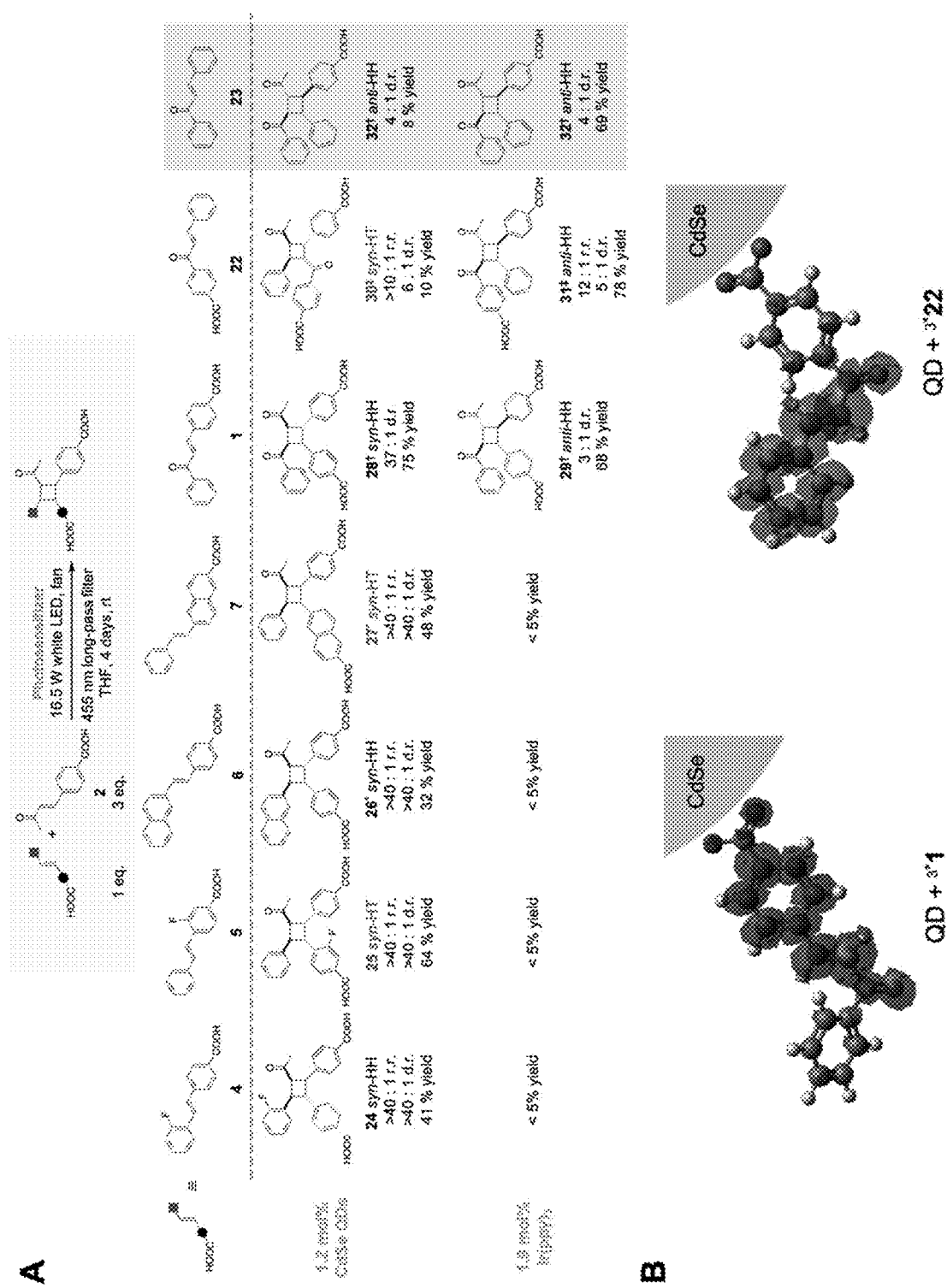
FIGS. 4A-4B show: (A) conditions and product distributions for the [2+2] photocycloadditions of Compound 2 and Compound 1, 4, 5, 6, 7, 22, and 23. When Compound 2 is coupled with Compound 23, which has no carboxylic acid, the distribution of regioisomer products matches that of Ir(ppy)$_3$. The yields listed for QD reactions are isolated yields for the diastereomers drawn (the major product), except for the reaction with the control substrate Compound 23. The yields listed for Ir(ppy)$_3$ and Ru(bpy)$_3^{2+}$ systems are the NMR yields of the regioisomers drawn. The remaining mass of the coupling with Compound 2 and Compound 22 is starting materials and their cis-isomers (>72%), the HH regioisomer, and the homocycloaddition products of both substrates for the QD system, and is the same plus minor unidentified side products for the Ir(ppy)$_3$ system. *Reactions were catalyzed with 2.4 mol % QDs. The reaction was illuminated with a blue LED for 4 days. ‡The reaction was illuminated with a blue LED; (B) Transition densities for the first triplet excited states for Compound 1 and Compound 22 calculated using open-shell time-dependent density functional theory (TD-DFT).

FIG. 4 demonstrates the >90% tunable regioselectivity achievable for hetero-[2+2] photocycloadditions using the CdSe QD system. Most notably this system produces the disfavored heterocoupled HT regioisomer Compounds 25, 27, and 30. For untemplated reactions, i.e., those photosensitized by Ir(ppy)$_3$ or by QDs but where one substrate does not have a carboxylic acid substituent (gray shaded area), formation of the HH regioisomer is strongly favored through benzylic stabilization of the corresponding 1,4-diradical intermediate. In order to access the syn-HT heterocoupled products (Compounds 25, 27, and 30), which have never been formed as a major product of [2+2] photocycloaddition, the regioselectivity of the QD-catalyzed reactions was tuned through the position of the carboxylate on each substrate (FIG. 4A). For coupling of Compounds 1, 4, 6 and 2, perfect HH regioselectivity was achieved with no HT products detected. When the carboxylate moiety is relocated to the opposite side of the substrate (Compounds 4 vs. 4, 7 vs. 6, 22 vs. 1), the observed regioselectivity of the QD catalyst switches entirely, providing the HT product for the heterocoupling of Compounds 5, 7 and 2 with r.r.>10:1, and 22 and 2 with r.r.>10:1. The syn diastereoselectivity is preserved in these regioselective reactions: the heterocoupled products (Compounds 24-28) have d.r.>37:1 and Compound 30 has d.r.>10:1.

In contrast, the Ir(ppy)$_3$ sensitizer produces the HH configuration as the major product regardless of whether Compound 2 is coupled with Compound 22 or Compound 1. The weak preference for the anti diastereoisomer remains in Compounds 29 and 31 with d.r. up to 5:1. The loss of regioselectivity upon removing the carboxylate from one of the substrates (Compound 23) shows that the QD system achieves regioselective heterocoupling through pre-arrangement of substrates at the QD surface, a manner entirely independent of electronics of the reactive olefin. Moreover, the heterocoupling of stilbenes (Compound 4 to Compound 7 with Compound 2) by molecular substrates produces no measurable yield because of the same competing isomerization pathway described in reference to FIG. 2.

The low overall yield of the QD-catalyzed reaction between Compounds 2 and 22 is not due to side products (72% of the remaining yield can be accounted for by starting material), but appears to be limited by the location of triplet acceptor orbitals of the substrate (FIG. 4B). For Compound 1, the triplet excited state transition (S$_0$→T$_1$) has good spatial overlap with the binding group of the substrate, and therefore good electronic coupling with the QD. For Compound 22, there is a spatial gap between the QD surface and the triplet density; this gap makes TT EnT inefficient.

Accordingly, in some embodiments, disclosed herein is a method of synthesizing a substituted cyclobutane compound, the method comprising:
(a) providing a compound of formula (I) and a compound of formula (II):

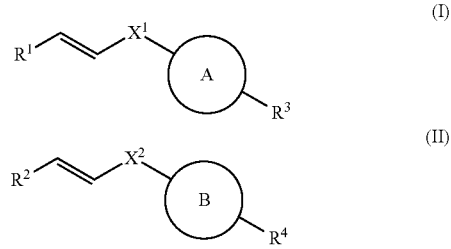

wherein:
X$^1$ and X$^2$ are each independently selected from a bond and —C(O)—;

R$^1$ and R$^2$ are each independently selected from hydrogen, aryl, —C(O)-alkyl, and —C(O)-aryl; and
R$^3$ and R$^4$ are each independently selected from —COOH and —NH$_2$;
A and B are each independently selected from aryl;
wherein the alkyl, cycloalkyl, aryl, heterocyclyl, and heteroaryl are optionally substituted;
(b) providing a plurality of quantum dots;
(c) combining the compound of formula (I), the compound of formula (II), and the quantum dot in a solvent to provide a mixture; and
(d) subjecting the mixture to irradiation,
to thereby synthesize the substituted cyclobutane compound.

In some embodiments, X$^1$ is a bond. In some embodiments, X$^1$ is —C(O)—. In some embodiments, X$^2$ is a bond. In some embodiments, X$^2$ is —C(O)—. In some embodiments, X$^1$ is a bond and X$^2$ is a bond.

In some embodiments, R$^1$ and R$^2$ are each independently selected from hydrogen, phenyl, naphthyl, acetyl (—COCH$_3$), and benzoyl (—C(O)Ph). In some embodiments, the phenyl group is unsubstituted. In some embodiments, the phenyl group is further substituted with one or more substituents (e.g., alkyl, alkenyl, alkynyl, halogen, haloalkyl, cycloalkyl, cycloalkenyl, aryl, —OR, —C(O)R, —C(O)OR, —NRR', —C(O)NRR', and —NR'C(O)R; wherein each R is independently selected from alkyl, alkenyl, alkynyl, cycloalkyl, cycloalkenyl, aryl, heteroaryl, and heterocyclyl; and each R' is independently selected from hydrogen, alkyl, alkenyl, alkynyl, cycloalkyl, cycloalkenyl, aryl, heteroaryl, and heterocyclyl). In some embodiments, the phenyl group is further substituted with one or more substituents selected from C$_1$-C$_3$ alkyl, C$_2$-C$_3$ alkenyl, C$_2$-C$_3$ alkynyl, halo, C$_1$-C$_3$ haloalkyl, C$_3$-C$_6$ cycloalkyl, C$_1$-C$_3$-alkoxy, C$_1$-C$_3$-alkylamino, di-(C$_1$-C$_3$-alkyl)amino, and —C(O)O—(C$_1$-C$_3$-alkyl).

In some embodiments, A is a phenyl group. In some embodiments, A is a naphthyl group. In some embodiments, B is a phenyl group. In some embodiments, B is a naphthyl group. In some embodiments, A and B are both phenyl. In some embodiments, A and B are unsubstituted (aside from the R$^3$ and R$^4$ groups). In some embodiments, A and B are further substituted with 1 substituent selected from alkyl, alkenyl, alkynyl, halogen, haloalkyl, cycloalkyl, cycloalkenyl, aryl, —OR, —C(O)R, —C(O)OR, —NRR', —C(O)NRR', and —NR'C(O)R; wherein each R is independently selected from alkyl, alkenyl, alkynyl, cycloalkyl, cycloalkenyl, aryl, heteroaryl, and heterocyclyl; and each R' is independently selected from hydrogen, alkyl, alkenyl, alkynyl, cycloalkyl, cycloalkenyl, aryl, heteroaryl, and heterocyclyl. In some embodiments, A and B are further substituted with 1 substituent selected from C$_1$-C$_3$ alkyl, C$_2$-C$_3$ alkenyl, C$_2$-C$_3$ alkynyl, halo, C$_1$-C$_3$ haloalkyl, C$_3$-C$_6$ cycloalkyl, C$_1$-C$_3$-alkoxy, C$_1$-C$_3$-alkylamino, di-(C$_1$-C$_3$-alkyl)amino, and —C(O)O—(C$_1$-C$_3$-alkyl). In some embodiments, A and B are further substituted with 1 substituent selected from C$_1$-C$_3$ alkyl and halo (e.g., fluoro).

In some embodiments, A is an unsubstituted phenyl group (aside from the R$^3$ group). In some embodiments, A is an unsubstituted naphthyl group (aside from the R$^3$ group). In some embodiments, A is a phenyl group substituted with fluoro.

In some embodiments, B is an unsubstituted phenyl group (aside from the R$^4$ group). In some embodiments, B is an unsubstituted naphthyl group (aside from the R$^4$ group). In some embodiments, B is a phenyl group substituted with fluoro.

In some embodiments, $R^3$ and $R^4$ are both —COOH.

In some embodiments, the compound of formula (I) is a compound of formula (Ia), and the compound of formula (II) is a compound of formula (IIa):

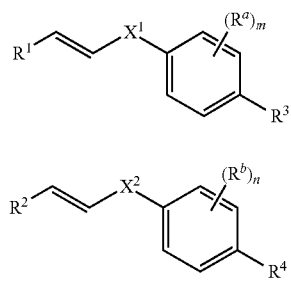

wherein:

$R^a$ and $R^b$ are each independently selected from alkyl, alkenyl, alkynyl, halogen, haloalkyl, cycloalkyl, cycloalkenyl, aryl, —OR, —C(O)R, —C(O)OR, —NRR', —C(O)NRR', and —NR'C(O)R; wherein each R is independently selected from alkyl, alkenyl, alkynyl, cycloalkyl, cycloalkenyl, aryl, heteroaryl, and heterocyclyl; and each R' is independently selected from hydrogen, alkyl, alkenyl, alkynyl, cycloalkyl, cycloalkenyl, aryl, heteroaryl, and heterocyclyl;

m is 0, 1, or 2; and n is 0, 1, or 2.

In compounds of formula (Ia) and (IIa), the groups $R^1$, $R^2$, $R^3$, $R^4$, $X^1$, and $X^2$ have the same meanings as those set forth for compounds of formula (I) and (II).

In some embodiments, m is 0 or 1. In some embodiments, n is 0 or 1. In some embodiments, m is 0 or 1 and n is 0 or 1, and $R^a$ and R are each independently selected from the group consisting of $C_1$-$C_3$ alkyl, $C_2$-$C_3$ alkenyl, $C_2$-$C_3$ alkynyl, halo, $C_1$-$C_3$ haloalkyl, $C_3$-$C_6$ cycloalkyl, $C_1$-$C_3$-alkoxy, $C_1$-$C_3$-alkylamino, di-($C_1$-$C_3$-alkyl)amino, and —C(O)O—($C_1$-$C_3$-alkyl). In some embodiments, $R^a$ and $R^b$ are each independently selected from $C_1$-$C_3$ alkyl and halo (e.g., fluoro).

In some embodiments, the compound of formula (I) is a compound of formula (Ib), and the compound of formula (II) is a compound of formula (IIb):

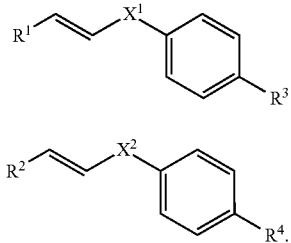

In compounds of formula (Ib) and (IIb), the groups $R^1$, $R^2$, $R^3$, $R^4$, $X^1$, and $X^2$ have the same meanings as those set forth for compounds of formula (I) and (II).

In some embodiments, the compound of formula (I) and the compound of formula (II) are independently selected from the group consisting of:

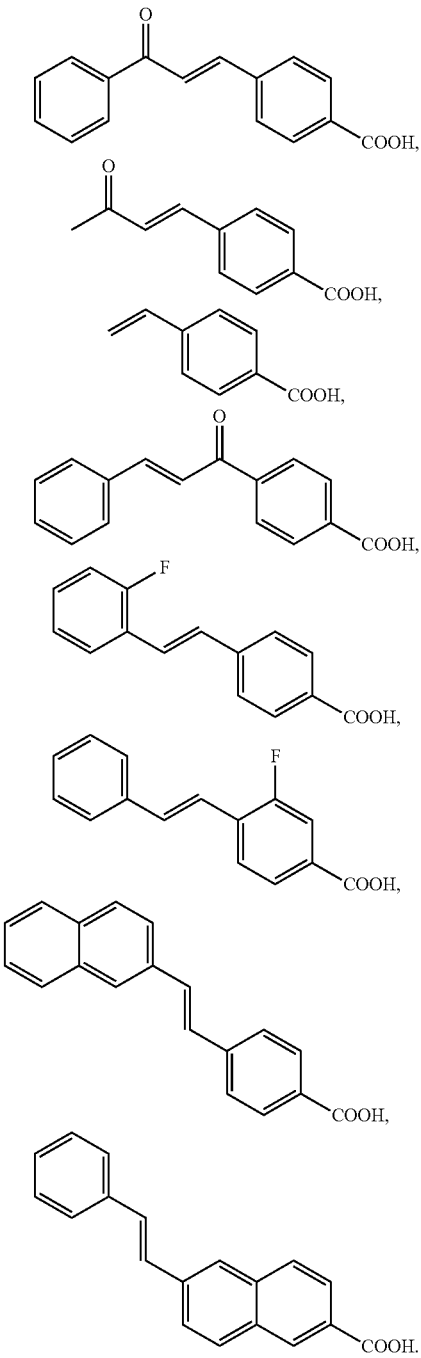

In some embodiments, the compound of formula (I) and the compound of formula (II) are the same. In some embodiments, the compound of formula (I) and the compound of formula (II) are different.

Compounds of formula (I) and formula (II) may be commercially available or may be synthesized by methods known to those skilled in the art. For example, compounds may be commercially available from Sigma-Aldrich (St. Louis, Mo.).

In some embodiments, the substituted cyclobutane compound is a compound of formula (III):

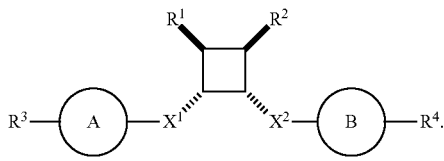
(III)

In compounds of formula (III), the groups $R^1$, $R^2$, $X^1$, $X^2$, A, B, $R^3$, and $R^4$ have the same meanings as those described above for compounds of formula (I) and formula (II).

In some embodiments, the compound of formula (III) is a compound of formula (IIIa):

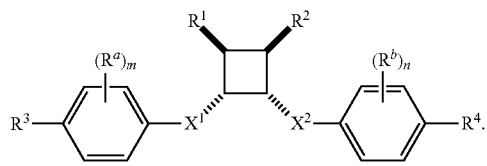
(IIIa)

In compounds of formula (IIIa), the groups $R^1$, $R^2$, $R^3$, $R^4$, $X^1$, $X^2$, $R^a$, $R^b$, m, and n have the same meanings as those described above for compounds of formula (Ia) and formula (IIa).

In some embodiments, the compound of formula (III) is a compound of formula (IIIb):

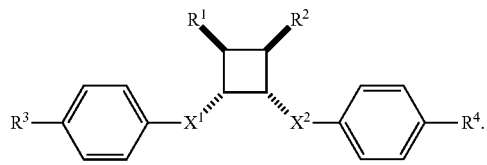
(IIIb)

In compounds of formula (IIIb), the groups $R^1$, $R^2$, $R^3$, $R^4$, $X^1$, and $X^2$ have the same meanings as those described above for compounds of formula (Ib) and formula (IIb).

In some embodiments, the compound of formula (III) is synthesized with a diastereomeric ratio of greater than 10:1 compared to a compound of formula (IV):

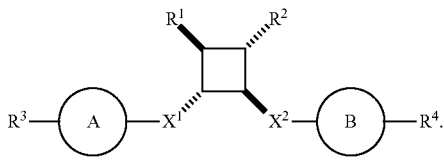
(IV)

The compound of formula (III) is the syn diastereomer, and the compound of formula (IV) is the anti diastereomer. As described herein, the disclosed methods provide up to 98% diastereoselectivity for the syn-cyclobutane products. For example, in some embodiments, the compound of formula (III) is synthesized with a diastereomeric ratio of greater than 10:1, greater than 15:1, greater than 20:1, greater than 25:1, greater than 30:1, greater than 35:1, or greater than 40:1, compared to a compound of formula (IV).

In compounds of formula (IV), the groups $R^1$, $R^2$, $X^1$, $X^2$, A, B, $R^3$, and $R^4$ have the same meanings as those described above for compounds of formula (I) and formula (II).

In some embodiments, the compound of formula (IV) is a compound of formula (IVa):

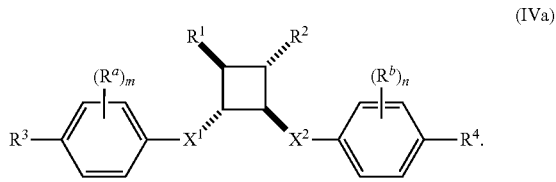
(IVa)

In compounds of formula (IVa), the groups $R^1$, $R^2$, $R^3$, $R^4$, $X^1$, $X^2$, $R^a$, $R^b$, m, and n have the same meanings as those described above for compounds of formula (Ia) and formula (IIa).

In some embodiments, the compound of formula (IV) is a compound of formula (IVb):

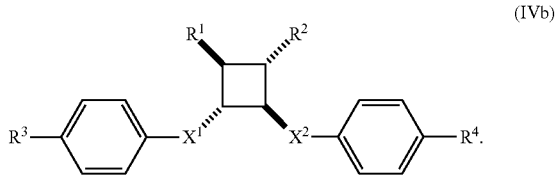
(IVb)

In compounds of formula (IVb), the groups $R^1$, $R^2$, $R^3$, $R^4$, $X^1$, and $X^2$ have the same meanings as those described above for compounds of formula (Ib) and formula (IIb).

In some embodiments, the compound of formula (III) is synthesized with a ratio of greater than 10:1 compared to a compound of formula (V):

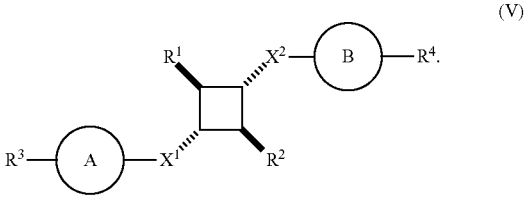
(V)

The compound of formula (V) is a regioisomer of the compound of formula (III). For example, the compound of formula (III) may be synthesized with a ratio of greater than 10:1, greater than 15:1, greater than 20:1, greater than 25:1, greater than 30:1, greater than 35:1, or greater than 40:1, compared to a compound of formula (V).

In compounds of formula (V), the groups $R^1$, $R^2$, $X^1$, $X^2$, A, B, $R^3$, and $R^4$ have the same meanings as those described above for compounds of formula (I) and formula (II).

In some embodiments, the compound of formula (V) is a compound of formula (Va):

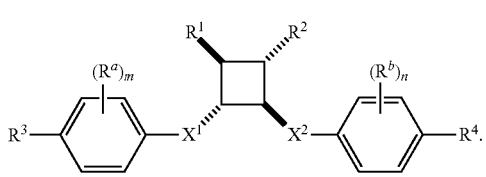

(Va)

In compounds of formula (Va), the groups $R^1$, $R^2$, $R^3$, $R^4$, $X^1$, $X^2$, $R^a$, $R^b$, m, and n have the same meanings as those described above for compounds of formula (Ia) and formula (IIa).

In some embodiments, the compound of formula (V) is a compound of formula (Vb):

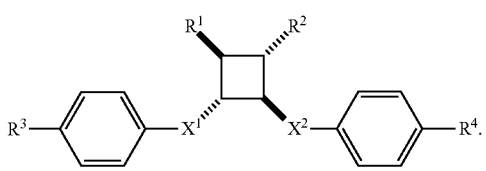

(Vb)

In compounds of formula (Vb), the groups $R^1$, $R^2$, $R^3$, $R^4$, $X^1$, and $X^2$ have the same meanings as those described above for compounds of formula (Ib) and formula (IIb).

In some embodiments, the disclosure provides a compound, wherein the compound is any compound of formula (I), (II), (III), (IV), or (V) described herein. In some embodiments, the disclosure provides a compound of formula (III) described herein.

A variety of quantum dots may be used in the reactions. For example, the quantum dots may be CdSe, CdS, ZnSe, ZnS, PbS, PbSe, CuInS, CuS or lead halide perovskite quantum dots, or mixtures thereof. In some embodiments, the quantum dots are selected from CdSe quantum dots and CdS quantum dots. In some embodiments, the quantum dots are CdSe quantum dots. Quantum dots can be purchased from commercial suppliers, or can be prepared by methods known to those skilled in the art. For example, methods for preparing quantum dots include hot-injection methods, heat-up methods, cluster-assisted methods, microwave-assisted methods, and continuous-flow methods. In particular, quantum dots can be prepared according to: Flamee et al., "Fast, High Yield, and High Solid Loading Synthesis of Metal Selenide Nanocrystals," Chem. Mater. 25, 2476-2483 (2013); Pu et al., "Colloidal Synthesis of Semiconductor Quantum Dots toward Large-Scale Production: A Review," Ind. Eng. Chem. Res. 57, 1790-1802 (2018); and Kershaw et al., "Narrow bandgap colloidal metal chalcogenide quantum dots: synthetic methods, heterostructures, assemblies, electronic and infrared optical properties," Chem. Soc. Rev., 42, 3033-3087 (2013); each of which is herein incorporated by reference in its entirety.

In some embodiments, the quantum dots have an average radius of 0.8 to 2.0 nm. In some embodiments, the quantum dots have an average radius of 1.0 to 1.4 nm. For example, the quantum dot can have an average radius of 0.8 nm, 0.9 nm, 1.0 nm, 1.1 nm, 1.2 nm, 1.3 nm, 1.4 nm, 1.5 nm, 1.6 nm, 1.7 nm, 1.8 nm, 1.9 nm, or 2.0 nm.

In some embodiments, the quantum dots further comprise capping molecules on the surface of the quantum dots. Inclusion of capping molecules, such as surfactants or other ligands, can help tune the properties of the QDs, and in particular can help prevent agglomeration of the QDs in solution. The capping molecule may include an amine, a carboxylate, a thiol, or other functional group that binds to the QD surface. Exemplary capping groups are described in, for example, Harris et al. "Electronic Processes within Quantum Dot-Molecule Complexes," Chem. Rev. 116, 12865-12919 (2016), which is herein incorporated by reference in its entirety. In some embodiments, the capping molecule is a fatty acid. In some embodiments, the capping molecule is oleic acid.

The reaction is generally carried out in a solvent, or a mixture of solvents. In some embodiments, the solvent is selected from tetrahydrofuran, toluene, ethyl acetate, dichloromethane, chloroform, an ether (e.g., diethyl ether), or mixtures thereof. In some embodiments, the solvent is tetrahydrofuran.

In some embodiments, the method comprises irradiating the mixture for 24-72 hours. For example, the mixture may be irradiated for about 24 hours, about 36 hours, about 48 hours, about 60 hours, or about 72 hours. In some embodiments, the method comprises irradiating the mixture for 48 hours. When conducting the irradiation, a longpass filter may be used to prevent excitation of the substrate. For example, the method may comprise irradiating the mixture using a 16.5 W white-light LED with a 455 nm longpass filter. The method may comprise irradiating the mixture using a blue LED (emission centered at 467 nm).

In some embodiments, the quantum dots are present in the mixture in an amount of 0.2 mol % to 2.0 mol %. In some embodiments, the quantum dots are present in the mixture in an amount of 0.4 mol % to 1.2 mol %. For example, the quantum dots may be present in the mixture in an amount of 0.2 mol %, 0.3 mol %, 0.4 mol %, 0.5 mol %, 0.6 mol %, 0.7 mol %, 0.8 mol %, 0.9 mol %, 1.0 mol %, 1.1 mol %, 1.2 mol %, 1.3 mol %, 1.4 mol %, 1.5 mol %, 1.6 mol %, 1.7 mol %, 1.8 mol %, 1.9 mol %, or 2.0 mol %.

In some embodiments, the reactions are carried out in solution, with the QDs, starting materials (compounds of formula (I) and (II)), solvents, etc. all included together in a reaction vessel such as a flask, beaker, or chemical reactor (e.g., a research reactor, a commercial reactor, an industrial reactor, or the like). In some embodiments, the QDs are adhered to a surface (e.g., a reaction card, a plate, the interior surface of a volume (e.g., vial, chemical reactor, etc.), a chip, etc. and the starting materials (e.g., compounds of formula (I) and (II)) and any other components are passed over the surface.

In some embodiments, the reactor is of the appropriate scale for the particular application (e.g., <1 L, 1 L, 2 L, 5 L, 10 L, 20 L, 50 L 100 L, 200 L, 500 L, 1000 L, or more, or ranges therebetween). In some embodiments, a chemical reactor is a batch-style reactor, tank reactor, continuous stirred-tank reactor (CSTR), a plug flow reactor (e.g., with QDs adhered to the internal surface and liquid reagents passed through), a semi-batch reactor, etc. In some embodiments, a reactor comprises a window or translucent/transparent portion to allow illumination with the appropriate wavelength of light. In some embodiments, a reactor is transparent to the appropriate wavelength of light. In some embodiments, a reactor comprises an internal light source for illumination.

In some embodiments, the method further comprises separating the quantum dots from the substituted cyclobutane compound. Any suitable separation method may be used. In some embodiments, the quantum dots are separated from the reaction mixture by centrifugation. The separated QDs can be resuspended in solvent for use in another reaction cycle.

The quantum dots remain stable throughout the course of the reaction and can be used for multiple reaction cycles without loss of activity. In some embodiments, the quantum dots do not etch, aggregate, or otherwise degrade for at least 2, 3, 4, 5, 6, 7, 8, 9, or 10 reaction cycles. Degradation of QDs can be monitored, for example, by monitoring the UV-vis absorption spectra.

The reaction products (e.g., compounds of formula (III)) may be isolated and purified by methods known to those skilled in the art of organic synthesis. Examples of conventional methods for isolating and purifying compounds include chromatography on solid supports such as silica gel, alumina, or silica derivatized with alkylsilane groups, by recrystallization, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

EXAMPLES

Materials.

Tetrahydrofuran was purified by elution through alumina as previously described (Pangborn et al. *Organometallics* 15, 1518-1520 (1996)). A 16.5-W (2050 lumens) Green Creative 58240 high output LED light bulb or a 34 W Kessil KSPR160-467 blue LED (emission centered at 467 nm) was used for all photochemical reactions, unless otherwise noted. Reverse-phase flash column chromatography was performed with Fluka 40-63 Å C18-reverse phase silica (230-240 mesh). HPLC grade methanol, water and acetonitrile were purchased from Sigma Aldrich and used as received. Ir(ppy)$_3$, Ru(bpy)$_3$(PF6)$_2$, methyl-THF and all other compounds were purchased from Sigma Aldrich and were used without further purification unless otherwise noted.

Characterization Methods.

The yields listed are isolated yields for all the QDs systems except Compound 30, and are NMR yields for all the molecular catalyst systems, as determined by $^1$H NMR analysis of the crude reaction mixtures compared with NMR spectra of the purified products. 3,4,5-trichloropyridine was used as an internal integration standard. Diastereomeric ratios for all compounds were determined by comparing relative intensities of $^1$H NMR signals of the products in unpurified reaction mixtures. $^1$H and $^{19}$F NMR data were acquired using a Bruker Neo 600 MHz spectrometer with QCI-F cryoprobe and $^{13}$C NMR data were acquired using a Bruker Avance III 500 MHz spectrometer with DCH cryoprobe, referenced to dimethyl sulfoxide-d$_6$ (2.5 ppm and 39.52 ppm, respectively for $^1$H and $^{13}$C). Preparative reverse phase HPLC was performed with C18 columns (Phenomenex Polar RP 150×21.20 mm; 4 μm and Agilent Poroshell C18 250×21.20 mm; 10 μm). UV-vis ground state absorption spectra were acquired using a Varian Cary 5000 spectrophotometer. Analytical LC-MS were performed on Bruker AmaZon X mass spectrometer connected to a LC using a C18 column (Thermo Hypersil BDS 50×3 mm; 5 μm). Steady-state emission spectra were acquired using a HORIBA Nanolog spectrofluorimeter equipped with the time-correlated single photon counting (TCSPC) module for measuring the phosphorescence lifetime.

Example 1

QD Catalyst Recycling Experiment

A 4 mL vial was charged with (E)-4-(3-oxo-3-phenyl-prop-1-en-1-yl)benzoic acid (Compound 1) (8.4 mg, 0.033 mmol, 1.0 equiv.) and 1.4 nm oleate-capped CdSe QDs (0.27 mL of 501 μM solution in hexanes, 0.132 μmol, 0.004 equiv.); the solvent was removed in vacuo. The vial was then transferred to a N$_2$ glove box, a magnetic stir bar was added, and the contents were dissolved in 1 mL of anhydrous THF. (Note: exposure of QDs to peroxide-contaminated THF causes QD degradation, so THF used with QDs should be regularly tested and stored in a glovebox.) The vial was sealed with a Teflon-lined cap, removed from the glovebox, and stirred under 16.5 W white-light LED irradiation for 48 h with a 455 nm longpass filter to prevent excitation of the substrate. Axial fans were employed to keep the sample at room temperature. After illumination, 14 mL of MeOH was added to the reaction mixture and the resulting QD precipitate was collected by centrifugation. The QD pellet was then transferred back to a N$_2$ glove box and redispersed in THF for use in another catalytic cycle. The yields reported in Table 1 were obtained by $^1$H NMR spectroscopic analysis of the crude reaction mixture relative to 3,4,5-trichloropyridine internal standard. The reported NMR yields represent the total yield of both the major and minor diastereomeric cycloadducts. A 10-μL aliquot of each reaction mixture was taken before and after each cycle and diluted by 50-fold to measure the ground state absorption spectra within a 1-cm quartz cuvette. QD catalysts exhibit no significant change in reactivity or selectivity for [2+2] homo-photocycloadditions of Compound 1 across three successive experiments reusing the same catalyst. The yields and d.r. values were determined by $^1$H NMR analysis of the unpurified reaction mixtures, and comparison with NMR spectra of Compounds 8 and 9. 3,4,5-trichloropyridine was used as an internal integration standard.

TABLE 1

QD catalyst recyclability

| Cycle | Yield of Homo-coupling | Starting Material and its cis-isomer | d.r. (syn:anti) |
|---|---|---|---|
| 1 | 67% | 32% | 34:1 |
| 2 | 69% | 30% | 40:1 |
| 3 | 65% | 35% | 37:1 |

As shown in Table 1, the QD catalysts exhibited no significant change in reactivity or selectivity for [2+2] homo-photocycloadditions of Compound 1 across three successive experiments reusing the same catalyst. The yields and d.r. values were determined by $^1$H NMR analysis of the unpurified reaction mixtures, and comparison with NMR spectra of Compounds 8 and 9. 3,4,5-trichloropyridine was used as an internal integration standard.

Example 2

Control Studies

Control studies were conducted with the following representative procedure. A 4 mL vial was charged with (E)-4-(3-oxo-3-phenylprop-1-en-1-yl)benzoic acid (Compound 1) (8.4 mg, 0.033 mmol, 1.0 equiv.) and 0.27 mL of 501 µM (0.132 µmol, 0.004 equiv.) 1.4 nm oleate-capped CdSe QDs in hexanes. The solvent was removed in vacuo. The vial was transferred to a N$_2$ glove box, a magnetic stir bar was added, and the contents were dissolved in 1 mL of anhydrous THF. (Note: the exposure of QDs to peroxide-contaminated THF causes QD degradation, so THF used with QDs should be regularly tested and stored in a glovebox.) The vial was sealed with a Teflon-lined cap and stirred under 16.5 W of white-light LED irradiation for 48 h with a 455 nm longpass filter to prevent excitation of the substrate. Axial fans were employed to keep the sample at room temperature. After illumination, 14 mL of MeOH was added to the reaction mixture and the resulting QD precipitate was collected by centrifugation. The supernatant was removed by pipette and dried under reduced pressure. The yields reported in Table 2 and Scheme 1 were obtained by $^1$H NMR spectroscopic analysis of the crude reaction mixture relative to 3,4,5-trichloropyridine internal standard. The NMR yields represent the total yield of both the major and minor diastereomeric cycloadducts. The yields in Table 2 were determined by $^1$H NMR analysis of the unpurified reaction mixtures, and comparison with NMR spectra of Compound 8. 3,4,5-trichloropyridine was used as an internal integration standard.

TABLE 2

Control Studies for QD-catalyzed [2 + 2] photocycloadditions of (E)-4-(3-oxo-3-phenylprop-1-en-1-yl)benzoic acid Compound 1.

| Entry | Photosensitizer | Note | Yield |
|---|---|---|---|
| 1 | None | — | <5% yield |
| 2 | CdSe QDs (0.4 mol %) | No light | <5% yield |
| 3 | CdSe QDs (0.4 mol %) | — | 67% |

Scheme 1. Control Studies for QD-catalyzed [2 + 2] Photocycloadditions of Substrates with and without a Carboxylate Group.

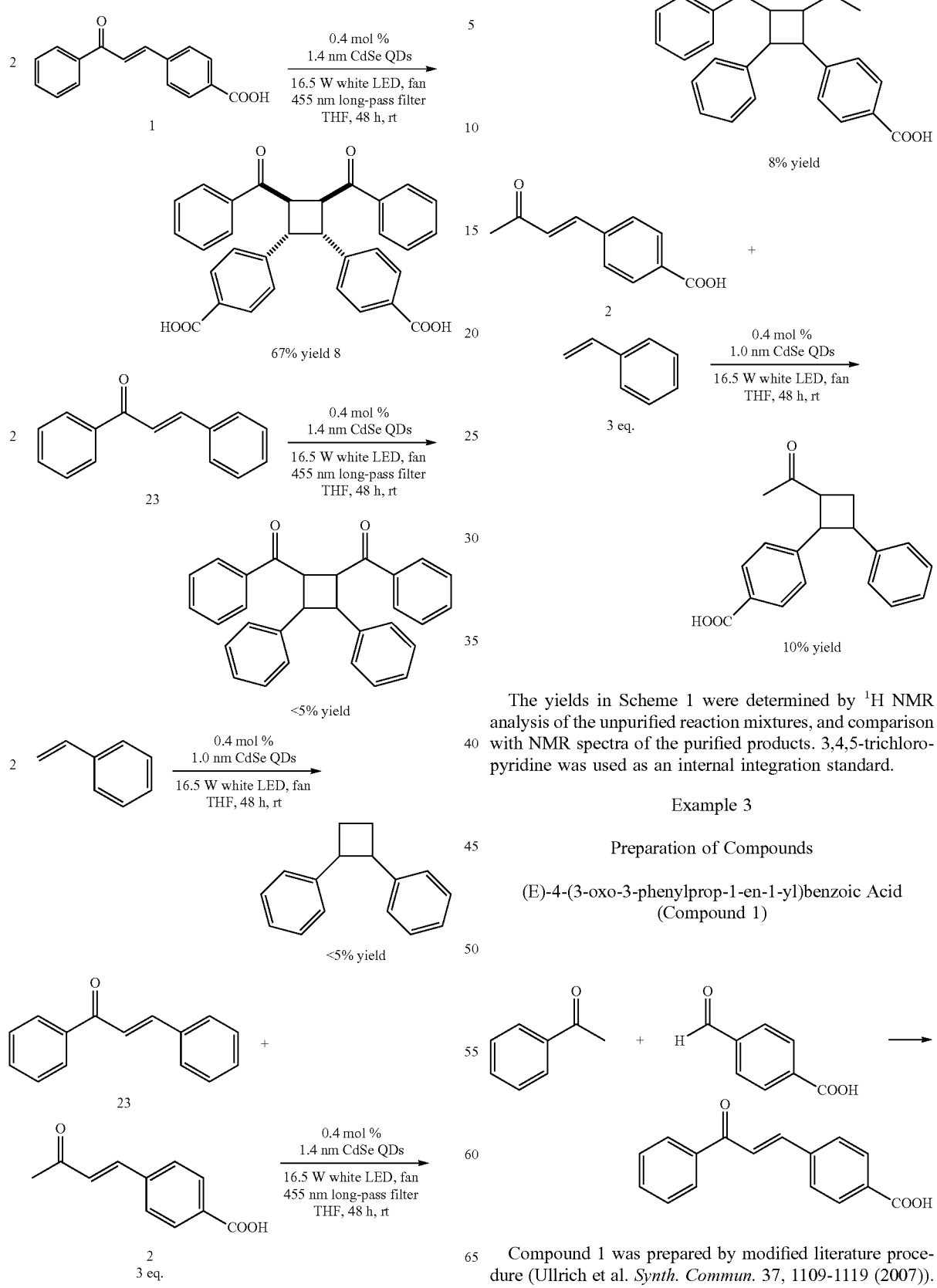

The yields in Scheme 1 were determined by $^1$H NMR analysis of the unpurified reaction mixtures, and comparison with NMR spectra of the purified products. 3,4,5-trichloropyridine was used as an internal integration standard.

Example 3

Preparation of Compounds (E)-4-(3-oxo-3-phenylprop-1-en-1-yl)benzoic Acid (Compound 1)

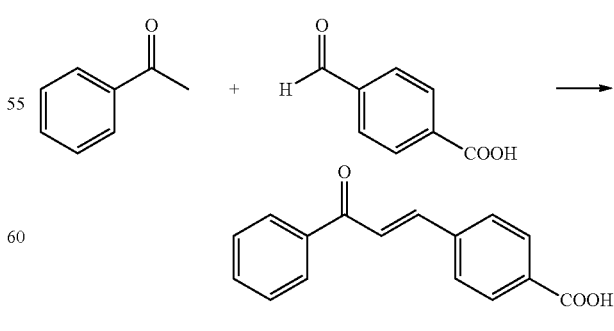

Compound 1 was prepared by modified literature procedure (Ullrich et al. *Synth. Commun.* 37, 1109-1119 (2007)). A 50 mL round-bottom flask was charged with acetophenone (500 mg, 4.16 mmol, 1.0 equiv.), 4-formylbenzoic acid (625 mg, 4.16 mmol, 1.0 equiv.), and EtOH (20 mL). KOH (700 mg, 12.48 mmol, 3.0 equiv.) was dissolved in 1.6 mL water and added to the reaction mixture, which was then stirred 12 h at room temperature. The pH value of the reaction mixture was then adjusted to 2 using 2 M HCl. The resulting precipitate was collected by vacuum filtration and recrystallized from ethanol to afford (E)-4-(3-oxo-3-phenylprop-1-en-1-yl)benzoic acid Compound 1 (514 mg, 49%) as a pale yellow powder. The $^1$H and $^{13}$C NMR spectra matched those reported in the literature.

(E)-4-(3-oxobut-1-en-1-yl)benzoic Acid (Compound 2)

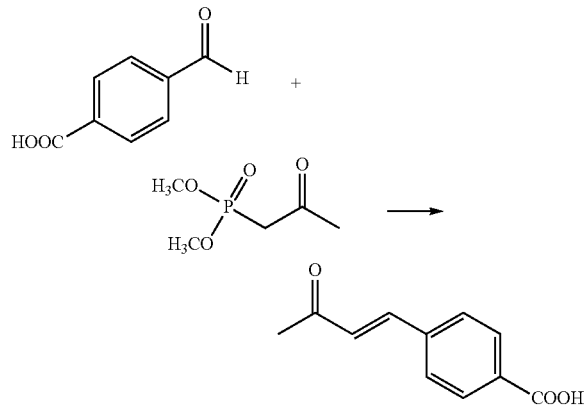

Compound 2 was prepared by modified literature procedure (Chen et al. *Angew. Chem. Int. Ed.* 56, 2022-2025 (2017)). A 150 mL round-bottom flask was charged with 4-formylbenzoic acid (2.2 g, 14.67 mmol, 1.0 equiv), dimethyl 2-oxopropylphosphonate (2.4 g, 14.67 mmol, 1.0 equiv) and THF (65 mL). K$_2$CO$_3$ (4.05 g, 29.34 mmol, 2.0 equiv) was dissolved in water (16 mL) and added to the reaction mixture. The resulting solution was stirred 12 h at room temperature, after which 25 mL of water was added and the pH value of the resulting solution was adjusted to 2 with 2 M HCl. The resulting precipitate was collected by vacuum filtration and recrystallized from ethanol to afford (E)-4-(3-oxobut-1-en-1-yl)benzoic acid (1.7 g, 61%) acid as a white solid. The $^1$H and $^{13}$C NMR spectra matched those reported in the literature.

(E)-4-(2-fluorostyryl)benzoic Acid (Compound 4)

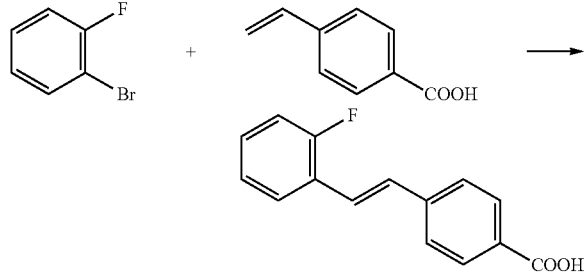

A 50 mL sealable tube was charged under N$_2$ with 1-bromo-2-fluorobenzene (472 mg, 2.70 mmol, 1.0 equiv.), 4-vinylbenzoic acid (400 mg, 2.70 mmol, 1.0 equiv.), Pd(OAc)$_2$ (12 mg, 0.05 25 mmol, 0.02 equiv.), tri(o-tolyl)phosphine (30 mg, 0.1 mmol, 0.04 equiv.), K$_2$CO$_3$ (373 mg, 2.70 mmol, 1.0 equiv.), DMF (12 mL) and triethylamine (4 mL). The tube was sealed and the reaction mixture was stirred at 110° C. for 48 h. The reaction mixture was then cooled to room temperature and diluted with roughly 100 mL H$_2$O, and the resulting aqueous suspension was washed twice with EtOAc. The aqueous phase was then acidified to pH ~3 with 1 M HCl and extracted twice with EtOAc, and the combined organic phases were dried with MgSO$_4$, filtered, and then concentrated under reduced pressure. The resulting solid was recrystallized from CHCl$_3$/EtOH to give (E)-4-(2-fluorostyryl)benzoic acid (Compound 4) (230 mg, 35%) as small colorless crystals.

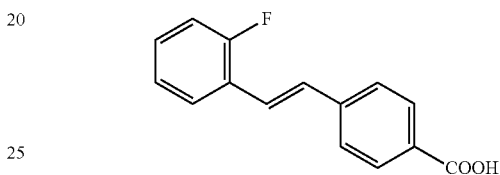

$^1$H NMR (600 MHz, DMSO-d$_6$): δ=12.93 (s, 1H), 7.95 (d, J=8.4 Hz, 2H), 7.83 (td, J=7.8, 1.6 Hz, 1H), 7.75 (d, J=8.5 Hz, 2H), 7.48-7.40 (m, 2H), 7.37 (q, J=7.0 Hz, 1H), 7.29-7.23 (m, 2H). $^{13}$C NMR (126 MHz, DMSO-d$_6$): δ=167.0, 159.9, 141.0, 130.2, 129.9, 129.8, 127.7, 126.7, 124.8, 124.2, 122.7, 116.0, 115.8. $^{19}$F NMR (126 MHz, DMSO-d$_6$): δ=−117.7 (dt, J=12.0, 6.5 Hz). HRMS (ESI$^-$) (m/z): [M-H]$^-$ calculated for C$_{15}$H$_{10}$FO$_2$, 241.0665; found, 241.0665.

(E)-3-fluoro-4-styrylbenzoic Acid (Compound 5)

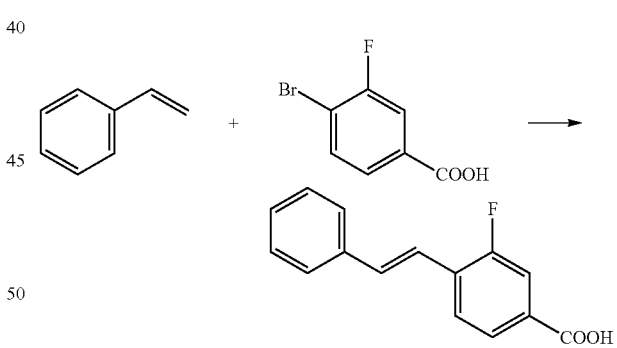

A 50 mL sealable tube was charged under N$_2$ with 4-bromo-3-fluorobenzoic acid (480 mg, 2.19 mmol, 1.0 equiv.), styrene (297 mg, 2.85 mmol, 1.3 equiv.), Pd(OAc)$_2$ (10 mg, 0.04 mmol, 0.02 equiv.), tri(o-tolyl)phosphine (27 mg, 0.09 mmol, 0.04 equiv.), K$_2$CO$_3$ (303 mg, 2.19 mmol, 1.0 equiv.), DMF (12 mL) and triethylamine (4 mL). The tube was sealed and the reaction mixture was stirred at 120° C. for 24 h. The reaction mixture was then cooled to room temperature and diluted with roughly 100 mL H$_2$O, and the resulting aqueous suspension was washed twice with EtOAc. The aqueous phase was then acidified to pH ~3 with 1 M HCl and extracted twice with EtOAc, and the combined organic phases were dried with MgSO$_4$, filtered, and then concentrated under reduced pressure. The resulting solid was recrystallized from MeOH to give (E)-3-fluoro-4-styrylbenzoic acid (Compound 5) (334 mg, 63%) as pale golden needles.

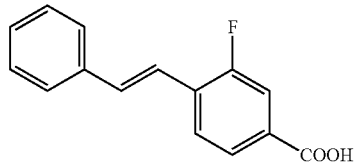 [SMILES: O=C(O)c1ccc(/C=C/c2ccccc2)c(F)c1]

¹H NMR (600 MHz, DMSO-d₆): δ=13.24 (s, 1H), 7.94 (t, J=7.8 Hz, 1H), 7.78 (dd, J=8.1, 1.7 Hz, 1H), 7.71-7.65 (m, 3H), 7.50 (d, J=16.5 Hz, 1H), 7.42 (t, J=7.7 Hz, 2H), 7.37-7.31 (m, 2H). ¹³C NMR (126 MHz, DMSO-d₆): δ=166.0, 159.2, 136.4, 133.6, 131.4, 129.0, 128.8, 128.6, 127.6, 127.0, 119.3, 116.5, 116.3. ¹⁹F NMR (564 MHz, DMSO-d₆): δ=−117.55 (dd, J=11.4, 8.1 Hz). HRMS (ESI⁻) (m/z): [M-H]⁻ calculated for $C_{15}H_{10}FO_2$, 241.0665; found, 241.0663.

(E)-4-(2-(naphthalen-2-yl)vinyl)benzoic Acid (Compound 6)

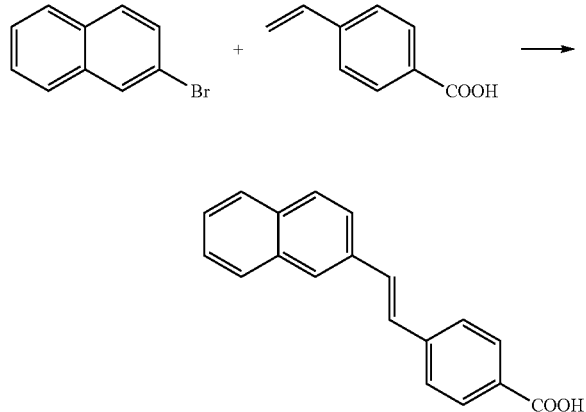

A 50 mL sealable tube was charged under N₂ with 2-bromonaphthalene (453 mg, 2.19 mmol, 1.0 equiv.), 4-vinylbenzoic acid (422 mg, 2.85 mmol, 1.3 equiv.), Pd(OAc)₂ (10 mg, 0.04 mmol, 0.02 equiv.), tri(o-tolyl)phosphine (27 mg, 0.09 mmol, 0.04 equiv.), K₂CO₃ (303 mg, 2.19 mmol, 1.0 equiv.), DMF (12 mL) and triethylamine (4 mL). The tube was sealed and the reaction mixture was stirred at 110° C. for 24 h. The reaction mixture was then cooled to room temperature and diluted with roughly 100 mL H₂O, and the resulting aqueous suspension was washed twice with EtOAc. The aqueous phase was then acidified to pH ~3 with 1 M HCl and extracted twice with EtOAc, and the combined organic phases were dried with MgSO₄, filtered, and then then concentrated under reduced pressure. The resulting solid was triturated with hot MeOH and filtered warm to give (E)-4-(2-(naphthalen-2-yl)vinyl)benzoic acid (Compound 6) (126 mg, 21%) as a colorless powder.

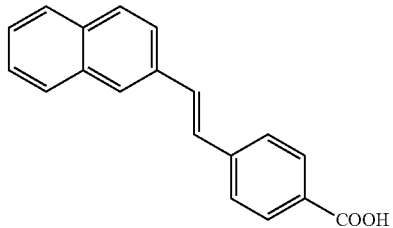 [SMILES: O=C(O)c1ccc(/C=C/c2ccc3ccccc3c2)cc1]

¹H NMR (600 MHz, DMSO-d₆): δ=12.91 (s, 1H), 8.07 (s, 1H), 7.99-7.89 (m, 6H), 7.80-7.75 (m, 2H), 7.59 (d, J=16.4 Hz, 1H), 7.56-7.47 (m, 3H). ¹³C NMR (126 MHz, DMSO-d₆): δ=167.1, 141.4, 134.3, 133.2, 132.8, 131.0, 129.8, 129.5, 128.3, 128.0, 127.9, 127.6, 127.0, 126.6, 126.5, 126.3, 123.6. HRMS (ESI⁻) (m/z): [M-H]⁻ calculated for $C_{19}H_{13}O_2$, 273.0916; found, 273.0921.

(E)-6-styryl-2-naphthoic Acid (Compound 7)

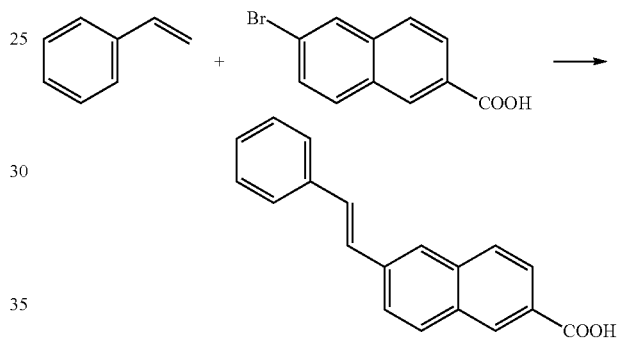

A 50 mL sealable tube was charged under N₂ with 6-bromo-2-naphthoic acid (628 mg, 2.50 mmol, 1.0 equiv.), styrene (339 mg, 3.25 mmol, 1.3 equiv.), Pd(OAc)₂ (12 mg, 0.05 mmol, 0.02 equiv.), tri(o-tolyl)phosphine (30 mg, 0.10 mmol, 0.04 equiv.), K₂CO₃ (346 mg, 2.50 mmol, 1.0 equiv.), DMF (12 mL) and triethylamine (4 mL). The tube was sealed and the reaction mixture was stirred at 110° C. for 24 h. The reaction mixture was then cooled to room temperature and diluted with roughly 100 mL H₂O, and the resulting aqueous suspension was washed twice with EtOAc. The aqueous phase was then acidified to pH ~3 with 1 M HCl and extracted twice with EtOAc, and the combined organic phases were dried with MgSO₄, filtered, and then concentrated under reduced pressure. The resulting solid was triturated with hot CHCl₃ to yield (E)-6-styryl-2-naphthoic Acid (Compound 7) (274 mg, 40%) as a pale cream-colored powder.

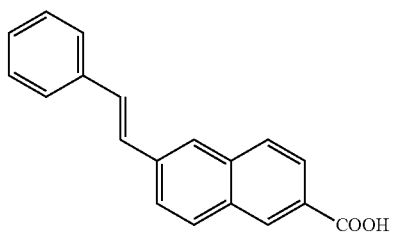 [SMILES: O=C(O)c1ccc2cc(/C=C/c3ccccc3)ccc2c1]

$^1$H NMR (600 MHz, DMSO-d$_6$): δ=13.05 (s, 1H), 8.57 (d, J=1.4 Hz, 1H), 8.13-8.08 (m, 2H), 8.01-7.94 (m, 3H), 7.70-7.66 (m, 2H), 7.52-7.44 (m, 2H), 7.42 (t, J=7.7 Hz, 2H), 7.34-7.29 (m, 1H). $^{13}$C NMR (126 MHz, DMSO-d$_6$): δ=167.4, 137.0, 136.9, 135.3, 131.7, 130.3, 129.7, 128.8, 128.2, 128.1, 128.0, 127.9, 126.7, 126.0, 125.7, 124.5. HRMS (ESI$^-$) (m/z): [M-H]$^-$ calculated for C$_{19}$H$_{13}$O$_2$, 273.0916; found, 273.0915.

(E)-4-(1-oxo-3-phenyl-2-propen-1-yl)benzoic Acid (Compound 22)

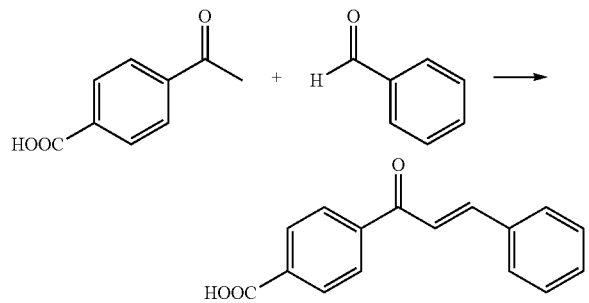

Compound 22 was prepared by modified literature procedure (Deck et al. *Eur. J Med. Chem.* 143, 854-865 (2018)). A 50 mL round-bottom flask was charged with 4-acetylbenzoic acid (500 mg, 3.05 mmol, 1.0 equiv.), benzaldehyde (324 mg, 3.05 mmol, 1.0 equiv.), and EtOH (20 mL). KOH (512 mg, 9.14 mmol, 3.0 equiv.) was dissolved in water (1.6 mL) and added to the reaction mixture, which was then stirred 12 h at room temperature. The pH value of the reaction mixture was then adjusted to 2 with 2 M HCl. The resulting precipitate was collected by vacuum filtration and recrystallized from ethanol to afford (E)-4-(1-oxo-3-phenyl-2-propen-1-yl)benzoic acid Compound 22 (523 mg, 68%) as a pale yellow powder. The $^1$H and $^{13}$C NMR spectra matched those reported in the literature.

Example 4

Preparation of Quantum Dots

QDs were prepared by a modified literature procedure (Flamee et al. *Chem. Mater.* 25, 2476-2483 (2013)). A 25 mL three neck flask was charged with CdO (0.514 g, 4 mmol, 1.0 equiv.), oleic acid (3.02 mL, 3.338 g, 12 mmol, 3.0 equiv.) and 1 octadecene (ODE, 10 mL) under flow of nitrogen. The reaction mixture was heated to 270° C. to dissolve the red CdO in ODE, forming the cadmium carboxylate complex. The heterogeneous ODE-Se precursor was prepared by adding Se (680 mg, 20 mmol, 5.0 equiv.) powder to 10 mL of ODE in a 20 mL vial at room temperature. The resulting dispersion was stirred for injection under nitrogen, during which time the Se did not dissolve. To initiate the reaction, 1 mL of the heterogeneous ODE-Se precursor dispersion was swiftly injected into the colorless reaction mixture containing the Cd precursor. Injection was performed at 270° C., and growth took place for 0.5 min to 2 min at 260° C. to get CdSe QDs with a radius from 1.0 nm to 1.4 nm. The black color of the heterogeneous ODE-Se precursor disappeared upon injection, and the color of the mixture turned from yellow to orange to red depending on the size of the CdSe nanocrystals formed. The reaction mixture was then allowed to cool to room temperature and was purified by the addition of ethanol in a 3:1 ratio relative to the ODE. The resulting turbid solution was centrifuged to obtain a pellet of QDs that was redispersed in hexanes.

Example 5

Procedures for Diastereoselective [2+2] Photocycloaddition

A. Diastereoselective Homo [2+2] Photocycloaddition Using CdSe QDs as Photocatalysts General Procedure for Homo [2+2] Photocycloaddition with 16.5 W High Output LED Using CdSe QDs as Photocatalysts A 4 mL vial was charged with the appropriate 4-vinylbenzoic acid derivative (0.033 mmol, 1.0 equiv.) and oleate-capped CdSe QDs in hexanes (0.132 µmol, 0.004 equiv.), and the solvent was removed in vacuo. The vial was then transferred to a N$_2$ glove box, a magnetic stir bar was added, and the contents were dissolved in 1 mL dry THF. (Note: exposure to peroxide-contaminated THF causes QD degradation, so THF for use with QDs should be regularly tested and stored in a glovebox.) The vial was sealed with a Teflon-lined cap, removed from the glovebox, and stirred under 16.5 W white-light LED irradiation for 48 h with a 455 nm longpass filter to prevent excitation of the substrate. Axial fans were employed to maintain the room temperature. After illumination, 14 mL of MeOH was added to the reaction mixture and the resulting QD precipitate was collected by centrifugation. The supernatant was removed by pipette and concentrated under reduced pressure, and the products were purified by reverse-phase flash column chromatography (eluted with a gradient of 15%-100% MeOH in water) unless otherwise noted. The yields reported represent the isolated yield of the major diastereomeric cycloadducts.

The QD System: syn-4,4'-(3,4-dibenzoylcyclobutane-1,2-diyl)dibenzoic Acid (Compound 8)

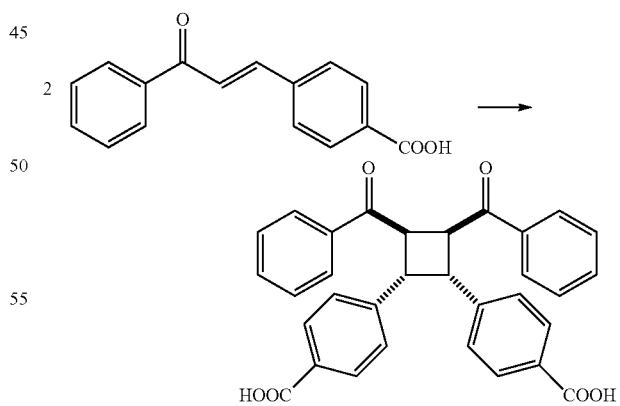

Prepared according to general procedure using 8.4 mg (0.033 mmol, 1.0 equiv.) (E)-4-(3-oxo-3-phenylprop-1-en-1-yl)benzoic acid (Compound 1) and 1.4 nm oleate-capped CdSe QDs (0.27 mL, 501 µM solution in hexanes, 0.132 µmol, 0.004 equiv.), yielding major product syn-4,4'-(3,4-dibenzoylcyclobutane-1,2-diyl)dibenzoic acid (Compound 8) (5.6 mg, 67%) as a white powder.

syn diastereomer (Compound 8 - major product):

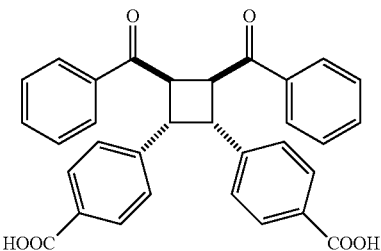

¹H NMR (600 MHz, DMSO-d₆): δ=7.84 (d, J=7.6 Hz, 4H), 7.69 (d, J=8.2 Hz, 4H), 7.55 (t, J=7.4 Hz, 2H), 7.43 (t, J=7.8 Hz, 4H), 7.32 (d, J=8.2 Hz, 4H), 5.21-5.18 (m, 2H), 4.40-4.37 (m, 2H).

¹³C NMR (126 MHz, DMSO-d₆): δ=198.0, 167.1, 144.1, 135.3, 133.1, 128.8, 128.7, 128.7, 128.3, 127.9, 47.1, 44.4.

HRMS (ESI⁻) (m/z): [M-H]⁻ calculated for $C_{32}H_{23}O_6$, 503.1495; found, 503.1493.

The QD System: syn-4,4'-(3,4-diacetylcyclobutane-1,2-diyl)dibenzoic Acid (Compound 10)

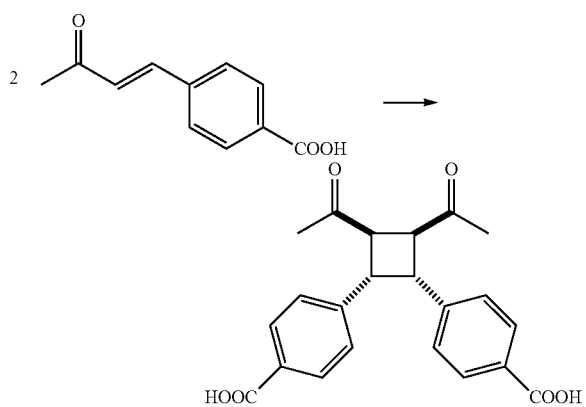

Prepared according to general procedure using 6.33 mg (0.033 mmol, 1.0 equiv.) (E)-4-(3-oxobut-1-en-1-yl)benzoic acid (Compound 2) and 1.2 nm oleate-capped CdSe QDs (0.67 mL, 200 μM solution in hexanes, 0.132 μmol, 0.004 equiv.), yielding major product syn-4,4'-(3,4-diacetylcyclobutane-1,2-diyl)dibenzoic acid (Compound 10) (5.9 mg, 94%) as a white powder.

Syn Diastereomer (Compound 10, Major Product)

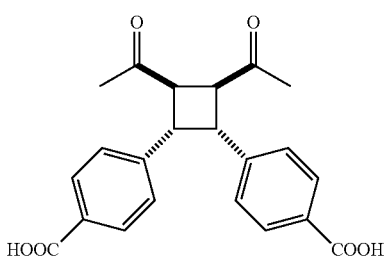

¹H NMR (600 MHz, DMSO-d₆): δ=7.58 (d, J=7.5 Hz, 4H), 6.98 (d, J=7.6 Hz, 4H), 4.11 (d, J=5.9 Hz, 2H), 4.05 (d, J=5.7 Hz, 2H), 2.10 (s, 6H).

¹³C NMR (126 MHz, DMSO-d₆): δ=207.2, 168.7, 165.3, 141.0, 128.5, 127.1, 50.2, 43.6, 28.3.

HRMS (ESI⁻) (m/z): [M-H]⁻ calculated for $C_{22}H_{19}O_6$, 379.1182; found, 379.1189.

The QD System: syn-4,4'-(cyclobutane-1,2-diyl)dibenzoic Acid (Compound 12)

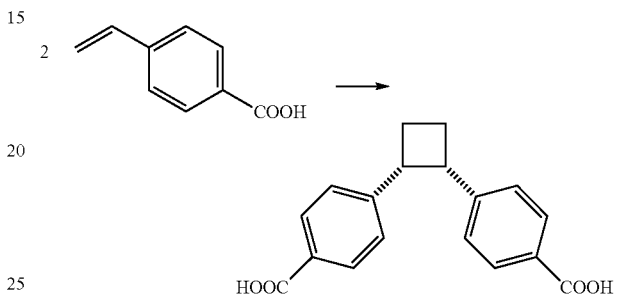

Prepared according to general procedure using 4.93 mg (0.033 mmol, 1.0 equiv.) 4-vinylbenzoic acid (Compound 3) and 1.1 nm oleate-capped CdSe QDs (0.63 mL, 213 μM solution in hexanes, 0.132 μmol, 0.004 equiv.), yielding major product syn-4,4'-(cyclobutane-1,2-diyl)dibenzoic acid (Compound 12) (3.35 mg, 68%) as a white powder.

syn Diastereomer (Compound 12, major product):

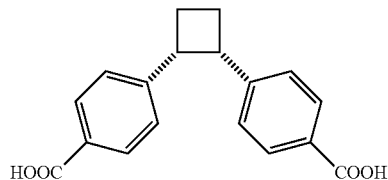

¹H NMR (600 MHz, DMSO-d): δ=7.64 (d, J=8.0 Hz, 4H), 7.09 (d, J=7.9 Hz, 4H), 4.14-4.12 (m, 2H), 2.47-2.45 (m, 4H).

¹³C NMR (126 MHz, DMSO-d₆): δ=168.3, 165.4, 145.8, 129.1, 128.0, 45.0, 24.0.

HRMS (ESI⁻) (m/z): [M-H]⁻ calculated for $C_{18}H_{15}O_4$, 295.0970; found, 295.0963.

The QD System: syn-4,4'-3,4-bis(2-fluorophenyl) cyclobutane-1,2-diyl)dibenzoic Acid (Compound 18)

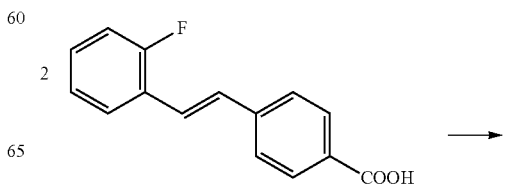

-continued

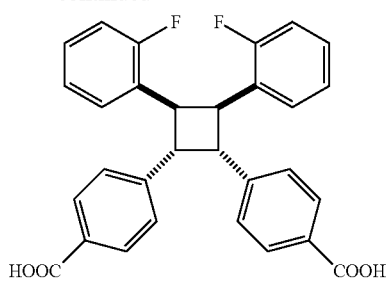

Prepared according to general procedure using 7.99 mg (0.033 mmol, 1.0 equiv.) (E)-4-(2-fluorostyryl)benzoic acid (Compound 4) and 1.1 nm oleate-capped CdSe QDs (0.37 mL, 361 µM solution in hexanes, 0.132 µmol, 0.004 equiv.). The crude products were purified by reverse phase preparative HPLC (Agilent C18 250×21.20 mm; 10 µm eluted with a gradient of 50-75% MeCN:water with 0.1% formic acid over 40 min, then 20 min at 100% MeCN. The flow rate was mL/min.) yielding major product syn-4,4'-3,4-bis(2-fluorophenyl)cyclobutane-1,2-diyl)dibenzoic (5.0 mg, 63%) Compound 18 as a white powder.

syn Diastereomer (Compound 18, major product):

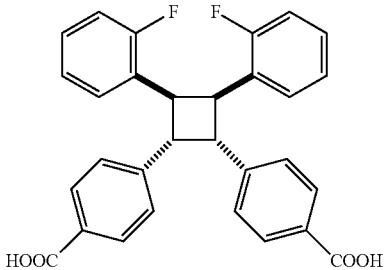

$^1$H NMR (600 MHz, DMSO-$d_6$): δ=7.70 (d, J=8.3 Hz, 2H), 7.41 (t, J=6.9 Hz, 1H), 7.26 (d, J=7.5 Hz, 2H), 7.13 (td, J=8.0, 3.3 Hz, 1H), 7.02 (td, J=7.5, 1.0 Hz, 1H), 6.96 (t, J=8.8 Hz, 1H), 4.74 (d, J=6.7 Hz, 1H), 4.71 (d, J=6.6 Hz, 1H).

$^{13}$C NMR (126 MHz, DMSO-$d_6$): δ=167.5, 164.4, 161.1, 159.1, 144.4, 144.4, 144.3, 129.0, 128.8, 128.3, 128.3, 128.2, 128.2, 127.8, 126.8, 126.7, 123.9, 114.8, 114.6, 45.7 19F NMR (564 MHz, DMSO-$d_6$): δ=−116.40−−116.43 (m).

HRMS (ESI⁻) (m/z): [M-H]⁻ calculated for $C_{30}H_{21}F_2O_4$, 483.1408; found, 483.1403.

The QD System: syn-4,4'-(3,4-diphenylcyclobutane-1,2-diyl)bis(3-fluorobenzoic Acid) (Compound 19)

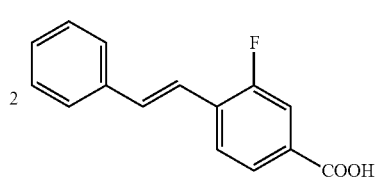

-continued

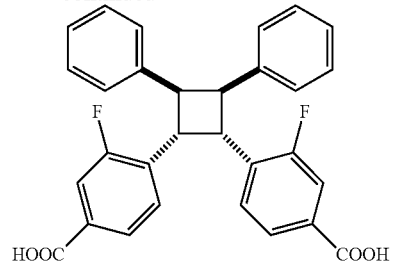

Prepared according to general procedure using 7.99 mg (0.033 mmol, 1.0 equiv.) (E)-3-fluoro-4-styrylbenzoic acid (Compound 5) and 1.1 nm oleate-capped CdSe QDs (0.37 mL, 361 yM solution in hexanes, 0.132 µmol, 0.004 equiv.). The crude products were purified by reverse phase preparative HPLC (Agilent C18 250×21.20 mm; 10 µm eluted with a gradient of 50-75% MeCN:water with 0.1% formic acid over 40 min, then 20 min at 100% MeCN. The flow rate was mL/min.) yielding major product syn-4,4'-(3,4-diphenylcyclobutane-1,2-diyl)bis(3-fluorobenzoic acid) (5.7 mg, 72%) Compound 19 as a white powder.

syn Diastereomer (Compound 19, major product):

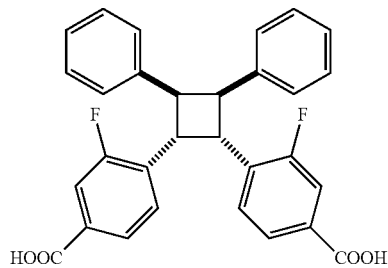

$^1$H NMR (600 MHz, DMSO-$d_6$): δ=7.59 (dd, J=8.0, 1.7 Hz, 2H), 7.53 (t, J=7.6 Hz, 2H), 7.41 (dd, J=10.5, 1.6 Hz, 2H), 7.20-7.17 (m, 4H), 7.15 (t, J=7.6 Hz, 4H), 7.08-7.02 (m, 2H), 4.78 (d, J=6.7 Hz, 2H), 4.66 (d, J=7.0 Hz, 2H).

$^{13}$C NMR (126 MHz, DMSO-$d_6$): δ=166.2, 163.5, 160.7, 158.8, 139.7, 132.1, 131.7, 131.6, 128.9, 128.0, 127.9, 126.1, 124.8, 115.2, 115.0, 45.6. $^{19}$F NMR (564 MHz, DMSO-$d_6$): δ=−73.42, −115.80.

HRMS (ESI⁻) (m/z): [M-H]⁻ calculated for $C_{30}H_{21}F_2O_4$, 483.1408; found, 483.1401.

The QD System: syn-4,4'-(3,4-di(naphthalen-2-yl)cyclobutane-1,2-diyl)dibenzoic Acid (Compound 20)

-continued

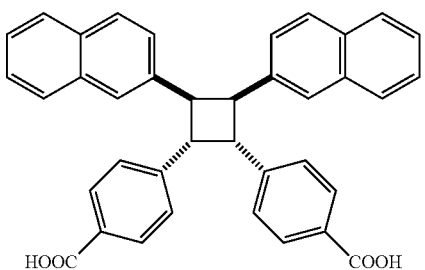

Prepared according to general procedure using 9.05 mg (0.033 mmol, 1.0 equiv.) (E)-4-(2-(naphthalen-2-yl)vinyl) benzoic acid Compound 6 and 1.2 nm oleate-capped CdSe QDs (0.49 mL, 272 µM solution in hexanes, 0.132 µmol, 0.004 equiv.). The crude products were purified by reverse phase preparative HPLC (Agilent C18 250×21.20 mm; 10 µm eluted with a gradient of 55-80% MeCN:water with 0.1% formic acid over 40 min, then 20 min at 100% MeCN. The flow rate was 10 mL/min.) yielding major product syn-4,4'-(3,4-di(naphthalen-2-yl)cyclobutane-1,2-diyl) dibenzoic acid (2.4 mg, 26%) 20 as a white powder.

syn Diastereomer (20, major product):

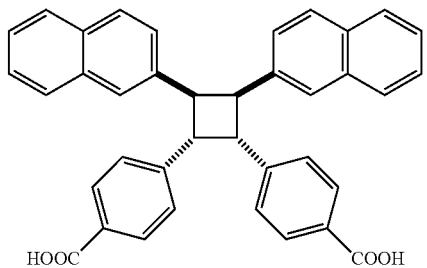

$^1$H NMR (600 MHz, DMSO-$d_6$): δ=7.83 (d, J=1.7 Hz, 2H), 7.75 (d, J=8.1 Hz, 2H), 7.72-7.67 (m, 6H), 7.59 (d, J=8.5 Hz, 2H), 7.42-7.31 (m, 10H), 4.88-4.78 (m, 4H).

$^{13}$C NMR (126 MHz, DMSO-$d_6$): δ=165.09, 138.27, 132.76, 131.42, 130.30, 128.82, 128.22, 127.80, 127.41, 127.26, 127.10, 127.04, 126.01, 125.80, 125.26, 121.19, 46.82, 46.63.

HRMS (ESI$^-$) (m/z): [M-H]$^-$ calculated for $C_3H_{27}O_4$, 547.1909; found, 547.1915.

The QD System: syn-6,6'-(3,4-diphenylcyclobutane-1,2-diyl)bis(2-naphthoic Acid) (Compound 21)

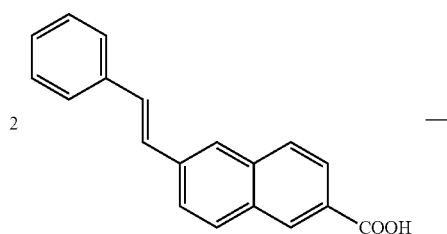

-continued

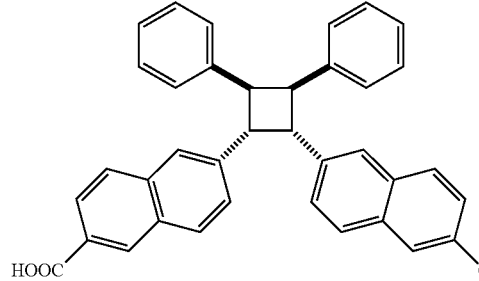

Prepared according to general procedure using 9.05 mg (0.033 mmol, 1.0 equiv.) (E)-6-styryl-2-naphthoic acid 7 and 1.2 nm oleate-capped CdSe QDs (0.49 mL, 272 µM solution in hexanes, 0.132 µmol, 0.004 equiv.). The crude products were purified by reverse phase preparative HPLC (Agilent C18 250×21.20 mm; 10 µm eluted with a gradient of 55-80% MeCN:water with 0.1% formic acid over 40 min, then 20 min at 100% MeCN. The flow rate was 10 mL/min.) yielding major product syn-4,4'-(3,4-diphenylcyclobutane-1,2-diyl)bis(3-fluorobenzoic acid) (5.1 mg, 56%) Compound 21 as a white powder.

syn Diastereomer (21, major product):

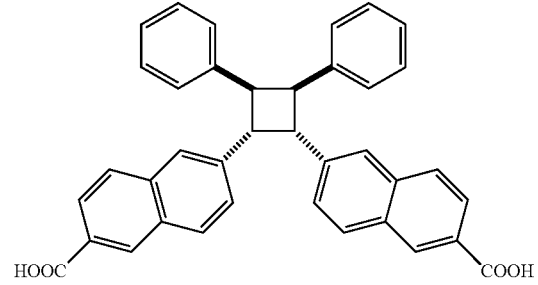

$^1$H NMR (600 MHz, DMSO-$d_6$): δ=7.88 (d, J=1.7 Hz, 2H), 7.85 (dd, J=8.6, 1.7 Hz, 2H), 7.78 (d, J=8.6 Hz, 2H), 7.74 (d, J=8.6 Hz, 2H), 7.43 (dd, J=8.6, 1.8 Hz, 2H), 7.28-7.26 (m, 4H), 7.16 (t, J=7.7 Hz, 4H), 7.09-7.01 (m, 2H), 4.81 (d, J=7.6 Hz, 2H), 4.76 (d, J=7.7 Hz, 2H).

$^{13}$C NMR (126 MHz, DMSO-$d_6$): δ=167.83, 164.44, 140.57, 134.35, 130.63, 129.53, 128.52, 128.47, 128.13, 127.86, 127.59, 127.30, 127.27, 126.68, 126.64, 125.84, 125.60, 47.13, 46.51.

HRMS (ESI$^-$) (m/z): [M-H]$^-$ calculated for $C_{38}H_{27}O_4$, 547.1909; found, 547.1896.

B. Diastereoselective Homo [2+2] Photocycloaddition Using Ir(Ppy)$_3$ or Ru(Bpy)$_3$(PF6)$_2$ as Photocatalysts General Procedure for Homo [2+2] Photocycloaddition with 16.5 W LED Using Ir(Ppy)$_3$ or Ru(Bpy)$_3$(PF$_6$)$_2$ as Photocatalysts For Ir(ppy)$_3$: A 4 mL vial was charged with the appropriate 4-vinylbenzoic acid derivative (0.033 mmol, 1.0 equiv.). The vial was then transferred to a N$_2$ glove box, a magnetic stir bar was added, and the contents were dissolved in 1 mL of a saturated THF solution of Ir(ppy)$_3$ (0.14 mg Ir(ppy)$_3$, 0.208 µmol, 0.0063 equiv.). The vial was sealed with a Teflon-lined cap, removed from the glovebox, and stirred under 16.5 W white-light LED irradiation for 48 h. Axial fans were employed to maintain sample at room temperature. After illumination, the crude products were purified by reverse phase preparative HPLC (Phenomenex Polar RP 150×21.20 mm; 4 µm eluted with a gradient of 30-80% MeCN:water with 0.1% formic acid over 50 min, then 10 min at 100% MeCN. The flow rate was 10 mL/min.) unless otherwise noted. The NMR yields represent the total yield of both the major and the minor diastereomeric cycloadducts.

For Ru(bpy)$_3$(PF$_6$)$_2$: A 4 mL vial was charged with the appropriate 4-vinylbenzoic acid derivative (0.033 mmol, 1.0 equiv.) and Ru(bpy)$_3$(PF$_6$)$_2$ (1.42 mg, 1.65 µmol, 0.05 equiv.) in MeCN, and the solvent was removed in vacuo. The vial was then transferred to a N$_2$ glove box, a magnetic stir bar was added, and the contents were dissolved in 1 mL 5:1 THF:MeCN solution. The vial was sealed with a Teflon-lined cap, removed from the glovebox, and stirred under 16.5 W white-light LED irradiation for 48 h. Axial fans were employed to maintain the room temperature. The NMR yields represent the total yield of both the major and the minor diastereomeric cycloadducts.

Ir(ppy)$_3$ and Ru(bpy)$_3$(PF$_6$)$_2$ Systems: anti-4,4'-(3,4-dibenzoylcyclobutane-1,2-diyl)dibenzoic Acid (Compound 9)

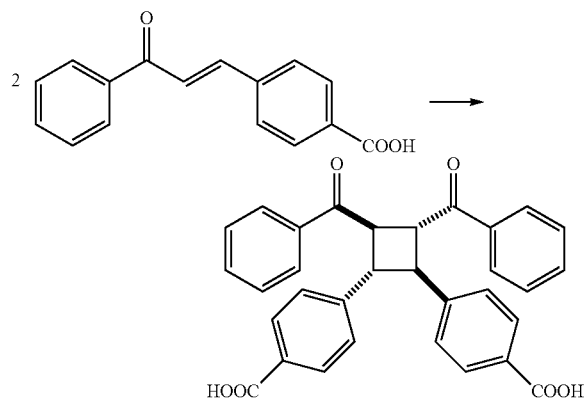

The Ir(ppy)$_3$ system: Prepared according to general procedure using 8.4 mg (0.033 mmol, 1.0 equiv.) (E)-4-(3-oxo-3-phenylprop-1-en-1-yl)benzoic acid Compound 1 yielding major product anti-4,4'-(3,4-dibenzoylcyclobutane-1,2-diyl)dibenzoic acid (Compound 9) (3.8 mg, 45%) and minor product the syn-diastereomer (Compound 8) (1.3 mg, 16%), both as white powders.

The Ru(bpy)$_3$(PF$_6$)$_2$ system: Prepared according to general procedure using 8.4 mg (0.033 mmol, 1.0 equiv.) (E)-4-(3-oxo-3-phenylprop-1-en-1-yl)benzoic acid Compound 1. The yields were obtained by $^1$H NMR spectroscopic analysis of the crude reaction mixture relative to 3,4,5-trichloropyridine internal standard.

anti diastereomer (Compound 9, major product):

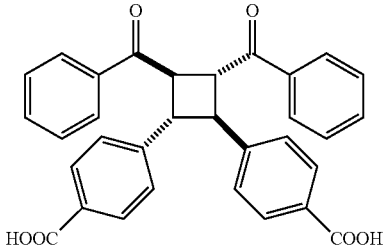

$^1$H NMR (600 MHz, DMSO-d$_6$): δ=7.87 (d, J=8.0 Hz, 4H), 7.78 (d, J=7.7 Hz, 4H), 7.54 (t, J=7.4 Hz, 2H), 7.42 (d, J=8.0 Hz, 4H), 7.37 (t, J=7.7 Hz, 4H), 4.72-4.62 (m, 2H), 4.01-3.92 (m, 2H).

$^{13}$C NMR (126 MHz, DMSO-d$_6$): δ=198.4, 168.6, 165.2, 142.9, 135.2, 133.6, 129.4, 128.6, 128.4, 126.6, 47.2, 47.0.

HRMS (ESI$^-$) (m/z): [M-H]$^-$ calculated for C$_{32}$H$_{23}$O$_6$, 503.1495; found, 503.1485. See Example 5, section A for the characterization information of Compound 8.

Ir(ppy)$_3$ and Ru(bpy)$_3$(PF$_6$)$_2$ Systems: anti-4,4'-(3,4-diacetylcyclobutane-1,2-diyl)dibenzoic Acid (Compound 11)

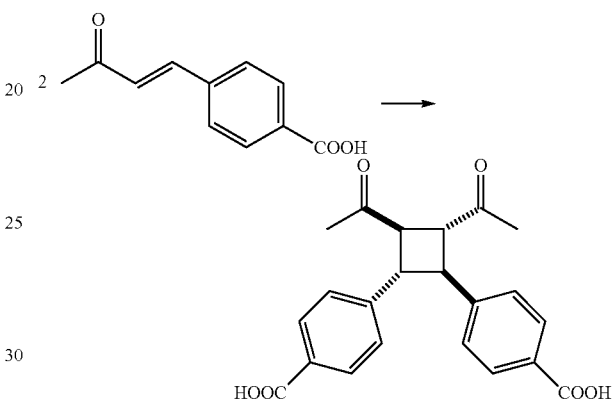

The Ir(ppy)$_3$ system: Prepare according to general procedure using 6.33 mg (0.033 mmol, 1.0 equiv.) (E)-4-(3-oxobut-1-en-1-yl)benzoic acid (Compound 2) yielding major product anti-4,4'-(3,4-diacetylcyclobutane-1,2-diyl)dibenzoic acid (Compound 11) (3.1 mg, 49%) and minor product the syn-diastereomer (Compound 10) (0.8 mg, 13%), both as white powders.

The Ru(bpy)$_3$(PF$_6$)$_2$ system: Prepared according to general procedure using 6.33 mg (0.033 mmol, 1.0 equiv.) (E)-4-(3-oxobut-1-en-1-yl)benzoic acid (Compound 2). The yield of cycloadducts was too small to detect with NMR.

anti Diastereomer (Compound 11, major product):

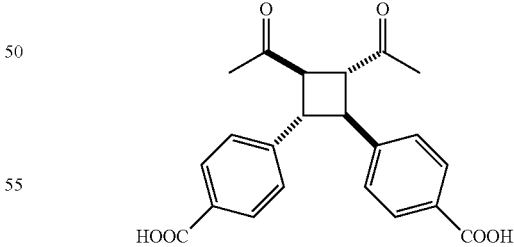

$^1$H NMR (600 MHz, DMSO-d$_6$): δ=7.87 (d, J=7.9 Hz, 4H), 7.36 (d, J=7.9 Hz, 4H), 3.64-3.62 (m, 2H), 3.59-3.57 (m, 2H), 2.04 (s, 6H).

$^{13}$C NMR (126 MHz, DMSO-d$_6$): δ=206.5, 167.9, 164.9, 144.7, 129.5, 126.9, 50.7, 45.9, 28.1.

HRMS (ESI$^-$) (m/z): [M-H]$^-$ calculated for C$_{22}$H$_{19}$O$_6$, 379.1182; found, 379.1187. See Example 5, section A for the characterization information of Compound 10.

Ir(ppy)₃ and Ru(bpy)₃(PF₆)₂ Systems: anti-4,4'-(cyclobutane-1,2-diyl)dibenzoic Acid (Compound 13)

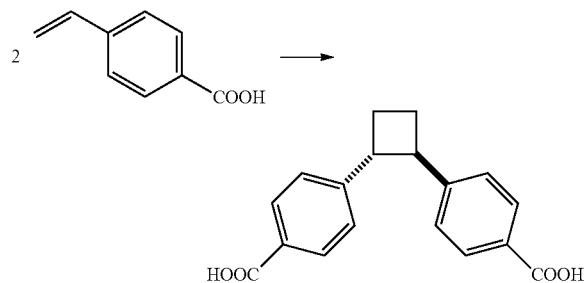

The Ir(ppy)₃ system: Prepared according to general procedure using 4.93 mg (0.033 mmol, 1.0 equiv.) 4-vinylbenzoic acid (Compound 3) yielding a 4:1 mixture of the major product anti-4,4'-(cyclobutane-1,2-diyl)dibenzoic acid (Compound 13) and minor product the syn-diastereomer (Compound 12) as white powders (2.3 mg, 46%).

The Ru(bpy)₃(PF₆)₂ system: Prepared according to general procedure using 4.93 mg (0.033 mmol, 1.0 equiv.) 4-vinylbenzoic acid (Compound 3). The yield of cycloadducts was too small to detect with NMR.

anti Diastereomer (Compound 13, major product) and syn Diastereomer (Compound 12, minor product) as a mixture:

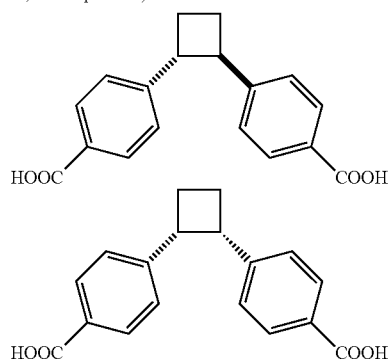

¹H NMR (600 MHz, DMSO-d₆): δ=7.85 (d, J=8.1 Hz, 4H), 7.63 (d, J=8.0 Hz, 1H), 7.32 (d, J=8.1 Hz, 4H), 7.06 (d, J=8.0 Hz, 1H), 4.14-4.08 (m, 0.5H), 3.68-3.60 (m, 2H), 2.48-2.43 (m, 1H), 2.34-2.24 (m, 2H), 2.16-2.06 (m, 2H).

¹³C NMR (126 MHz, DMSO-d₆): δ=167.63, 167.53, 164.56 (2C), 148.13, 145.89, 129.40, 128.68, 127.65, 126.52, 47.17, 44.47, 25.60, 23.36.

HRMS (ESI⁻) (m/z): [M-H]⁻ calculated for $C_{18}H_{15}O_4$, 295.0970; found, 295.0972. See Example 5, section A for the characterization information of Compound 12.

Ir(ppy)₃ and Ru(bpy)₃(PF₆)₂ Systems for Homocoupling of Compound 4 to Compound 7

The Ir(ppy)₃ system: Prepared according to general procedure using 7.99 mg (0.033 mmol, 1.0 equiv.) (E)-4-(2-fluorostyryl)benzoic acid (Compound 4) or (E)-3-fluoro-4-styrylbenzoic acid (Compound 5); 9.05 mg (0.033 mmol, 1.0 equiv.) (E)-4-(2-(naphthalen-2-yl)vinyl)benzoic acid (Compound 6) or (E)-6-styryl-2-naphthoic acid (Compound 7). The yield of cycloadducts was too small to detect with NMR.

The Ru(bpy)₃(PF₆)₂ system: Prepared according to general procedure using 7.99 mg (0.033 mmol, 1.0 equiv.) (E)-4-(2-fluorostyryl)benzoic acid (Compound 4) or (E)-3-fluoro-4-styrylbenzoic acid (Compound 5); 9.05 mg (0.033 mmol, 1.0 equiv.) (E)-4-(2-(naphthalen-2-yl)vinyl)benzoic acid (Compound 6) or (E)-6-styryl-2-naphthoic acid 7. The yield of cycloadducts was too small to detect with NMR.

C. Diastereoselective Hetero [2+2] Photocycloadditions Using CdSe QDs as Photocatalysts General Procedure for Hetero [2+2] Photocycloaddition with a 16.5 W High Output LED Using CdSe QDs as Photocatalysts A 4 mL vial was charged with the sensitized molecule (0.011 mmol, 1.0 equiv.), the coupling partner (0.033 mmol, 3.0 equiv.) and oleate-capped CdSe QDs in hexanes (0.132 μmol, 0.012 equiv.), and the solvent was removed in vacuo. The vial was then transferred to a N₂ glove box, a magnetic stir bar was added, and the contents were dissolved in 1 mL dry THF. (Note: exposure to peroxide-contaminated THF causes QD degradation, so THF for use with QDs should be regularly tested and stored in a glovebox.) The vial was sealed with a Teflon-lined cap and stirred under 16.5 W white-light LED irradiation for 48 h. Regular fans were employed to maintain the room temperature. After illumination, 14 mL of MeOH was added to the reaction mixture and the resulting QD precipitate was collected by centrifugation. The supernatant was removed by pipette and concentrated under reduced pressure, and the products were purified by reverse phase preparative HPLC (Phenomenex Polar RP 150×21.20 mm; 4 μm eluted with a gradient of 30-80% MeCN:water with 0.1% formic acid over 50 min, then 10 min at 100% MeCN. The flow rate was 10 mL/min.) unless otherwise noted. The yields represent the isolated yield of the major diastereomeric cycloadducts.

The QD Aystem: syn-4,4'-(3-benzoylcyclobutane-1,2-diyl)dibenzoic Acid (Compound 14)

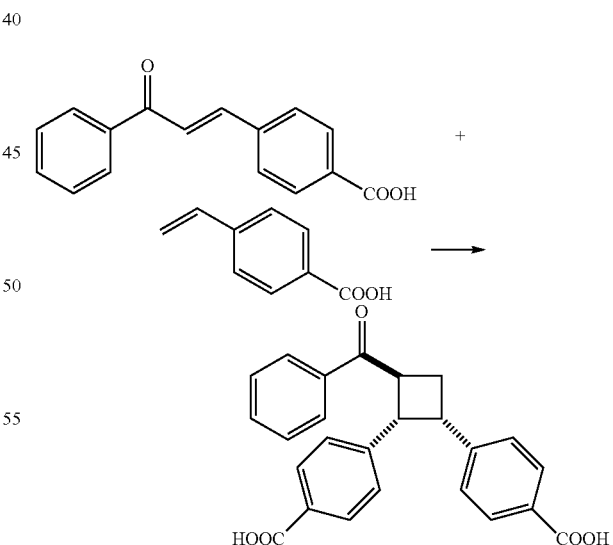

Prepared according to general procedure using 2.8 mg (0.011 mmol, 1.0 equiv.) (E)-4-(3-oxo-3-phenylprop-1-en-1-yl)benzoic acid (Compound 1—the sensitized molecule), 4.93 mg (0.033 mmol, 3.0 equiv.) 4-vinylbenzoic acid (Compound 3—the coupling partner) and 0.27 mL 501 μM (0.132 μmol, 0.012 equiv.) 1.4 nm oleate-capped CdSe QDs in hexanes yielding major product syn-4,4'-(3-benzoylcyclobutane-1,2-diyl)dibenzoic acid (Compound 14) (4.09 mg, 92%) as a white powder.

syn Diastereomer (Compound 14, major product):

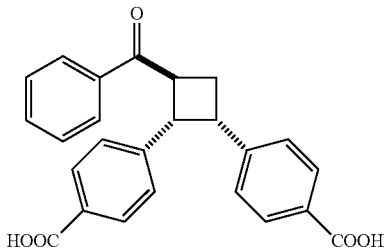

¹H NMR (600 MHz, DMSO-d₆): δ=8.04-7.99 (m, 2H), 7.70-7.60 (m, 5H), 7.54 (t, J=7.6 Hz, 2H), 7.25 (d, J=7.9 Hz, 2H), 7.12 (d, J=8.0 Hz, 2H), 4.76 (dd, J=8.7, 8.7 Hz, 1H), 4.44 (dd, J=9.1, 9.1 Hz, 1H), 4.04 (dt, J=9.5, 5.0 Hz, 1H), 2.83 (dt, J=11.0, 5.0 Hz, 1H), 2.68 (dt, J=11.8, 8.6 Hz, 1H).

¹³C NMR (126 MHz, DMSO-d₆): δ=199.7, 167.7, 167.7, 164.7, 145.1, 143.9, 135.0, 133.4, 128.8, 128.7, 128.6, 128.5, 128.1, 127.7, 45.2, 43.2, 41.2, 27.6.

HRMS (ESI⁻) (m/z): [M-H]⁻ calculated for $C_{25}H_{19}O_5$, 399.1232; found, 399.1236.

Important NOE-Contacts

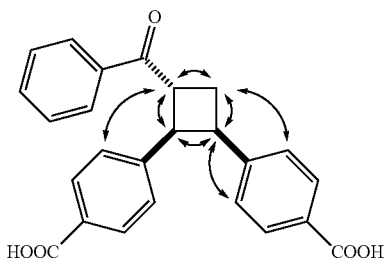 [SMILES: O=C(O)c1ccc([C@H]2[C@H](C(=O)c3ccccc3)C[C@H]2c2ccc(C(=O)O)cc2)cc1]

The QD System: syn-4,4'-(3-acetylcyclobutane-1,2-diyl)dibenzoic Acid (Compound 16)

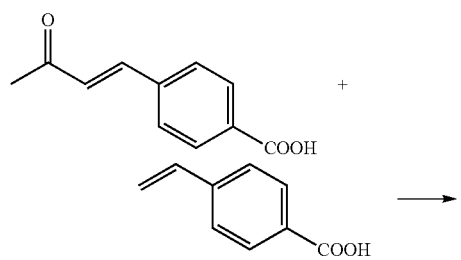

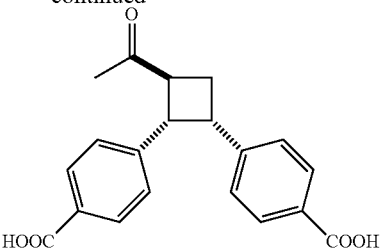

Prepared according to general procedure using 2.11 mg (0.011 mmol, 1.0 equiv.) (E)-4-(3-oxobut-1-en-1-yl)benzoic acid (Compound 2—the sensitized molecule), 4.93 mg (0.033 mmol, 3.0 equiv.) 4-vinylbenzoic acid (Compound 3—the coupling partner) and 0.67 mL 200 μM (0.132 μmol, 0.012 equiv.) 1.2 nm oleate-capped CdSe QDs in hexanes yielding major product syn-4,4'-(3-acetylcyclobutane-1,2-diyl)dibenzoic acid (3.3 mg, 88%) Compound 16 as a white powder.

syn Diastereomer (Compound 16, major product):

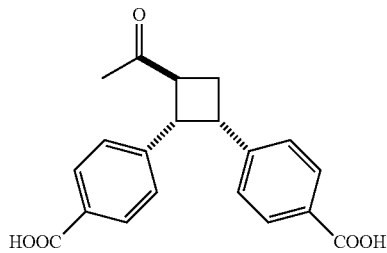

¹H NMR (600 MHz, acetone-d₆): δ=(j, J=8.1 Hz, 2H), 7.72 (d, J=8.1 Hz, 2H), 7.21 (d, J=8.1 Hz, 2H), 7.14 (d, J=8.1 Hz, 2H), 4.34 (dd, J=9.4, 9.4 Hz, 1H), 4.06-4.00 (m, 2H), 2.75-2.70 (m, 1H), 2.67-2.63 (m, 1H), 2.12 (s, 3H).

¹H NMR (600 MHz, DMSO-d₆): δ=7.63 (d, J=7.9 Hz, 2H), 7.61 (d, J=7.9 Hz, 2H), 7.11 (d, J=7.9 Hz, 2H), 7.04 (d, J=7.9 Hz, 2H), 4.20 (t, J=9.5 Hz, 1H), 3.99 (q, J=9.1 Hz, 1H), 3.89 (td, J=9.4, 4.2 Hz, 1H), 2.65-2.59 (m, 1H), 2.55-2.50 (m, overlapping with solvent), 2.10 (s, 3H).

¹³C NMR (126 MHz, DMSO-d₆): δ=208.25, 167.16, 167.16, 145.94 (2C), 144.66 (2C), 128.82, 128.73, 128.20, 127.85, 46.79, 45.66, 40.90, 27.57, 25.59.

HRMS (ESI⁻) (m/z): [M-H]⁻ calculated for $C_{20}H_{17}O_5$, 337.1076; found, 337.1080.

Important NOE-Contacts

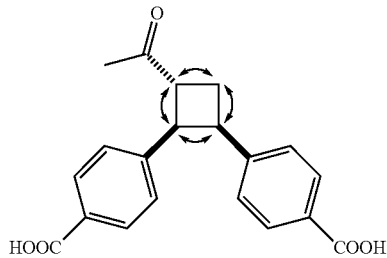 [SMILES: CC(=O)[C@@H]1C[C@@H](c2ccc(C(=O)O)cc2)[C@H]1c1ccc(C(=O)O)cc1]

D. Diastereoselective Hetero [2+2] Photocycloaddition Using Ir(Ppy)₃ or Ru(Bpy)₃(PF₆)₂ as Photocatalysts General Procedure for Homo [2+2] Photocycloaddition with 16.5 W High Output LED Using Ir(Ppy)₃ or Ru(Bpy)₃(PF₆)₂ as Photocatalysts For Ir(ppy)₃: A 4 mL vial was charged with the sensitized molecule (1.0 equiv.) and the coupling partner (3.0 equiv.). The vial was then transferred to a N₂ glove box, a magnetic stir bar was added, and the contents were dissolved in 1 mL of a saturated Ir(ppy)₃ solution in THF (0.14 mg Ir(ppy)₃, 0.208 μmol, 0.0189 equiv.). The vial was sealed with a Teflon-lined cap, removed from the glovebox, and stirred under 16.5 W white-light LED irradiation for 48 h. Axial fans were employed to maintain the room temperature. After illumination, the crude products were purified by reverse phase preparative HPLC (Phenomenex Polar RP 150×21.20 mm; 4 μm eluted with a gradient of 30-80% MeCN:water with 0.1% formic acid over 50 min, then 10 min at 100% MeCN. The flow rate was 10 mL/min.) unless otherwise noted. The NMR yields represent the total yield of both the major and the minor diastereomeric cycloadducts.

For Ru(bpy)₃(PF₆)₂: A 4 mL vial was charged with the sensitized molecule (1.0 equiv.), the coupling partner (3.0 equiv.) and Ru(bpy)₃(PF₆)₂ (0.47 mg, 0.55 μmol, 0.05 equiv.) in MeCN and the solvent was removed in vacuo. The vial was then transferred to a N₂ glove box, a magnetic stir bar was added, and the contents were dissolved in 1 mL 9:1 THF:MeCN solution. The vial was sealed with a Teflon-lined cap, removed from the glovebox, and stirred under 16.5 W white-light LED irradiation for 48 h. Axial fans were employed to keep the sample at room temperature. The NMR yields represent the total yield of both the major and the minor diastereomeric cycloadducts.

Ir(ppy)₃ and Ru(bpy)₃(PF₆)₂ Systems: anti-4,4'-(3-benzoylcyclobutane-1,2-diyl)dibenzoic Acid (Compound 15)

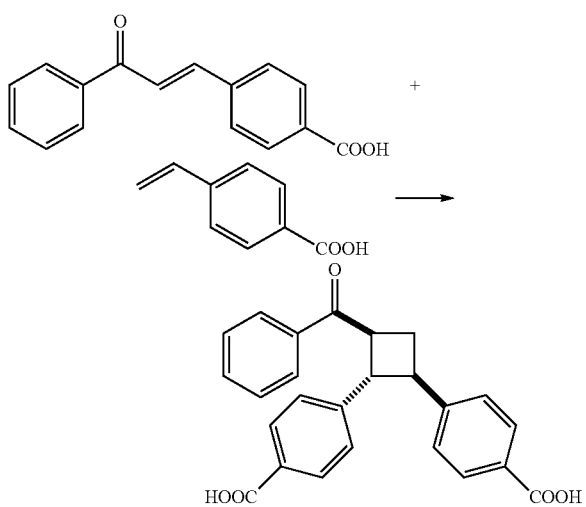

The Ir(ppy)₃ system: Prepared according to the general procedure using 2.8 mg (0.011 mmol, 1.0 equiv.) (E)-4-(3-oxo-3-phenylprop-1-en-1-yl)benzoic acid (Compound 1—the sensitized molecule) and 4.93 mg (0.033 mmol, 3.0 equiv.) 4-vinylbenzoic acid (Compound 3—the coupling partner), yielding a 5:2 mixture of the major product anti-4,4'-(3-benzoylcyclobutane-1,2-diyl)dibenzoic acid (Compound 15) and minor product the syn-diastereomer (Compound 14) as white powders (3.5 mg, 78%).

The Ru(bpy)₃(PF₆)₂ system: Prepared according to the general procedure using 2.8 mg (0.011 mmol, 1.0 equiv.) (E)-4-(3-oxo-3-phenylprop-1-en-1-yl)benzoic acid (Compound 1—the sensitized molecule) and 4.93 mg (0.033 mmol, 3.0 equiv.) 4-vinylbenzoic acid (Compound 3—the coupling partner). The yields were obtained by ¹H NMR spectroscopic analysis of the crude reaction mixture relative to 3,4,5-trichloropyridine internal standard.

anti Diastereomer (Compound 15, major product) and syn Diastereomer (Compound 14, minor product) as a mixture:

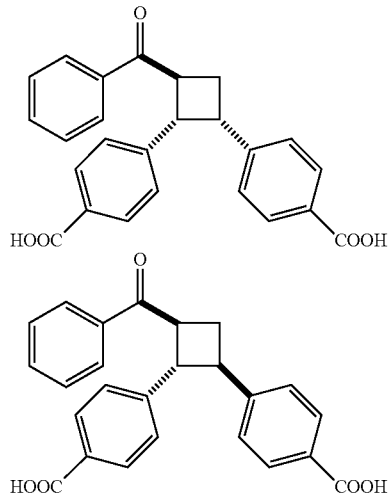

¹H NMR (600 MHz, DMSO-d₆): δ=8.05-8.00 (m, 0.8H), 7.94-7.90 (m, 2H), 7.88 (dd, J=8.3, 2.3 Hz, 4H), 7.69 (d, J=8.0 Hz, 0.8H), 7.67-7.60 (m, 2.2H), 7.56-7.52 (m, 0.8H), 7.51-7.46 (m, 2H), 7.43 (d, J=8.1 Hz, 2H), 7.36 (d, J=8.1 Hz, 2H), 7.28 (d, J=8.0 Hz, 0.8H), 7.14 (d, J=8.1 Hz, 0.8H), 4.77 (q, J=8.6 Hz, 0.4H), 4.47 (t, J=9.1 Hz, 0.4H), 4.36 (q, J=9.3 Hz, 1H), 4.05 (td, J=9.4, 5.0 Hz, 0.4H), 3.92 (t, J=9.7 Hz, 1H), 3.85-3.79 (m, 1H), 2.87-2.79 (m, 1.4H), 2.68 (dt, J=11.8, 8.6 Hz, 0.4H), 2.27 (q, J=10.0 Hz, 1H).

¹³C NMR (126 MHz, DMSO-d₆): 199.80, 199.42, 167.42 (4C), 163.92 (2C), 147.95, 146.81, 145.87, 144.64, 135.26, 135.02, 133.58, 133.54, 129.83, 129.67, 129.64, 128.92, 128.88, 128.81, 128.54 (2C), 128.41 (2C), 128.36, 128.01, 127.30, 126.88, 48.91, 45.17, 44.97, 43.21, 42.52, 41.27, 30.69, 27.71.

HRMS (ESI⁻) (m/z): [M-H]⁻ calculated for C₂₅H₁₉O₅, 399.1232; found, 399.1231. See Example 5, section C for the characterization information of Compound 14.

Ir(ppy)₃ and Ru(bpy)₃(PF₆)₂: anti-4,4'-(3-acetylcyclobutane-1,2-diyl)dibenzoic acid (Compound 17)

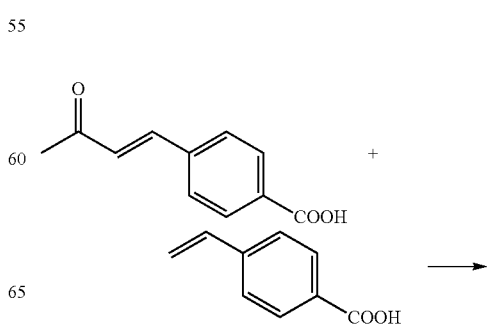

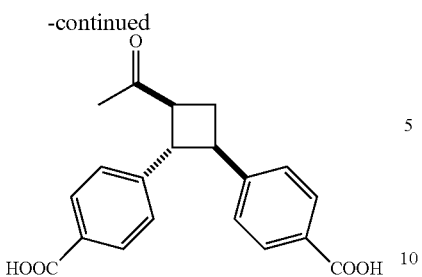

The Ir(ppy)₃ system: Prepared according to the general procedure using 2.11 mg (0.011 mmol, 1.0 equiv.) (E)-4-(3-oxobut-1-en-1-yl)benzoic acid (Compound 2—the sensitized molecule) and 4.93 mg (0.033 mmol, 3.0 equiv.) 4-vinylbenzoic acid (Compound 3—the coupling partner), yielding a 2:1 mixture of the major product anti-4,4'-(3-acetylcyclobutane-1,2-diyl)dibenzoic acid Compound 17 and minor product the syn-diastereomer Compound 16 with Compound 3 as white powders (3 mg, containing coupling products 2.6 mg, 70%).

The Ru(bpy)(PF₆)₂ system: Prepared according to the general procedure using 2.11 mg (0.011 mmol, 1.0 equiv.) (E)-4-(3-oxobut-1-en-1-yl)benzoic acid (Compound 2—the sensitized molecule) and 4.93 mg (0.033 mmol, 3.0 equiv.) 4-vinylbenzoic acid (Compound 3—the coupling partner). The yield of cycloadducts was too small to detect with NMR.

anti Diastereomer (Compound 17, major product) and syn Diastereomer (Compound 16, minor product) with Compound 3 as a mixture:

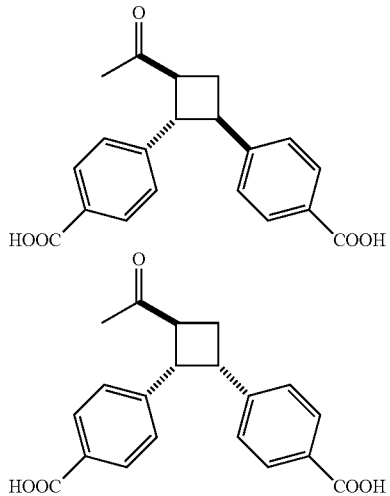

¹H NMR (600 MHz, DMSO-d₆): δ=7.89 (d, J=8.3 Hz, 2H), 7.87 (d, J=8.3 Hz, 2H), 7.66 (d, J=8.3 Hz, 1H), 7.64 (d, J=8.3 Hz, 1H), 7.44 (d, J=8.1 Hz, 2H), 7.32 (d, J=8.1 Hz, 2H), 7.16 (d, J=8.1 Hz, 1H), 7.09 (d, J=8.0 Hz, 1H), 4.24 (t, J=9.5 Hz, 0.5H), 4.01 (q, J=9.1 Hz, 0.5H), 3.92 (td, J=9.3, 4.3 Hz, 0.5H), 3.69 (t, J=9.6 Hz, 1H), 3.64 (q, J=9.4 Hz, 1H), 3.47 (q, J=9.3 Hz, 1H), 2.66-2.52 (m, 2H), 2.18 (q, J=10.0 Hz, 1H), 2.11 (s, 1.5H), 2.03 (s, 3H). with substrate 3 6=7.90 (d, J=8.2 Hz, 1H), 7.57 (d, J=8.2 Hz, 1H), 6.80 (dd, J=17.7, 10.9 Hz, 0.5H), 5.96 (d, J=17.7 Hz, 0.5H), 5.39 (d, J=11.0 Hz, 0.5H).

¹³C NMR (126 MHz, DMSO-d₆): δ=208.21, 207.84, 167.33 (2C), 167.30 (2C), 147.74 (2C), 146.59 (2C), 145.63 (2C), 144.36 (2C), 129.53, 129.50, 128.78, 128.68, 128.09, 127.75, 127.12, 126.73, 49.41, 48.61, 46.82, 45.68, 42.11, 40.88, 28.31, 27.72, 27.55, 25.57. with substrate 3 6=167.26, 140.84, 135.93, 129.60, 126.09, 116.67.

HRMS (ESI⁻) (m/z): [M-H]⁻ calculated for C₂₀H₁₇O₅, 337.1076; found, 337.1081, 295.0975 (C₁₈H₁₅O₄, Compound 3).

See Example 5, section C for the characterization information of Compound 16.

Example 6

Procedure for Control of Homo- vs. Heterocoupling with QD Size

Photoluminescence Measurements.

The photoluminescence (PL) spectra were measured using a right-angle geometry and a 2 mm/1cm dual-pathlength cuvette. The 420 nm excitation beam was applied along the 1 cm path of the cuvette, and the excitation slit width was 3 nm. The sample emission was collected along the 2 mm path with a slit width of 3 nm. PL spectra were corrected for the absorption of the solution in the 450-700 nm region.

General Procedure for Control of Homo- vs. Hetero-[2+2] Photocycloaddition with Different-Size CdSe QDs, Ir(Ppy)₃ or Ru(Bpy)₃(PF₆)₂ as Photocatalysts.

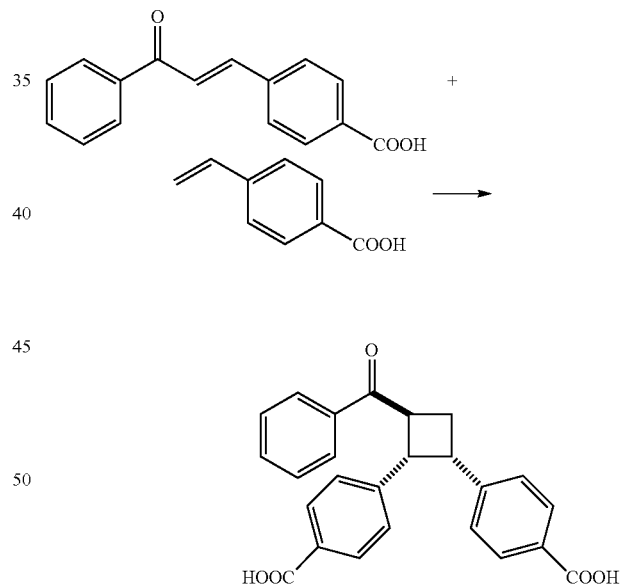

Prepared according the procedure in Example 5, section C, using 2.8 mg (0.011 mmol, 1.0 equiv.) (E)-4-(3-oxo-3-phenylprop-1-en-1-yl)benzoic acid (Compound 1—the sensitized molecule), 4.93 mg (0.033 mmol, 3.0 equiv.) 4-vinylbenzoic acid (Compound 3—the coupling partner). The photosensitizers are 1.4 nm oleate-capped CdSe QDs, 1.0 nm oleate-capped CdSe QDs, Ir(ppy)₃ or Ru(bpy)₃(PF₆)₂ with the same loadings as those described in Example 5, sections C and D.

See Example 5 for certain characterization data. See also FIG. 3 for a depiction of the results.

Example 7

Procedure for Regioselective Hetero [2+2] Photocycloadditions

A. General Procedure for Regioselective Hetero [2+2] Photocycloadditions Using CdSe QDs as Photocatalysts The general procedure for these photocycloadditions is described in Example 5, section C.

The QD System: syn-4,4'-(3-acetyl-4-(2-fluorophenyl)cyclobutane-1,2-diyl)dibenzoic Acid (Compound 24)

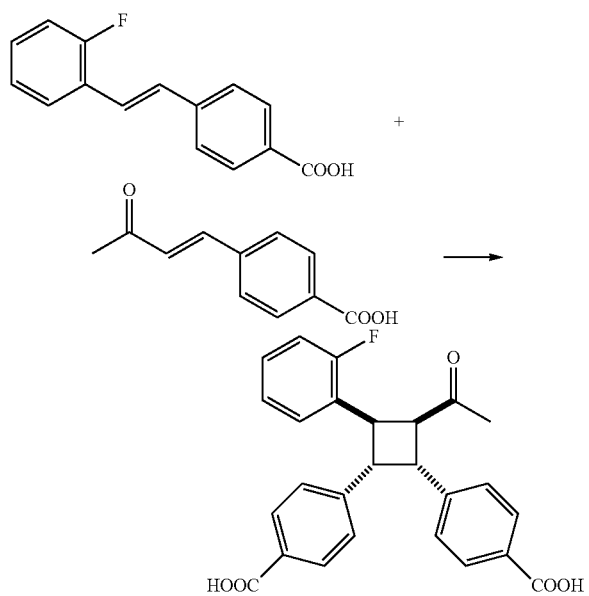

Prepared according to general procedure using 2.66 mg (0.011 mmol, 1.0 equiv.) (E)-4-(2-fluorostyryl)benzoic Acid (Compound 4, the sensitized molecule), 6.33 mg (0.033 mmol, 3.0 equiv.) (E)-4-(3-oxobut-1-en-1-yl)benzoic acid (Compound 2, the coupling partner) and 1.1 nm oleate-capped CdSe QDs (0.37 mL, 361 µM solution in hexanes, 0.132 µmol, 0.012 equiv.) illuminated for 4 days. The crude products were purified by reverse phase preparative HPLC (Agilent C18 250×21.20 mm; 10 µm eluted with a gradient of 40-65% MeCN:water with 0.1% formic acid over 40 min, then 20 min at 100% MeCN. The flow rate was 10 mL/min.) yielding major product syn-4,4'-(3-acetyl-4-(2-fluorophenyl)cyclobutane-1,2-diyl)dibenzoic acid (Compound 24) (1.9 mg, 41%) as a white powder.

syn Diastereomer (Compound 24, major product):

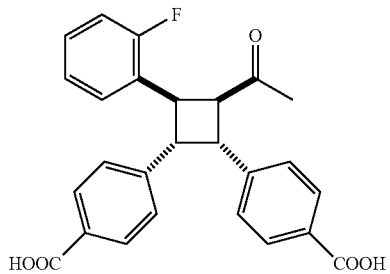

$^1$H NMR (600 MHz, DMSO-$d_6$): δ=7.69 (d, J=8.3 Hz, 2H), 7.63 (d, J=8.2 Hz, 2H), 7.39-7.29 (m, 2H), 7.27-7.17 (m, 4H), 7.13 (d, J=7.9 Hz, 2H), 4.71 (dd, J=10.7, 8.3 Hz, 1H), 4.53-4.45 (m, 2H), 4.35 (dd, J=10.7, 4.8 Hz, 1H), 1.81 (s, 3H).

$^{13}$C NMR (126 MHz, DMSO-$d_6$): δ=206.81, 167.25, 161.09, 159.16, 143.88, 138.75, 136.67, 129.03, 128.97, 128.87, 128.83, 128.59, 128.56, 128.56, 128.14, 127.70, 126.35, 126.24, 124.70, 124.70, 115.25, 115.07, 51.78, 45.06, 42.62, 37.64, 29.50.

$^{19}$F NMR (564 MHz, DMSO-$d_6$): δ=−116.26−−116.39 (m).

HRMS (ESI$^-$) (m/z): [M-H]$^-$ calculated for $C_{26}H_{20}FO_5$, 431.1295; found, 431.1293.

Important NOE-Contacts

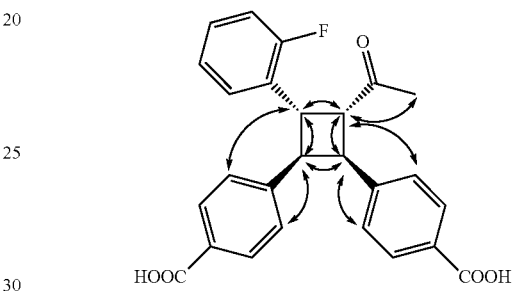

The QD System: syn-4-(3-acetyl-2-(4-carboxyphenyl)-4-phenylcyclobutyl)-3-fluorobenzoic Acid (Compound 25)

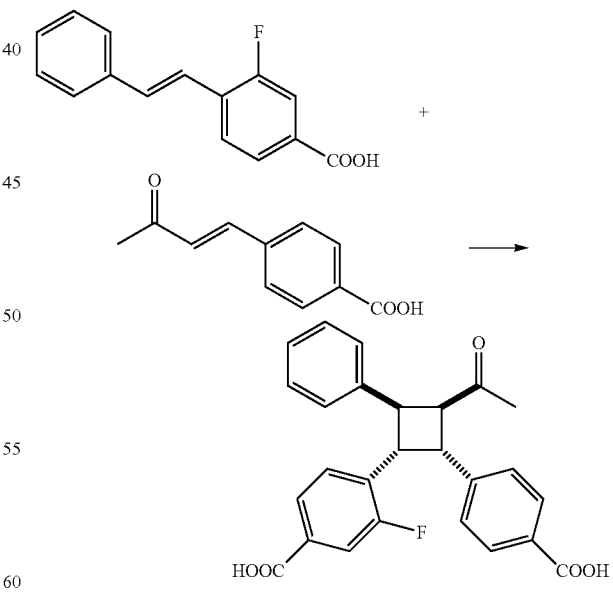

Prepared according to general procedure using 2.66 mg (0.011 mmol, 1.0 equiv.) (E)-3-fluoro-4-styrylbenzoic acid (Compound 5, the sensitized molecule), 6.33 mg (0.033 mmol, 3.0 equiv.) (E)-4-(3-oxobut-1-en-1-yl)benzoic acid (Compound 2, the coupling partner) and 1.1 nm oleate-capped CdSe QDs (0.37 mL, 361 µM solution in hexanes, 0.132 μmol, 0.012 equiv.) illuminated for 4 days. The crude products were purified by reverse phase preparative HPLC (Agilent C18 250×21.20 mm; 10 μm eluted with a gradient of 40-65% MeCN:water with 0.1% formic acid over 40 min, then 20 min at 100% MeCN. The flow rate was 10 mL/min.) yielding major product syn-4-(3-acetyl-2-(4-carboxyphenyl)-4-phenylcyclobutyl)-3-fluorobenzoic acid (3.0 mg, 64%) (Compound 25) as a white powder.

syn Diastereomer (25, major product):

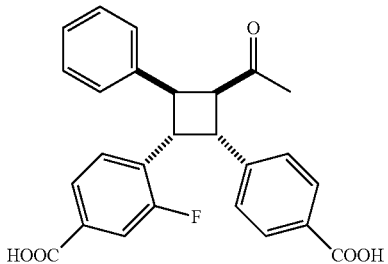

$^1$H NMR (600 MHz, DMSO-d$_6$): δ=7.70 (d, J=8.3 Hz, 2H), 7.50 (dd, J=8.0, 1.6 Hz, 1H), 7.42 (d, J=7.3 Hz, 2H), 7.39-7.32 (m, 5H), 7.29-7.25 (m, 1H), 7.23 (t, J=7.7 Hz, 1H), 4.79 (t, J=10.3 Hz, 1H), 4.58 (t, J=10.0 Hz, 1H), 4.47 (dd, J=10.3, 4.8 Hz, 1H), 4.28 (dd, J=10.9, 4.8 Hz, 1H), 1.67 (s, 3H).

$^{13}$C NMR (126 MHz, DMSO-d$_6$): δ=207.0, 167.1, 166.0, 160.6, 158.6, 144.6, 138.8, 128.9, 128.8, 128.6, 128.6, 128.1, 127.7, 127.2, 124.8, 115.1, 115.0, 53.4, 43.1, 41.8, 41.8, 30.3.

$^{19}$F NMR (564 MHz, DMSO-d$_6$): δ=−114.94.

HRMS (ESI$^-$) (m/z): [M-H]$^-$ calculated for C$_{26}$H$_{20}$FO$_5$, 431.1295; found, 431.1293.

Important NOE-Contacts

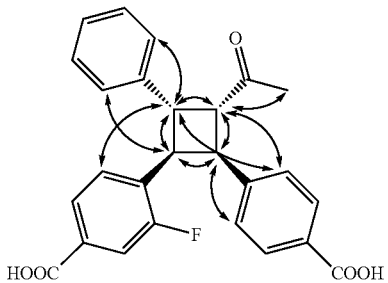 [SMILES: CC(=O)[C@H]1[C@@H](c2ccccc2)[C@H](c2ccc(C(=O)O)cc2F)[C@@H]1c1ccc(C(=O)O)cc1]

The QD System: syn-4,4'-(3-acetyl-4-(naphthalen-2-yl)cyclobutane-1,2-diyl)dibenzoic Acid (Compound 26)

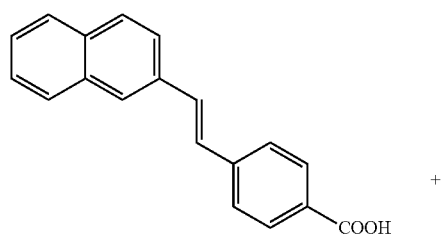

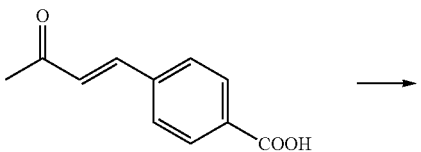

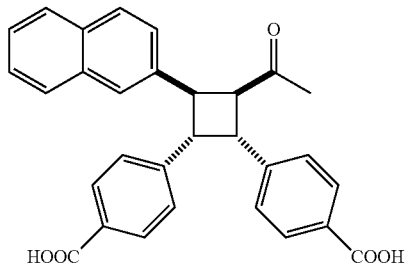

Prepared according to general procedure using 3.02 mg (0.011 mmol, 1.0 equiv.) (E)-4-(2-(naphthalen-2-yl)vinyl)benzoic acid (Compound 6, the sensitized molecule), 6.33 mg (0.033 mmol, 3.0 equiv.) (E)-4-(3-oxobut-1-en-1-yl)benzoic acid (Compound 2, the coupling partner) and 1.2 nm oleate-capped CdSe QDs (0.98 mL, 272 μM solution in hexanes, 0.264 μmol, 0.024 equiv.) illuminated for 4 days. The crude products were purified by reverse phase preparative HPLC (Agilent C18 250×21.20 mm; 10 μm eluted with a gradient of 40-65% MeCN:water with 0.1% formic acid over 40 min, then 20 min at 100% MeCN. The flow rate was 10 mL/min.) yielding major product syn-4-(3-acetyl-2-(4-carboxyphenyl)-4-phenylcyclobutyl)-3-fluorobenzoic acid 1.6 mg 32%) Compound 26 as a white powder.

syn Diastereomer (26, major product):

$^1$H NMR (600 MHz, DMSO-d$_6$): δ=7.94-7.86 (m, 4H), 7.71-7.66 (m, 2H), 7.65-7.60 (m, 3H), 7.52-7.46 (m, 2H), 7.27 (d, J=8.0 Hz, 2H), 7.13 (d, J=8.0 Hz, 2H), 4.77 (dd, J=10.9, 8.2 Hz, 1H), 4.60-4.51 (m, 2H), 4.40 (dd, J=11.0, 5.3 Hz, 1H), 1.67 (s, 3H).

$^{13}$C NMR (126 MHz, DMSO-d$_6$): δ=207.08, 167.72, 164.80, 143.80, 143.65, 137.24, 132.95, 132.06, 130.95, 130.81, 128.76, 128.73, 128.05, 127.99, 127.69, 127.63, 127.50, 126.40, 126.25, 126.03, 125.82, 53.13, 45.98, 45.16, 41.89, 30.09.

HRMS (ESI$^-$) (m/z): [M-Na]$^+$ calculated for C$_{30}$H$_{24}$NaO$_5$, 487.1521; found, 487.1494.

Important NOE-Contacts

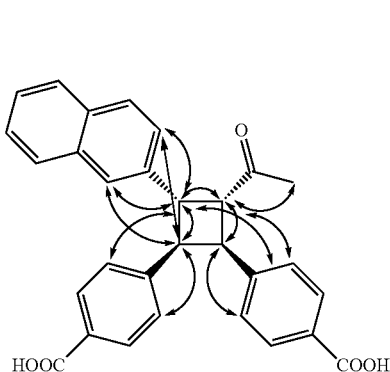 [SMILES: CC(=O)[C@@H]1[C@@H](c2ccc(C(=O)O)cc2)[C@@H](c2ccc(C(=O)O)cc2)[C@@H]1c1ccc2ccccc2c1]

The QD System: syn-6-(3-acetyl-2-(4-carboxyphenyl)-4-phenylcyclobutyl)-2-naphthoic Acid (Compound 27)

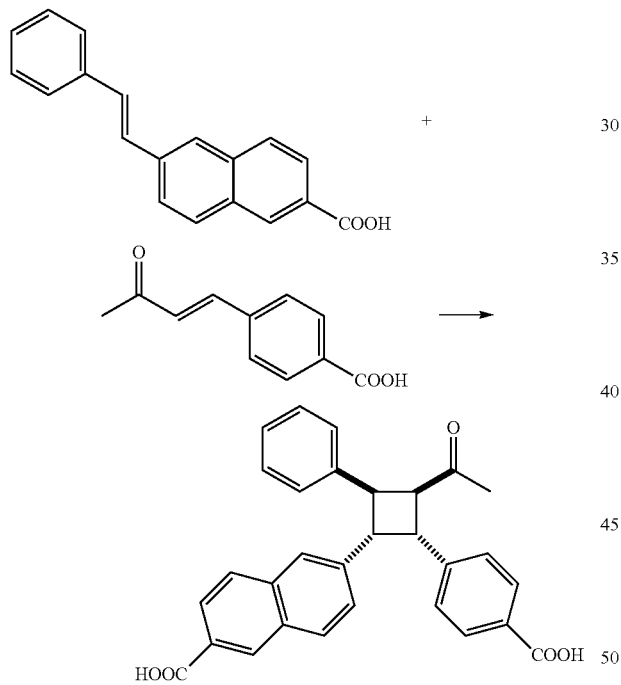

Prepared according to general procedure using 3.02 mg (0.011 mmol, 1.0 equiv.) (E)-6-styryl-2-naphthoic acid (Compound 7, the sensitized molecule), 6.33 mg (0.033 mmol, 3.0 equiv.) (E)-4-(3-oxobut-1-en-1-yl)benzoic acid (Compound 2, the coupling partner) and 1.2 nm oleate-capped CdSe QDs (0.98 mL, 272 μM solution in hexanes, 0.264 μmol, 0.024 equiv.) illuminated for 4 days. The crude products were purified by reverse phase preparative HPLC (Agilent C18 250×21.20 mm; 10 μm eluted with a gradient of 40-65% MeCN:water with 0.1% formic acid over 40 min, then 20 min at 100% MeCN. The flow rate was 10 mL/min.) yielding major product syn-4-(3-acetyl-2-(4-carboxyphenyl)-4-phenylcyclobutyl)-3-fluorobenzoic acid (2.4 mg, 48%) Compound 27 as a white powder.

syn Diastereomer (27, major product):

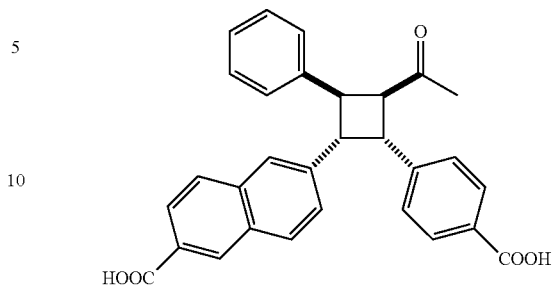

$^1$H NMR (600 MHz, DMSO-$d_6$): δ=8.35 (s, 1H), 7.86 (dd, J=8.6, 1.7 Hz, 1H), 7.75 (dd, J=12.1, 8.6 Hz, 2H), 7.66-7.61 (m, 3H), 7.48-7.43 (m, 2H), 7.37 (t, J=7.7 Hz, 2H), 7.31 (d, J=8.0 Hz, 2H), 7.29-7.23 (m, 2H), 4.70 (dd, J=11.0, 8.6 Hz, 1H), 4.59 (dd, J=10.5, 5.7 Hz, 1H), 4.55-4.49 (m, 1H), 4.40 (dd, J=11.0, 5.7 Hz, 1H), 1.71 (s, 3H).

$^{13}$C NMR (126 MHz, DMSO-$d_6$): δ=207.55, 167.70, 164.48, 144.94, 140.12, 134.71, 131.14, 130.12, 130.08, 129.22, 129.00, 128.68, 128.27, 127.78, 127.67, 127.50, 126.26, 126.08, 53.45, 47.02, 45.58, 42.33, 30.48.

HRMS (ESI$^-$) (m/z): [M-Na]$^+$ calculated for $C_{30}H_{24}NaO_5$, 487.1521; found, 487.1501.

Important NOE-Contacts

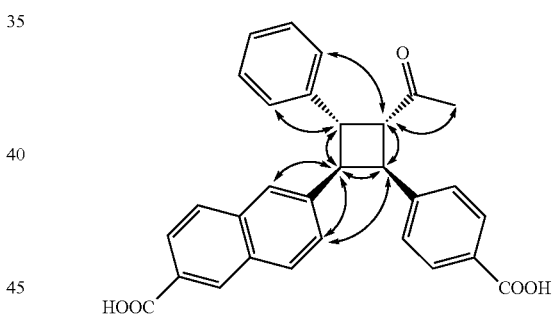

QD System: syn-4,4'-(3-acetyl-4-benzoylcyclobutane-1,2-diyl)dibenzoic Acid (Compound 28)

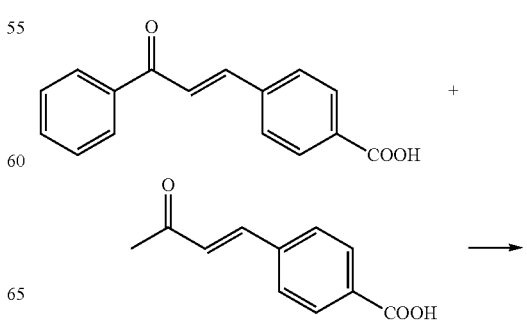

-continued

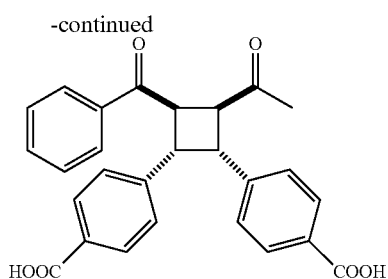

Prepared according to the general procedure using 2.8 mg (0.011 mmol, 1.0 equiv.) (E)-4-(3-oxo-3-phenylprop-1-en-1-yl)benzoic acid (Compound 1—the sensitized molecule), 6.33 mg (0.033 mmol, 3.0 equiv.) (E)-4-(3-oxobut-1-en-1-yl)benzoic acid (Compound 2—the coupling partner) and 0.27 mL 501 µM (0.132 µmol, 0.012 equiv.) 1.4 nm oleate-capped CdSe QDs in hexanes. The crude products were purified by reverse phase preparative HPLC (Agilent C18 250×21.20 mm; 10 µm eluted with a gradient of 30-60% MeCN:water with 0.1% formic acid over 40 min, then 20 min at 100% MeCN. The flow rate was 10 mL/min.) yielding major product syn-4,4'-(3-acetyl-4-benzoylcyclobutane-1,2-diyl)dibenzoic acid (Compound 28) (3.7 mg, 75%) as a white powder.

syn Diastereomer (Compound 28, major product):

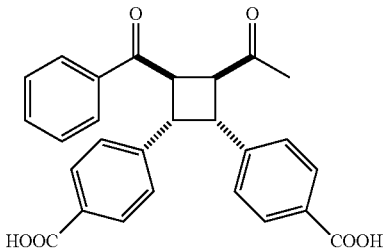

$^1$H NMR (600 MHz, DMSO-$d_6$): δ=7.91 (d, J=7.3 Hz, 2H), 7.70-7.65 (m, 4H), 7.63 (t, J=7.4 Hz, 1H), 7.52 (t, J=7.6 Hz, 2H), 7.26-7.23 (m, 4H), 5.05-4.93 (m, 1H), 4.45-4.36 (m, 1H), 4.31-4.23 (m, 2H), 2.00 (s, 3H).

$^{13}$C NMR (126 MHz, DMSO-$d_6$): δ=206.40, 198.34, 167.08 (2C), 167.06, 144.41, 144.09, 135.40, 133.30, 128.86, 128.80, 128.75, 128.65, 128.56, 128.20, 128.05, 50.50, 46.40, 43.81, 43.76, 28.09.

HRMS (ESI$^-$) (m/z): [M-H]$^-$ calculated for $C_{27}H_{21}O_6$, 441.1338; found, 441.1341.

Important NOE-Contacts

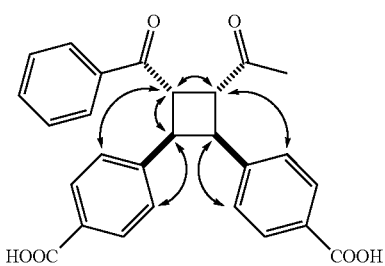 [SMILES: CC(=O)[C@H]1[C@@H](C(=O)c2ccccc2)[C@H](c2ccc(C(=O)O)cc2)[C@@H]1c1ccc(C(=O)O)cc1]

QDs System: syn-4-(3-acetyl-2-(4-carboxyphenyl)-4-phenylcyclobutane-1-carbonyl)benzoic Acid (Compound 30)

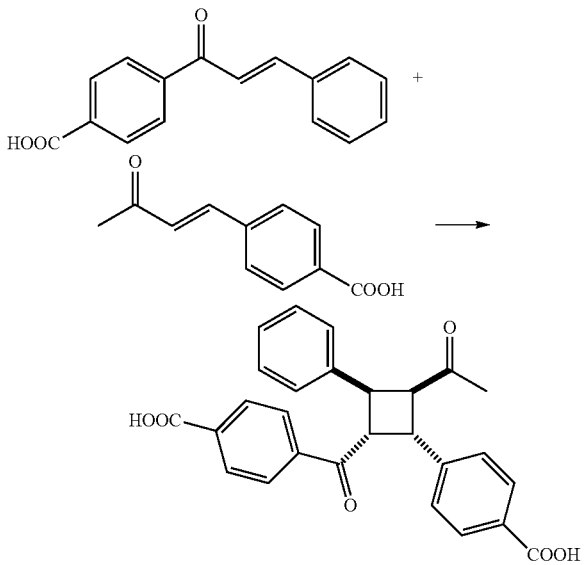

The reaction was conducted on large (0.033 mmol) scale. Prepared according to general procedure using 8.4 mg (0.033 mmol, 1.0 equiv.) (E)-4-(1-oxo-3-phenyl-2-propen-1-yl)benzoic acid (Compound 22—the sensitized molecule), 18.99 mg (0.099 mmol, 3.0 equiv.) (E)-4-(3-oxobut-1-en-1-yl)benzoic acid (Compound 2—the coupling partner) and 0.81 mL 501 µM (0.396 µmol, 0.036 equiv.) 1.4 nm oleate-capped CdSe QDs in hexanes illuminated with a blue LED for 4 days. The system was stirred under 34 W blue LED irradiation for 4 days. The crude products were purified by reverse phase preparative HPLC (Agilent C18 250×21.20 mm; 10 µm; eluted with a gradient of 30-60% MeCN:water with 0.1% formic acid over 80 min, then 20 min at 100% MeCN. The flow rate was 10 mL/min.) yielding major product syn-4-(3-acetyl-2-(4-carboxyphenyl)-4-phenylcyclobutane-1-carbonyl)benzoic acid (Compound 30) (1.5 mg, 10%) as a white powder.

syn Diastereomer (Compound 30, major product):

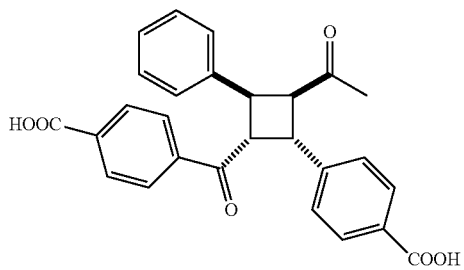

$^1$H NMR (600 MHz, DMSO-$d_6$): δ=7.81 (d, J=7.6 Hz, 2H), 7.74 (d, J=7.6 Hz, 2H), 7.62 (d, J=8.2 Hz, 2H), 7.46 (d, J=7.5 Hz, 2H), 7.36 (t, J=7.6 Hz, 2H), 7.29-7.25 (m, 3H), 4.91 (dd, J=10.7, 7.8 Hz, 1H), 4.75 (dd, J=11.2, 7.8 Hz, 1H), 4.70 (dd, J=10.8, 6.5 Hz, 1H), 4.16 (dd, J=11.2, 6.4 Hz, 1H), 1.63 (s, 3H).

$^{13}$C NMR (126 MHz, DMSO-d$_6$): δ=206.40, 198.07, 166.95, 166.54, 163.03, 139.17, 138.95, 134.34, 129.23, 128.92, 128.85, 128.42, 128.28, 128.23, 128.09, 127.08, 53.51, 48.98, 41.15, 40.46, 29.61.

HRMS (ESI$^-$) (m/z): [M-H]$^-$ calculated for C$_{20}$H$_{17}$O$_5$, 441.1338; found, 441.1329.

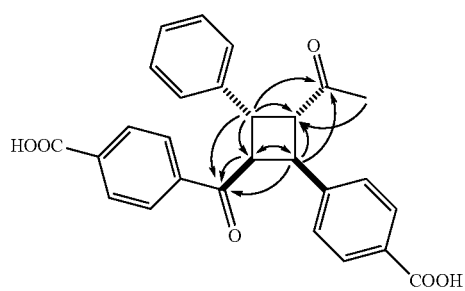

Important NOE-contacts

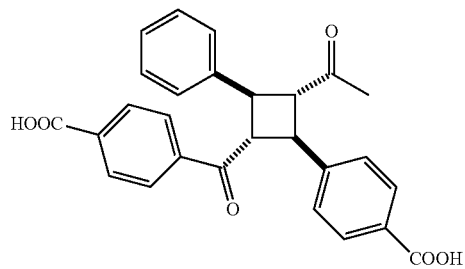

Important HMBC-contacts anti Diastereomer (Compound S1, minor product):

$^1$H NMR (600 MHz, DMSO-d$_6$): δ=7.91 (d, J=8.2 Hz, 2H), 7.70 (d, J=7.3 Hz, 2H), 7.60-7.54 (m, 4H), 7.46 (d, J=7.4 Hz, 2H), 7.37 (t, J=7.6 Hz, 2H), 7.29 (t, J=7.3 Hz, 1H), 4.39 (t, J=9.2 Hz, 1H), 3.87 (t, J=9.4 Hz, 1H), 3.78-3.66 (m, 2H), 1.91 (s, 3H).

$^{13}$C NMR (126 MHz, DMSO-d$_6$): δ=206.66, 198.22, 167.23, 167.18 (2C), 163.43, 163.39, 140.70, 129.53, 128.93, 128.90, 128.58, 128.25, 127.76, 127.72, 127.17, 55.17, 51.69, 42.77, 41.20, 40.02, 39.85, 39.69, 39.52, 39.35, 39.19, 39.02, 28.08.

HRMS (ESI$^-$) (m/z): [M-H]$^-$ calculated for C$_{20}$H$_{17}$O$_5$, 441.1338; found, 441.1328.

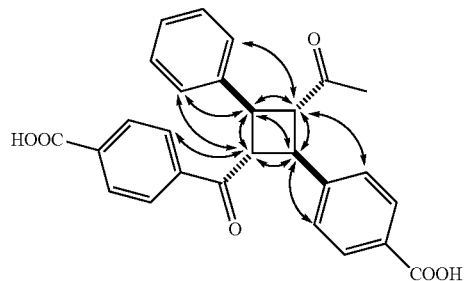

Important NOE-contacts

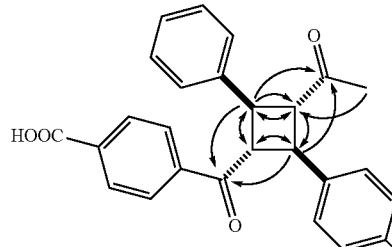

Important HMBC-contacts

QD Aystem: anti-4-(2-acetyl-3-benzoyl-4-phenylcyclobutyl)benzoic Acid (Control Study, Compound 32)

Prepare according to genera procedure using 2.3 mg (0.011 mmol, 1.0 equiv.) chalcone Compound 15 (the sensitized molecule), 6.33 mg (0.033 mmol, 3.0 equiv.) (E)-4-(3-oxobut-1-en-1-yl)benzoic acid (Compound 2—the coupling partner) and 0.27 mL 501 μM (0.132 μmol, 0.012 equiv.) 1.4 nm oleate-capped CdSe QDs in hexanes illuminated with a blue LED for 4 days. The crude product mixture was concentrated under reduced pressure. The yield reported is obtained by $^1$H NMR spectroscopic analysis of the crude reaction mixture relative to 3,4,5-trichloropyridine internal standard. The NMR yields represent the total yield of both the major Compound 32 and the minor Compound S3 diastereomeric cycloadducts.

See Example 7, section B (below) for the characterization information of Compounds 32 and S3.

B. Diastereoselective Hetero [2+2] Photocycloaddition Using Ir(Ppy)₃ as a Photocatalyst The general procedures for these photocycloadditions are described in Example 5, section D.

Ir(Ppy)₃ Systems for Heterocoupling of Compound 4 to Compound 7 with Compound 2

The Ir(ppy)₃ system: Prepared according to general procedure using 7.99 mg (0.033 mmol, 1.0 equiv.) (E)-4-(2-fluorostyryl)benzoic acid (Compound 4) or (E)-3-fluoro-4-styrylbenzoic acid (Compound 5); 9.05 mg (0.033 mmol, 1.0 equiv.) (E)-4-(2-(naphthalen-2-yl)vinyl)benzoic acid (Compound 6) or (E)-6-styryl-2-naphthoic acid (Compound 7, the sensitized molecule) and 6.33 mg (0.033 mmol, 3.0 equiv.) (E)-4-(3-oxobut-1-en-1-yl)benzoic acid (Compound 2, the coupling partner) illuminated for 4 days. The yield of cycloadducts was too small to detect with NMR.

Ir(ppy)₃ System: anti-4,4'-(3-acetyl-4-benzoylcyclobutane-1,2-diyl)dibenzoic Acid (Compound 29)

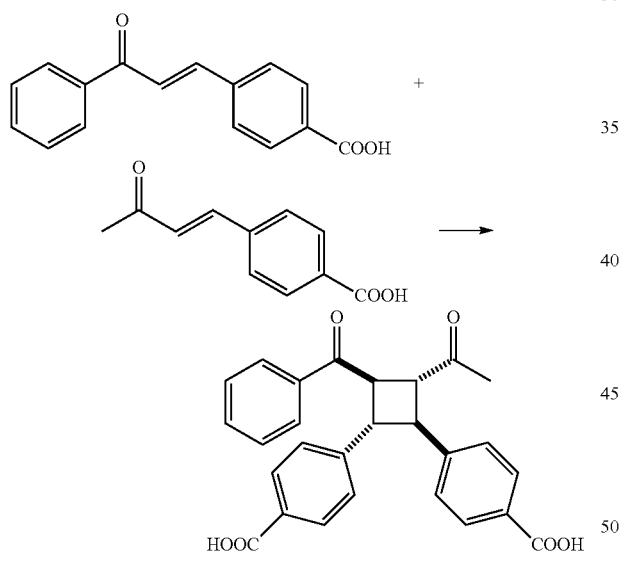

The Ir(ppy)₃ system: Prepared according to the general procedure using 2.8 mg (0.011 mmol, 1.0 equiv.) (E)-4-(3-oxo-3-phenylprop-1-en-1-yl)benzoic acid (Compound 1—the sensitized molecule), 6.33 mg (0.033 mmol, 3.0 equiv.) (E)-4-(3-oxobut-1-en-1-yl)benzoic acid (Compound 2—the coupling partner). The crude products were purified by reverse phase preparative HPLC (Agilent C18 250×21.20 mm; 10 μm eluted with a gradient of 30-60% MeCN:water with 0.1% formic acid over 40 min, then 20 min at 100% MeCN. The flow rate was 10 mL/min.) yielding major product anti-4,4'-(3-acetyl-4-benzoylcyclobutane-1,2-diyl) dibenzoic acid (Compound 29) (2.3 mg, 47%) and minor product the syn-diastereomer (Compound 28) (0.6 mg, 14%), both as white powders.

Anti Diastereomer (29, Major Product)

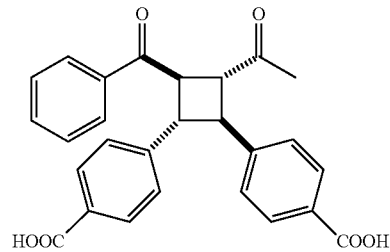 [SMILES: CC(=O)[C@H]1[C@H](C(=O)c2ccccc2)[C@@H](c2ccc(C(=O)O)cc2)[C@@H]1c1ccc(C(=O)O)cc1]

$^1$H NMR (600 MHz, DMSO-d$_6$): δ=7.90 (d, J=7.5 Hz, 2H), 7.86 (d, J=7.5 Hz, 2H), 7.81 (d, J=7.8 Hz, 2H), 7.59 (t, J=7.3 Hz, 1H), 7.42 (t, J=6.7 Hz, 4H), 7.38 (d, J=7.5 Hz, 2H), 4.52 (t, J=8.2 Hz, 1H), 3.89-3.80 (m, 2H), 3.69 (t, J=8.8 Hz, 1H), 2.02 (s, 3H).

$^{13}$C NMR (126 MHz, DMSO-d$_6$): δ=206.48, 198.13, 167.44, 167.44, 164.16, 145.67, 145.04, 135.27, 133.73, 129.65, 129.64, 128.68 (2C), 128.53, 127.46, 127.15, 50.51, 47.27, 46.63, 45.86, 28.02.

HRMS (ESI⁻) (m/z): [M-H]⁻ calculated for C$_{27}$H$_{21}$O$_6$, 441.1338; found, 441.1342.

Important NOE-Contacts

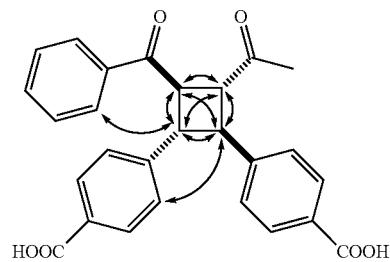 [SMILES: CC(=O)[C@H]1[C@H](C(=O)c2ccccc2)[C@@H](c2ccc(C(=O)O)cc2)[C@@H]1c1ccc(C(=O)O)cc1]

See section Example, section or the characterization information of Compound 28.

Ir(ppy)₃ System: anti-4-(2-acetyl-3-(4-carboxybenzoyl)-4-phenylcyclobutyl)benzoic acid (Compound 31)

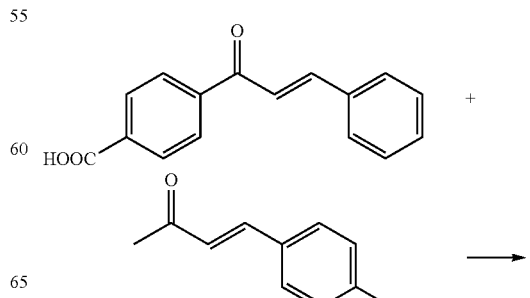

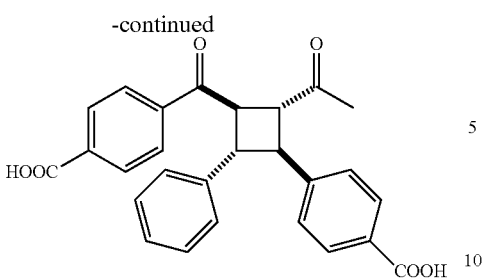

The Ir(ppy)₃ system: Prepared according to general procedure using 2.8 mg (0.011 mmol, 1.0 equiv.) (E)-4-(1-oxo-3-phenyl-2-propen-1-yl)benzoic acid (Compound 22—the sensitized molecule), 6.33 mg (0.033 mmol, 3.0 equiv.) (E)-4-(3-oxobut-1-en-1-yl)benzoic acid (Compound 2—the coupling partner) were illuminated with a blue LED for 4 days. The crude products were purified by reverse phase preparative HPLC (Agilent C18 250×21.20 mm; 10 μm; eluted with a gradient of 30-60% MeCN:water with 0.1% formic acid over 80 min, then 20 min at 100% MeCN. The flow rate was 10 mL/min.) yielding major product anti-4-(2-acetyl-3-(4-carboxybenzoyl)-4-phenylcyclobutyl)benzoic acid (Compound 31) (2.6 mg, 53%) and minor product the syn-diastereomer (Compound S2) (0.6 mg, 13%), both as white powders.

Anti Diastereomer (Compound 31, Major Product)

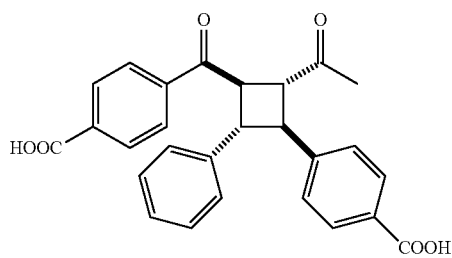

$^1$H NMR (600 MHz, DMSO-$d_6$): δ=7.89 (dd, J=14.2, 8.4 Hz, 4H), 7.84 (dd, J=8.3, 2.5 Hz, 2H), 7.46 (d, J=8.4 Hz, 2H), 7.34-7.28 (m, 4H), 7.26 (t, J=6.8 Hz, 1H), 4.49 (t, J=8.9 Hz, 1H), 3.88-3.79 (m, 2H), 3.63 (t, J=9.4 Hz, 1H), 2.02 (s, 3H).
$^{13}$C NMR (126 MHz, DMSO-$d_6$): δ=206.5, 198.1, 167.1, 166.8, 166.7, 163.5, 163.3, 146.2, 140.5, 129.6, 129.2, 128.7, 128.5, 127.4, 127.3 (2C), 50.4, 47.6, 47.4, 45.8, 28.0.
HRMS (ESI⁻) (m/z): [M-H]⁻ calculated for $C_{27}H_{21}O_6$, 441.1338; found, 441.1343.

Important NOE-contacts

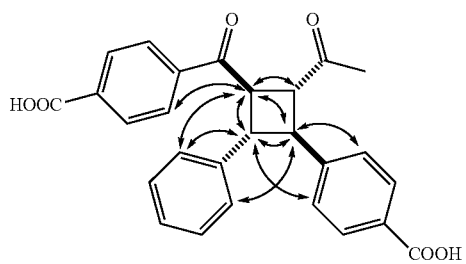

Important HMBC-contacts

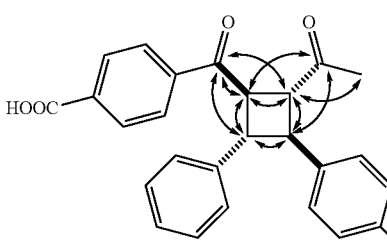

syn Diastereomer (Compound S2, minor product):

[structure]

$^1$H NMR (600 MHz, DMSO-$d_6$): δ=7.87 (d, J=8.0 Hz, 2H), 7.79 (d, J=8.2 Hz, 2H), 7.56 (d, J=7.7 Hz, 2H), 7.10 (d, J=6.7 Hz, 4H), 7.00 (dd, J=16.4, 7.3 Hz, 3H), 4.86 (dd, J=9.7, 6.1 Hz, 1H), 4.29 (dd, J=9.5, 7.0 Hz, 1H), 4.12 (td, J=10.0, 6.7 Hz, 2H), 1.98 (s, 3H).
$^{13}$C NMR (126 MHz, DMSO-$d_6$): δ=206.67, 198.56, 168.78, 168.27, 165.62 (2C), 139.05, 135.60, 129.04, 128.52, 128.05, 127.77, 127.38, 127.29, 126.10, 50.69, 46.95, 43.99, 43.66, 28.19.
HRMS (ESI⁻) (m/z): [M-H]⁻ calculated for $C_{27}H_{21}O_6$, 441.1338; found, 441.1337.

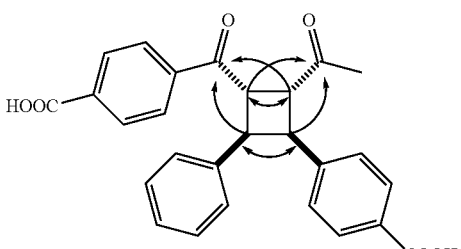

Important NOE-contacts

[structure]

Important HMBC-contacts

Ir System: anti-4-(2-acetyl-3-benzoyl-4-phenylcyclobutyl)benzoic Acid (FIG. 3, Control Study, Compound 32)

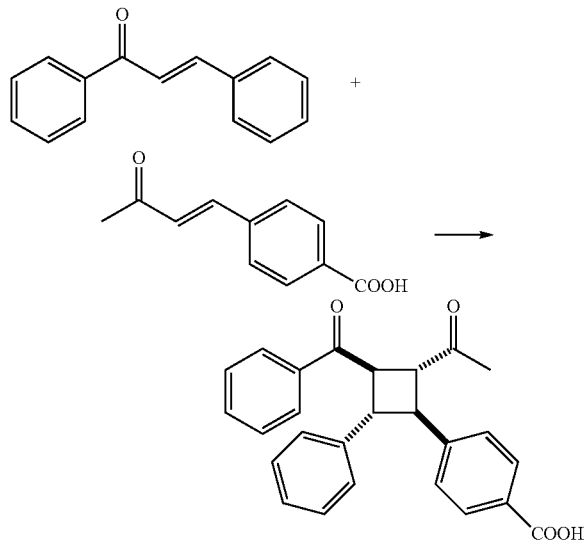

Prepared according to general procedure using 2.3 mg (0.011 mmol, 1.0 equiv.) chalcone Compound 23 (the sensitized molecule), 6.33 mg (0.033 mmol, 3.0 equiv.) (E)-4-(3-oxobut-1-en-1-yl)benzoic acid (Compound 2—the coupling partner). The crude products were purified by reverse phase preparative HPLC (Agilent C18 250×21.20 mm; 10 μm; eluted with a gradient of 35-60% MeCN:water with 0.1% formic acid over 80 min, then 20 min at 100% MeCN. The flow rate was 10 mL/min.) yielding major product anti-4-(2-acetyl-3-benzoyl-4-phenylcyclobutyl)benzoic acid (Compound 32) (2.1 mg, 43%) and minor product the syn-diastereomer (Compound S3) (0.6 mg, 12%), both as white powders.

anti Diastereomer (Compound 32, major product):

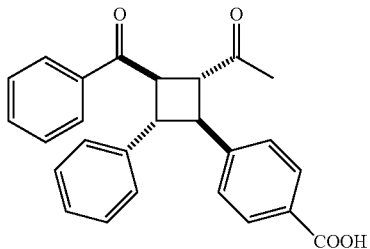

$^1$H NMR (600 MHz, DMSO-d$_6$): δ=7.93-7.89 (m, 2H), 7.80 (d, J=7.6 Hz, 2H), 7.60 (t, J=7.4 Hz, 1H), 7.47-7.44 (m, 2H), 7.41 (t, J=7.8 Hz, 2H), 7.33-7.30 (m, 4H), 7.27-7.25 (m, 1H), 4.48 (t, J=8.4 Hz, 1H), 3.88-3.78 (m, 2H), 3.63 (t, J=9.0 Hz, 1H), 2.02 (s, 3H).

$^{13}$C NMR (126 MHz, DMSO-d$_6$): δ=206.53, 198.26, 167.14, 140.68, 135.34, 133.65, 129.62 (2C), 128.63, 128.62, 128.49, 127.34, 127.20, 127.16 (2C), 50.47, 47.59, 46.92, 45.91, 28.00.

HRMS (ESI$^-$) (m/z): [M-H]$^-$ calculated for C$_{26}$H$_{21}$O$_4$, 397.1440; found, 397.1445.

Important NOE-contacts

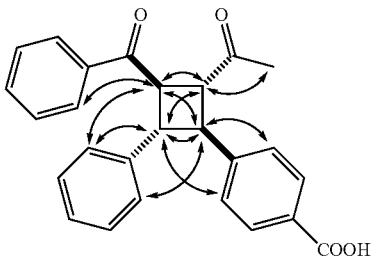

syn Diastereomer (Compound S3, minor product):

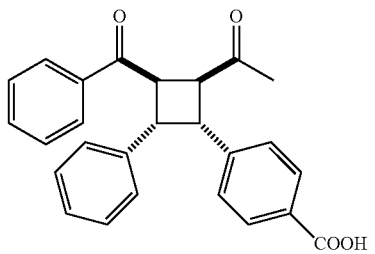

$^1$H NMR (600 MHz, DMSO-d$_6$): δ=7.90 (d, J=7.8 Hz, 2H), 7.63 (t, J=7.5 Hz, 3H), 7.51 (t, J=7.7 Hz, 2H), 7.17 (d, J=8.0 Hz, 2H), 7.15-7.07 (m, 4H), 7.07-6.99 (m, 1H), 4.91 (dd, J=9.4, 6.7 Hz, 1H), 4.37-4.32 (m, 1H), 4.25-4.21 (m, 1H), 4.14 (dd, J=10.3, 6.6 Hz, 1H), 2.00 (s, 3H).

$^{13}$C NMR (126 MHz, DMSO-d$_6$): δ=206.67, 198.55, 165.64, 139.07, 139.05, 135.52, 129.02, 128.98, 128.50 (2C), 128.05, 127.76, 127.27 (2C), 126.08, 50.70, 46.95, 44.00, 43.65, 28.20.

HRMS (ESI$^-$) (m/z): [M-H]$^-$ calculated for C$_{26}$H$_{21}$O$_4$, 397.1440; found, 397.1437.

Important NOE-contacts

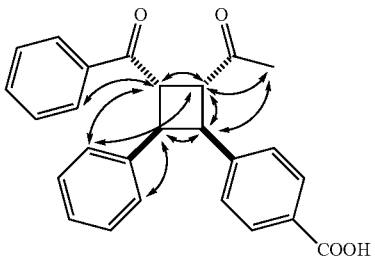

Example 8

X-Ray Crystallographic Data for Compound 8

Single crystals of Compound 8 were prepared by vapor diffusion of hexanes into MeOH at room temperature. A suitable crystal was selected and mounted in inert oil and transferred to the cold gas stream of a prospector diffractometer. The crystal was kept at 100 K during data collection. Using Olex2 (Dolomanov at al. *J. Appl. Crystallogr.* 42, 339-341 (2009)), the structure was solved with the ShelXT (Sheldrick, G. M. *Acta Crystallogr. Sect. A: Found. Adv.* 71, 3-8 (2015)) structure solution program using Intrinsic Phasing and refined with the XL (Sheldrick, G. M. *Acta Crystallogr.* Sect. A: Found. Crystallogr. 64, 112-122 (2008)) refinement package using Least Squares minimization.

Figure 5:
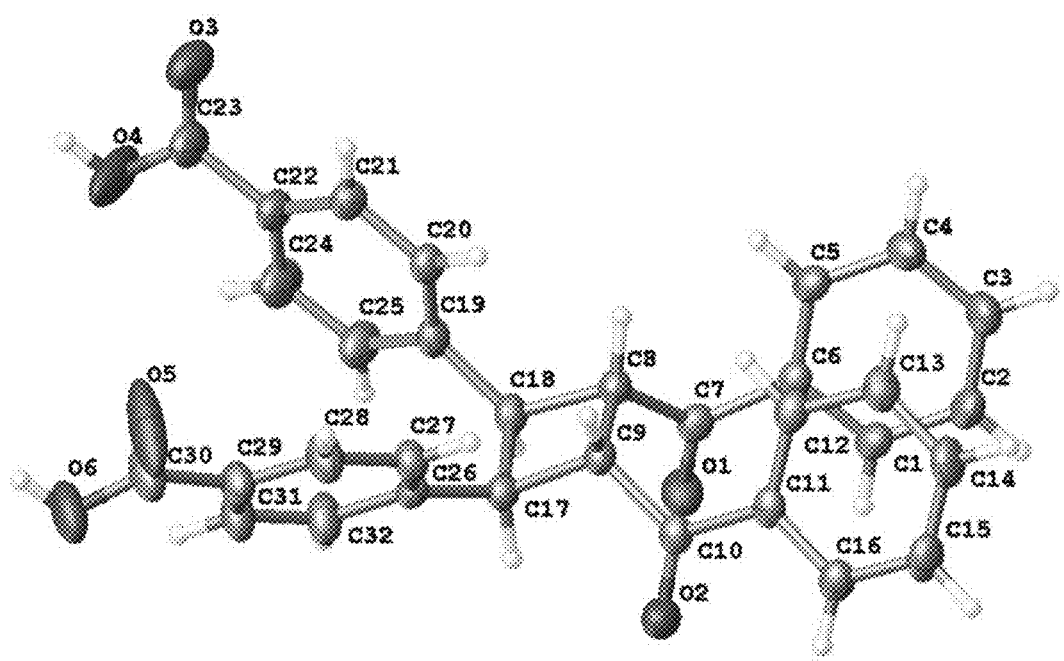
FIG. 5 shows a molecular drawing of the crystal structure of Compound 8, shown with 50% probability ellipsoids, as described in Example 8.

A molecular drawing of the crystal structure of Compound 8 shown with 50% probability ellipsoids is shown in FIG. 5.

Crystal Data for $C_{32}H_{24}O_6$ (M=504.51): orthorhombic, space group Pbca (no. 61), a=14.6934(15) Å, b=11.1245(12) Å, c=36.222(3) Å, V=5920.7(10) Å$^3$, Z=8, T=100 K, µ(CuKα)=0.637 mm$^{-1}$, Dcalc=1.132 g/mm$^3$, 46142 reflections measured (7.748≤2Θ≤135.366), 5278 unique ($R_{int}$=0.0585, $R_{sigma}$=0.0327) which were used in all calculations. The final $R_1$ was 0.0455 (I>2σ(I)) and wR2 was 0.1256 (all data).

Additional mechanistic details can be found in Jiang et al. "Regio- and Diastereoselective Intermolecular [2+2] Cycloadditions Photocatalyzed by Quantum Dots," ChemRxiv™ 2019, and in Jiang et al. "Regio- and diastereoselective intermolecular [2+2] cycloadditions photocatalysed by quantum dots," Nat. Chem. 2019, 11(11) 1034-1040, the entire contents of each of which are hereby incorporated by reference.

The invention claimed is:

1. A method of synthesizing a substituted cyclobutane compound, the method comprising:
   (a) providing a compound of formula (I) and a compound of formula (II):

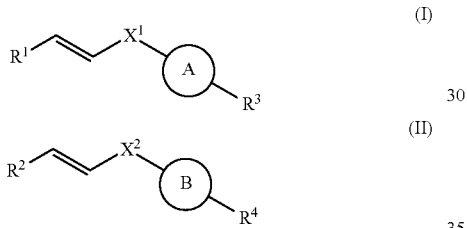

wherein:
   $X^1$ and $X^2$ are each independently selected from a bond and —C(O)—;
   $R^1$ and $R^2$ are each independently selected from hydrogen, alkyl, cycloalkyl, aryl, heterocyclyl, heteroaryl, —C(O)-alkyl, and —C(O)-aryl; and
   $R^3$ and $R^4$ are each independently selected from —COOH and —NH$_2$;
   A and B are each independently selected from aryl;
   wherein each alkyl, cycloalkyl, aryl, heterocyclyl, and heteroaryl is optionally substituted;
   (b) providing a plurality of quantum dots;
   (c) combining the compound of formula (I), the compound of formula (II), and the quantum dots in a solvent to provide a mixture; and
   (d) subjecting the mixture to irradiation,
   to thereby synthesize the substituted cyclobutane compound.

2. The method of claim 1, wherein the substituted cyclobutane compound is a compound of formula (III):

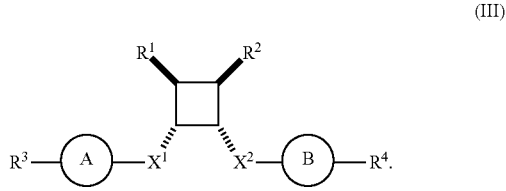

3. The method of claim 2, wherein the compound of formula (III) is synthesized with a diastereomeric ratio of greater than 10:1 compared to a compound of formula (IV):

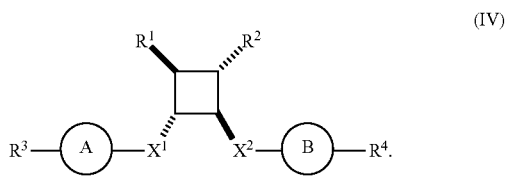

4. The method of claim 2, wherein the compound of formula (III) is synthesized with a ratio of greater than 10:1 compared to a compound of formula (V):

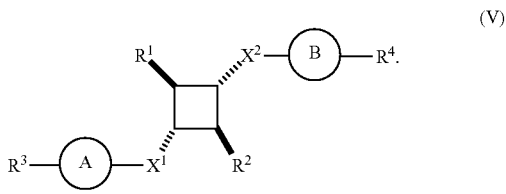

5. The method of claim 1, wherein the compound of formula (I) is a compound of formula (Ia), and the compound of formula (II) is a compound of formula (IIa):

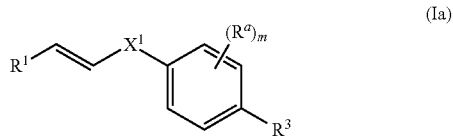

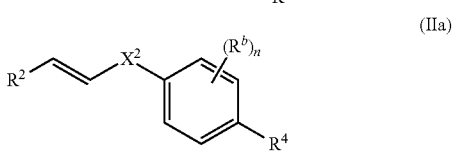

wherein:
   $R^a$ and $R^b$ are each independently selected from alkyl, alkenyl, alkynyl, halogen, haloalkyl, cycloalkyl, cycloalkenyl, aryl, —OR, —C(O)R, —C(O)OR, —NRR', —C(O)NRR', and —NR'C(O)R;
   each R is independently selected from alkyl, alkenyl, alkynyl, cycloalkyl, cycloalkenyl, aryl, heteroaryl, and heterocyclyl;
   each R' is independently selected from hydrogen, alkyl, alkenyl, alkynyl, cycloalkyl, cycloalkenyl, aryl, heteroaryl, and heterocyclyl;
   m is 0, 1, or 2; and
   n is 0, 1, or 2.

6. The method of claim 5, wherein the substituted cyclobutane compound is a compound of formula (IIIa):

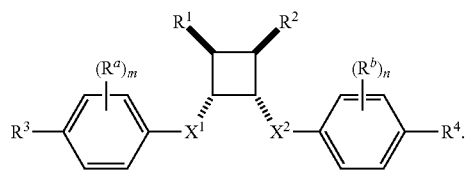
(IIIa)

7. The method of claim 1, wherein the compound of formula (I) is a compound of formula (Ib), and the compound of formula (II) is a compound of formula (IIb):

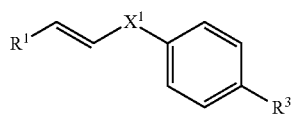
(Ib)

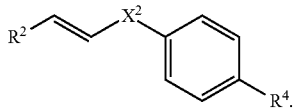
(IIb)

8. The method of claim 7, wherein the substituted cyclobutane compound is a compound of formula (IIIb):

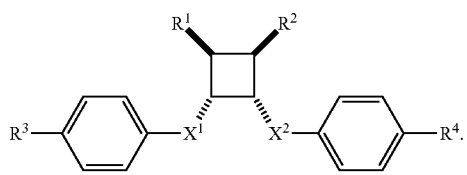
(IIIb)

9. The method of claim 1, wherein the compound of formula (I) and the compound of formula (II) are the same.

10. The method of claim 1, wherein the compound of formula (I) and the compound of formula (II) are different.

11. The method of claim 1, wherein the quantum dots are CdSe quantum dots.

12. The method of claim 1, further comprising separating the quantum dots from the substituted cyclobutane compound after step (d).

13. The method of claim 1, wherein the quantum dots have an average radius of 1.0 to 1.4 nm.

14. The method of claim 1, wherein the quantum dots further comprise a capping molecule on the surface of the quantum dots.

15. The method of claim 14, wherein the capping molecule is oleic acid.

16. The method of any claim 1, wherein the solvent is tetrahydrofuran.

17. The method of claim 1, comprising irradiating the mixture for 24-72 hours.

18. The method of any claim 1, comprising irradiating the mixture using a 16.5 W white-light LED with a 455 nm longpass filter.

19. The method of claim 1, comprising irradiating the mixture using a blue LED with emission centered at 467 nm.

20. The method of claim 1, wherein the quantum dots are present in the mixture in an amount of 0.4 mol % to 1.2 mol %.

* * * * *

UNITED STATES PATENT AND TRADEMARK OFFICE
CERTIFICATE OF CORRECTION

PATENT NO. : 10,961,178 B2
APPLICATION NO. : 16/851974
DATED : March 30, 2021
INVENTOR(S) : Jiang et al.

Page 1 of 1

It is certified that error appears in the above-identified patent and that said Letters Patent is hereby corrected as shown below:

In the Claims

At Column 66, Line 28, "The method of any claim 1" should read --The method of claim 1--.

At Column 66, Line 32, "The method of any claim 1" should read --The method of claim 1--.

Signed and Sealed this
Twelfth Day of April, 2022

Drew Hirshfeld
*Performing the Functions and Duties of the
Under Secretary of Commerce for Intellectual Property and
Director of the United States Patent and Trademark Office*